(12) United States Patent
Murahara

(10) Patent No.: US 10,407,780 B2
(45) Date of Patent: Sep. 10, 2019

(54) ELECTROCHEMICAL REACTOR COMPRISING LIQUID-REPELLENT POROUS MEMBRANE

(71) Applicant: M Hikari & Energy Laboratory Co., Ltd., Kamakura (JP)

(72) Inventor: Masataka Murahara, Kamakura (JP)

(73) Assignee: M Hikari & Energy Laboratory Co., Ltd. (JP)

( * ) Notice: Subject to any disclaimer, the term of this patent is extended or adjusted under 35 U.S.C. 154(b) by 562 days.

(21) Appl. No.: 15/060,421

(22) Filed: Mar. 3, 2016

(65) Prior Publication Data

US 2016/0186334 A1    Jun. 30, 2016

Related U.S. Application Data

(63) Continuation of application No. PCT/JP2014/073687, filed on Sep. 8, 2014.

(30) Foreign Application Priority Data

Sep. 6, 2013    (JP) .................................. 2013-185290

(51) Int. Cl.
  *C25B 1/10*    (2006.01)
  *H01M 2/14*    (2006.01)
  (Continued)

(52) U.S. Cl.
  CPC .................. *C25B 1/10* (2013.01); *C25B 1/16* (2013.01); *C25B 1/34* (2013.01); *C25B 9/08* (2013.01);
  (Continued)

(58) Field of Classification Search
  USPC ................................................ 429/110–119
  See application file for complete search history.

(56) References Cited

U.S. PATENT DOCUMENTS 3,897,266 A * 7/1975 Devitt ................... H01M 10/34
                                                     429/166
4,212,714 A    7/1980 Coker et al.
(Continued)

FOREIGN PATENT DOCUMENTS

CN        2687584 Y    3/2005
EP        0644227 A1   3/1995
                 (Continued)

OTHER PUBLICATIONS

Smirnov et al, Water Confinement in Hydrophobic Nanopores. Pressure-Induced Wetting and Drying, ACS Nano, vol. 4, No. 9, Aug. 2010, pp. 5069-5075 (Year: 2010).*

(Continued)

*Primary Examiner* — Harry D Wilkins, III
(74) *Attorney, Agent, or Firm* — Harness, Dickey & Pierce, P.L.C.

(57) ABSTRACT

An electrochemical reactor includes positive and negative electrodes. A conductive and/or dielectric liquid is provided between the positive and negative electrodes. A first isolation member provided on the positive electrode isolates the positive electrode from the liquid, and a second isolation member provided on the negative electrode isolates the negative electrode from the liquid. The first and second isolation member each includes a liquid-repellent porous membrane. The reactor further includes a pressure-applying member which pressurizes the liquid to fill the pores of the first and second liquid-repellent porous membranes with the liquid, thereby causing an electrochemical reaction involving the positive and negative electrodes.

18 Claims, 48 Drawing Sheets

(51) Int. Cl.

| | | |
|---|---|---|
| H01M 2/36 | (2006.01) | |
| H01M 6/30 | (2006.01) | |
| H01G 9/02 | (2006.01) | |
| H01G 9/035 | (2006.01) | |
| H01G 11/52 | (2013.01) | |
| H01M 10/36 | (2010.01) | |
| H01M 6/32 | (2006.01) | |
| C25B 1/16 | (2006.01) | |
| C25B 9/08 | (2006.01) | |
| H01G 9/048 | (2006.01) | |
| H01G 9/07 | (2006.01) | |
| H01G 9/10 | (2006.01) | |
| H01G 9/145 | (2006.01) | |
| H01G 9/21 | (2006.01) | |
| H01M 6/04 | (2006.01) | |
| H01M 6/16 | (2006.01) | |
| H01M 6/22 | (2006.01) | |
| H01M 6/34 | (2006.01) | |
| H01M 6/36 | (2006.01) | |
| H01M 6/38 | (2006.01) | |
| H01M 10/0566 | (2010.01) | |
| H01M 10/26 | (2006.01) | |
| H01M 12/08 | (2006.01) | |
| C25B 11/03 | (2006.01) | |
| C25B 1/34 | (2006.01) | |
| A61F 7/03 | (2006.01) | |
| A61B 18/04 | (2006.01) | |
| A61F 7/12 | (2006.01) | |

(52) U.S. Cl.
CPC ............ *C25B 11/035* (2013.01); *H01G 9/02* (2013.01); *H01G 9/035* (2013.01); *H01G 9/048* (2013.01); *H01G 9/07* (2013.01); *H01G 9/10* (2013.01); *H01G 9/145* (2013.01); *H01G 9/21* (2013.01); *H01G 11/52* (2013.01); *H01M 2/14* (2013.01); *H01M 2/36* (2013.01); *H01M 6/04* (2013.01); *H01M 6/045* (2013.01); *H01M 6/162* (2013.01); *H01M 6/22* (2013.01); *H01M 6/32* (2013.01); *H01M 6/34* (2013.01); *H01M 6/36* (2013.01); *H01M 6/38* (2013.01); *H01M 10/0566* (2013.01); *H01M 10/26* (2013.01); *H01M 10/36* (2013.01); *H01M 12/08* (2013.01); *A61B 18/04* (2013.01); *A61B 2018/046* (2013.01); *A61F 7/03* (2013.01); *A61F 2007/126* (2013.01); *H01M 2300/0014* (2013.01); *H01M 2300/0025* (2013.01); *H01M 2300/0048* (2013.01); *Y02E 60/13* (2013.01); *Y02E 60/366* (2013.01); *Y02P 20/129* (2015.11); *Y02P 20/133* (2015.11); *Y02P 20/134* (2015.11); *Y02T 10/7022* (2013.01)

(56) References Cited

U.S. PATENT DOCUMENTS

| | | | | |
|---|---|---|---|---|
| 4,214,958 | A | | 7/1980 | Coker et al. |
| 4,992,156 | A | | 2/1991 | Silveri |
| 6,117,497 | A | | 9/2000 | Murahara et al. |
| 6,167,497 | A | | 12/2000 | Nakatsuka et al. |
| 10,087,536 | B2 | * | 10/2018 | Winther-Jensen .... C25B 11/035 |
| 2001/0045364 | A1 | * | 11/2001 | Hockaday .......... B01D 19/0031 |
| | | | | 205/338 |
| 2002/0134674 | A1 | * | 9/2002 | Andrews ................. A61L 2/183 |
| | | | | 204/242 |
| 2005/0208370 | A1 | * | 9/2005 | Hodes ...................... H01M 4/06 |
| | | | | 429/118 |
| 2007/0080069 | A1 | * | 4/2007 | Melosi ....................... C25B 1/12 |
| | | | | 205/338 |
| 2009/0042066 | A1 | * | 2/2009 | Simon ..................... H01M 6/32 |
| | | | | 429/10 |
| 2010/0051450 | A1 | | 3/2010 | Murahara |
| 2011/0135565 | A1 | * | 6/2011 | Bingham ................... B01J 7/02 |
| | | | | 423/657 |
| 2012/0202279 | A1 | | 8/2012 | Murahara |
| 2012/0292187 | A1 | | 11/2012 | Kim et al. |
| 2015/0292094 | A1 | * | 10/2015 | Swiegers ................. C25B 1/04 |
| | | | | 204/282 |
| 2016/0230250 | A1 | * | 8/2016 | Chung ....................... C02F 1/28 |
| 2019/0046945 | A1 | * | 2/2019 | Murahara ................. C25B 9/18 |

FOREIGN PATENT DOCUMENTS

| | | | | |
|---|---|---|---|---|
| JP | S565989 A | | 1/1981 | |
| JP | S565990 A | | 1/1981 | |
| JP | 09-180714 A | | 7/1997 | |
| JP | 2001-284177 A | | 10/2001 | |
| JP | 2002-063890 A | | 2/2002 | |
| JP | 2003-123808 A | | 4/2003 | |
| JP | 2003-123808 A | | 4/2003 | |
| JP | 2005-253305 A | | 9/2005 | |
| JP | 2006-193612 A | | 7/2006 | |
| JP | 2009-067644 A | | 4/2009 | |
| JP | 2009-181710 A | | 8/2009 | |
| JP | 2009-224097 A | | 10/2009 | |
| JP | 2009-295789 A | | 12/2009 | |
| JP | 2011-184260 A | | 9/2011 | |
| JP | 2011-222129 A | | 11/2011 | |
| JP | 2012-012261 A | | 1/2012 | |
| JP | 2012-030637 A | | 2/2012 | |
| JP | WO 2012/023535 A1 | * | 2/2012 | ............. C25B 1/04 |
| JP | 2012-041578 A | * | 3/2012 | ............. C25B 1/04 |
| JP | 2013-032535 A | | 2/2013 | |
| JP | 2013-054987 A | | 3/2013 | |
| JP | 2013-138050 A | | 7/2013 | |
| JP | 2013-166406 A | | 8/2013 | |
| WO | WO-01-31724 A1 | | 5/2001 | |
| WO | WO-2007-080763 A1 | | 7/2007 | |

OTHER PUBLICATIONS

Barbe et al, Surface Morphology changes during initial usage of hydrophobic, microporous polypropylene membranes, Journal of Membrane Science, vol. 172, No. 1-2, Jul. 2000, pp. 149-156 (Year: 2000).*

All About Nafion, downloaded from https://www.permapure.com/resources/all-about-nafion-and-faq/ on Oct. 9, 2018, (Year: 2018).*

International Preliminary Report and Written Opinion of the International Searching Authority dated Mar. 17, 2016 in International Application No. PCT/JP2014/073687 (5 pages).

Masataka Murahara et al. "Hydrophilic Treatment of Porous PTFE for Intractable Glaucoma Implant Devices". Proceedings of SPIE, vol. 4245, Jun. 7, 2001; pp. 221-227; (7 pages).

Masataka Murahara. "Consider Renewable Energy (Goodbye to Nuclear Power Plant)". Power Publication, Nov. 15, 2011; p. 14 (3 pages) (without English translation).

Masataka Murahara et al. "Wind Force" Save Corn From Ethanolization (Collection of Marine Resources and On-Sea Factory by Wind Power Generation). Power Publication, Dec. 25, 2007; pp. 10-11 (3 pages) (without English translation).

Michio Okamura. "Electric Double Layer Capacitor and Power Storage System". Nikkan Kogyo Shimbun, Mar. 31, 1999; pp. 32-33 (3 pages) (without English translation).

International Search Report for International Application No. PCT/JP2014/073687 dated Dec. 16, 2014 with English Translation (3 pages).

Partial Supplementary European Search Report dated May 9, 2017 regarding EP Application 14842245.4 (16 pages).

Second Office Action issued by the State Intellectual Property Office of the People's Republic of China dated Jul. 4, 2017 regarding Chinese Application No. 201480049132.1 (18 pages).

(56) References Cited

OTHER PUBLICATIONS

Office Action dated Sep. 4, 2018 in corresponding Japanese Application No. 2015-535545 (with English translation) (29 pages).

* cited by examiner

Discharge capacities of base metal/oxygen or halogen batteries [Wh/kg]

| Positive electrode → Potential (V) <br> Negative electrode ↓ | | $O_2$ (Air) +0.40(V) | $F_2$ +2.87 | $Cl_2$ +1.36 | $Br_2$ +1.08 | $I_2$ +0.53 |
|---|---|---|---|---|---|---|
| | Potential (V) / Valence | Discharge Capacitance (Wh/kg) | Discharge Capacitance (Wh/kg) | Discharge Capacitance (Wh/kg) | Discharge Capacitance (Wh/kg) | Discharge Capacitance (Wh/kg) |
| H | 0(V) / 1 | 596 | | | | |
| Li | -3.05 / 1 | 6,165(11,680) | | 2,782(16,888) | 964(15,815) | 716(13,709) |
| Na | -2.72 / 1 | 2,698(3,636) | 3,568(6,515) | 1,870(4,755) | 989(4,429) | 617(3,788) |
| K | -2.92 / 1 | 1,278(1,894) | 2,676(3,980) | 1,540(2,942) | 901(2,749) | 383(2,371) |
| Be | -1.84 / 2 | 3,532(6,672) | | 2,169(19,049) | | |
| Mg | -2.35 / 2 | 3,658(6,067) | | 2,087(8,185) | 998(3,784) | 555(3,177) |
| Ca | -2.84 / 2 | 3,102(4,343) | | 2,029(5,112) | 3,302(2,627) | 615(2,258) |
| Sr | -2.89 / 2 | 1,703(2,014) | | 1,437(2,601) | 860(1,215) | 345(1,047) |
| Ba | -2.92 / 2 | 1,228(1,299) | | 1,330(1,675) | 361(783) | 237(675) |
| Al | -1.67 / 3 | 3,264(6,165) | 2,589(13,522) | 1,813(9,025) | | |
| Zn | -0.76 / 2 | 764(951) | | 535(1,738) | 438(754) | 246(529) |
| Ni | -0.72 / 2 | | | 860 | 441 | |
| Pb | -1.26 / 2 | | | | | 208(232) |
| Mn | -1.26 / 2 | | | 1,115(2,554) | 583(1,140) | |
| Fe | -0.44 / 2 | | | 760 | 377 | |
| Cd | -0.40 / 2 | | | 516 | 292 | 136 |
| Co | -0.28 / 2 | | | 676 | 333 | 139 |

(Discharge Capacitance when weight of gas is neglected)     Discharge Capacitance = 26806 V n/M [Wh/kg]

F I G. 1

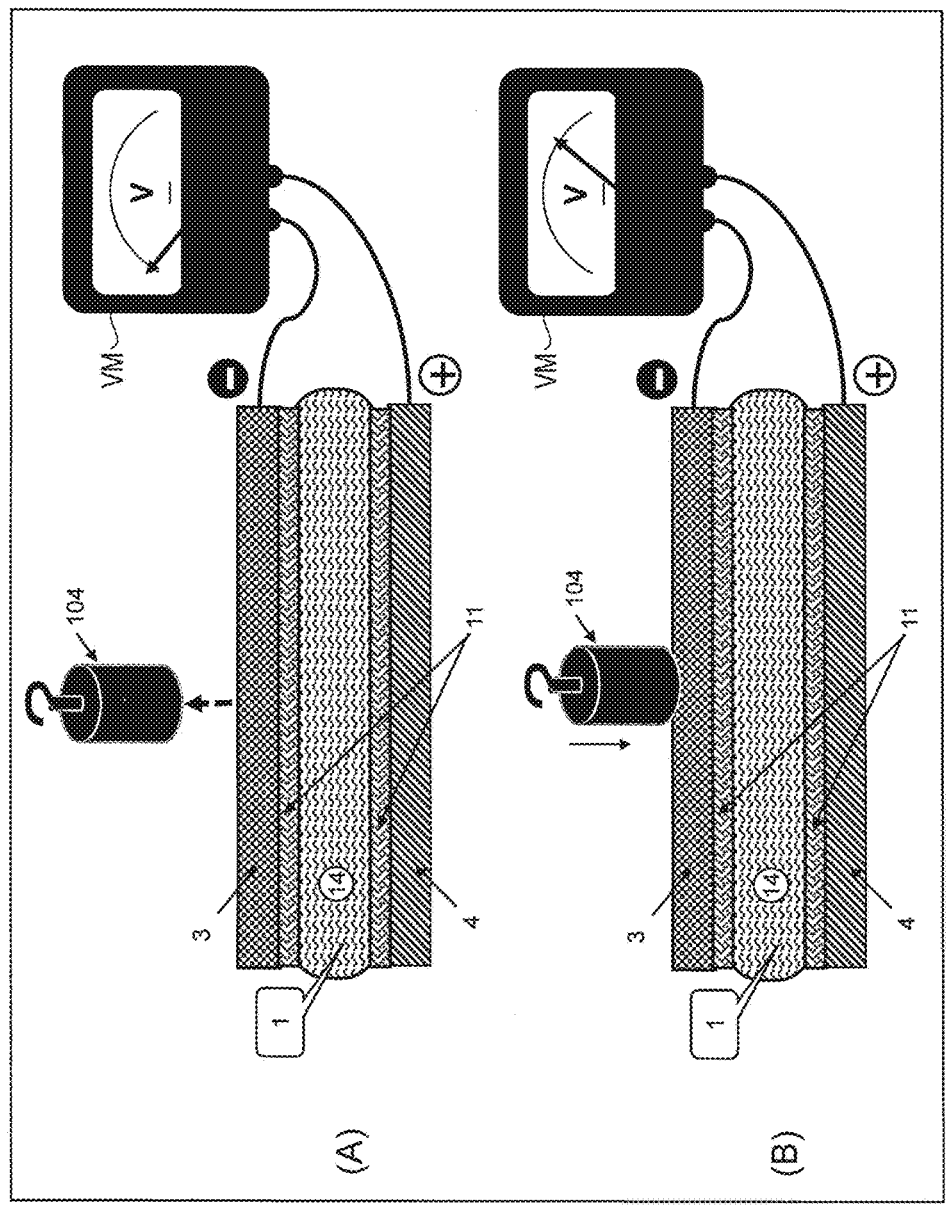
F I G. 2

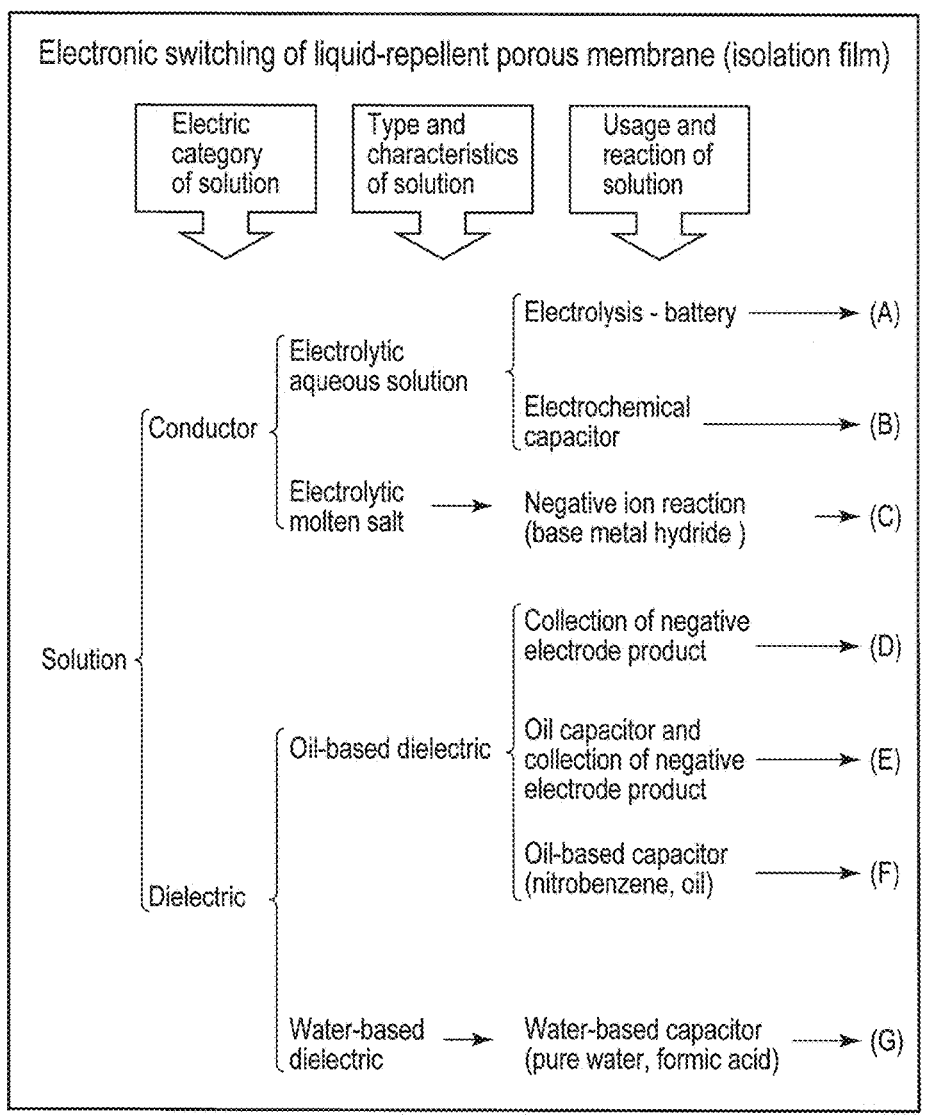
F I G. 3A

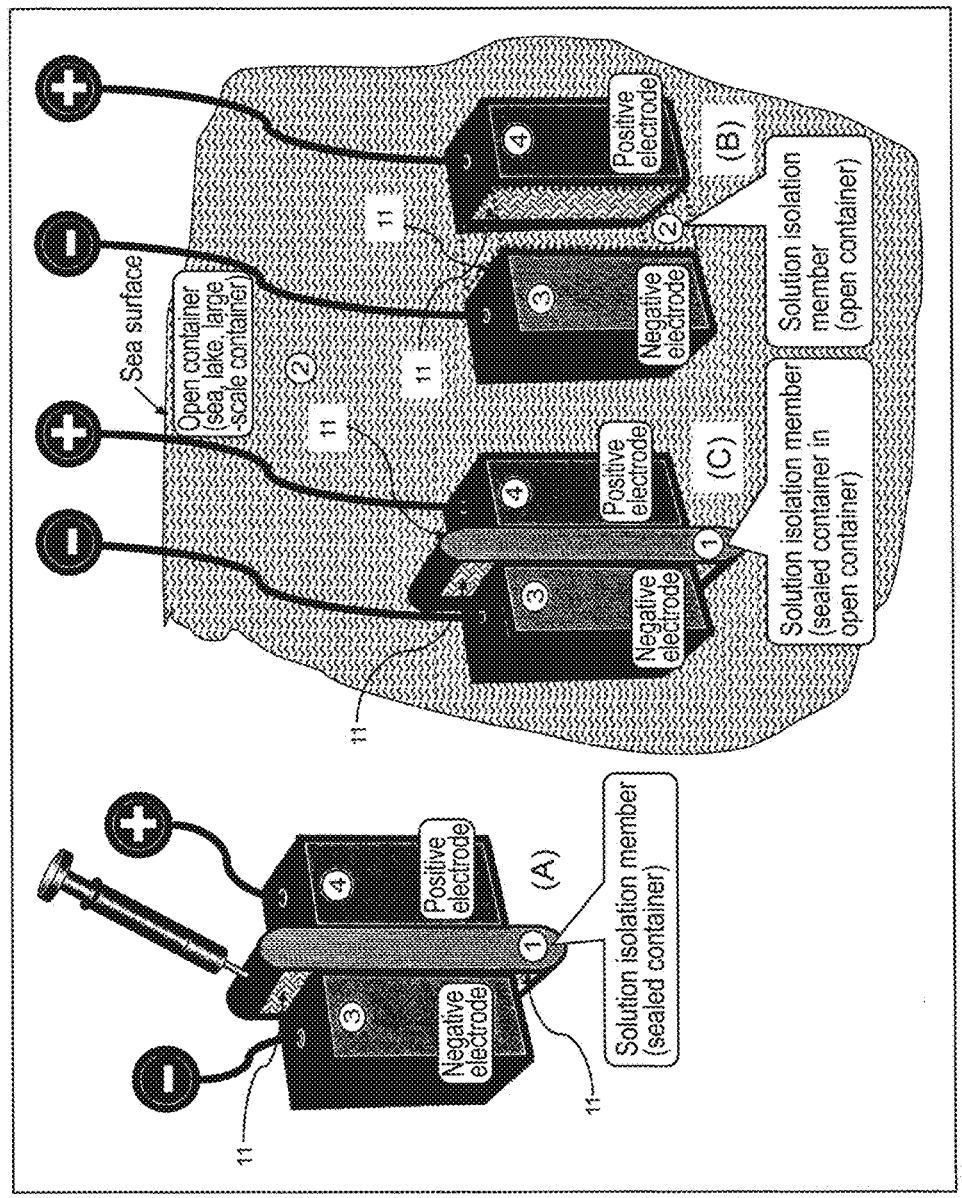
F I G. 4

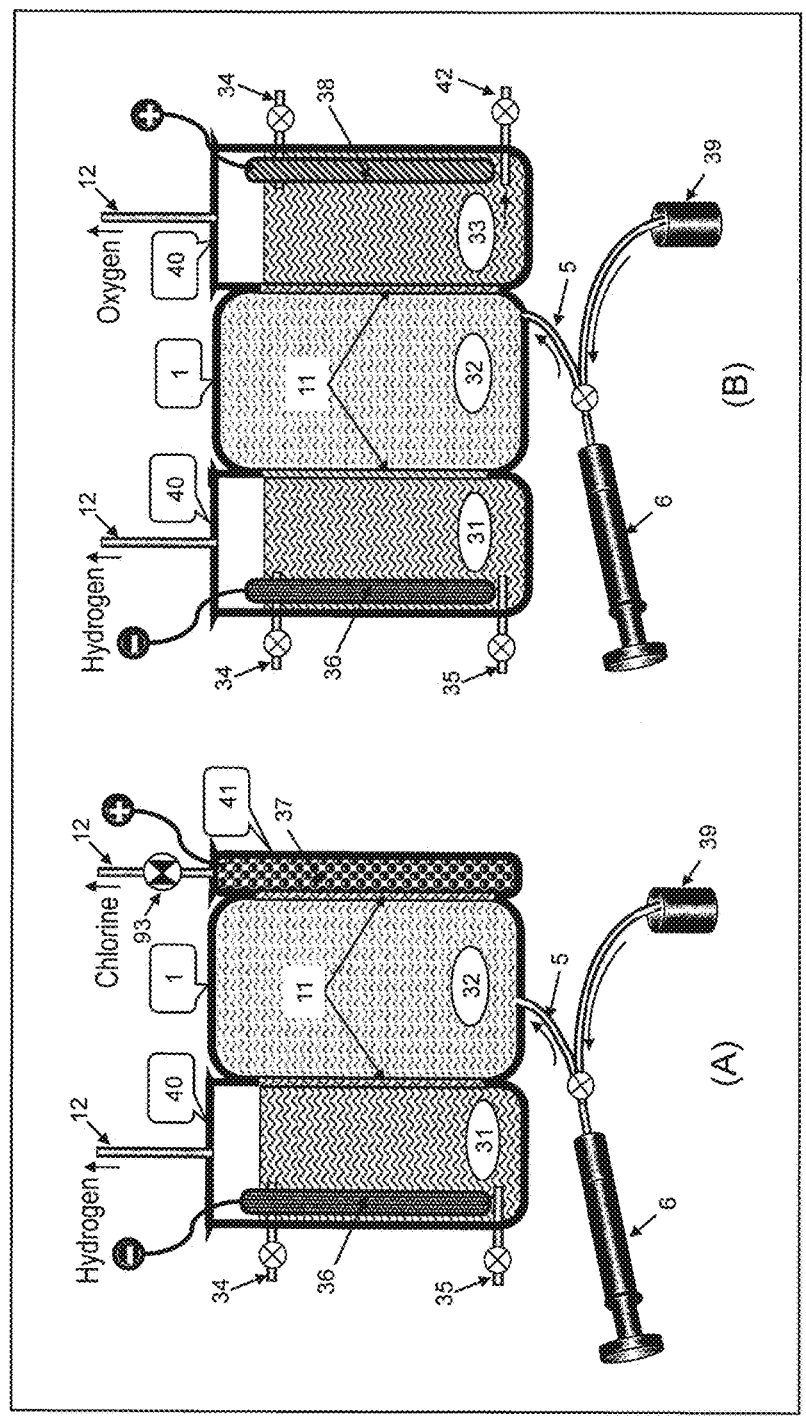
F I G. 12

|  | Na | Mg | Ca | Al | Li | K | Sr | Ba |
|---|---|---|---|---|---|---|---|---|
| Melting point of oxide | 1275 | 2800 | 2572 | 2054 | 1570 | 490 | 2430 | 1918 |
| Melting point of chloride | 801 | 714 | 772 | 193 | 605 | 770 | 769 | 925 |
| Melting point of hydroxide | 318 | 651 | 580 | 300 | 450 | 360 | 375 | 325 |
| Melting point of hydride | 800 | 287 | 816 | 150 | 680 | 417 |  | 675 |
| Specific gravity of hydride | 0.92 | 1.74 | 1.9 | 1.49 | 0.82 | 1.47 | 4.21 | |
| Specific gravity of hydroxide | 2.13 | 2.36 | 2.2 | 2.42 | 1.46 | 2.04 | 3.62 | 4.5 |
| Melting point of element | 98 | 651 | 848 | 660 | 179 | 64 | 769 | 725 |
| Specific gravity of element | 0.97 | 1.74 | 1.55 | 2.69 | 0.54 | 0.86 | 2.54 | 3.51 |

Base metal/oxygen or halogen battery

| Negative electrode (V) \ Positive electrode (V) | $O_2$ (+0.40) | $F_2$ (+2.87) | $Cl_2$ (+1.36) | $Br_2$ (+1.08) | $I_2$ (+0.53) |
|---|---|---|---|---|---|
| Li (-3.05) | ○ | × | ◎ | ◎ | ◎ |
| Na (-2.72) | ◎ | ○ | ○ | ◎ | ◎ |
| K (-2.92) | ◎ | ◎ | ◎ | ◎ | ◎ |
| Be (-1.84) | △× | Dissolved well | ◎ | Dissolved well | × Reaction |
| Mg (-2.35) | △× | × | ◎ | ◎ | ◎ |
| Ca (-2.84) | △× | × | ◎ | ◎ | ◎ |
| Sr (-2.89) | ○ | × | ◎ | ◎ | ◎ |
| Ba (-2.92) | ○ | × | ◎ | ◎ | ◎ |
| Al (-1.67) | △× | ○ | ◎ | × Reaction | × Reaction |
| Zn (-0.76) | △× | × | ◎ | ◎ | ◎ |
| Ni (-0.72) | × | × | ◎ | × | × |
| Pb (-1.26) | × | × | × | × | ○ |
| Mn (-1.26) | × | × | ◎ | ◎ | × |
| Fe (-0.44) | × | × | ◎ | ◎ | × |
| Cd (-0.40) | × | × | ◎ | ◎ | ◎ |
| Co (-0.28) | × | × | ◎ | ◎ | ◎ |

Solubility (60°C)
◎ 80% or more
◎ 60-80%
◎ 30-60%
○ 10-30%
∘ 1-10%
× 1% or less
△ Alkali added $Al(OH)_3 + NaOH \rightarrow Na[Al(OH)_4]$
Sodium tetrahydroxo aluminate
All Be compounds are highly poisonous
Br boiling point: 58.8°C
I boiling point: 113.6°C, almost insoluble in water

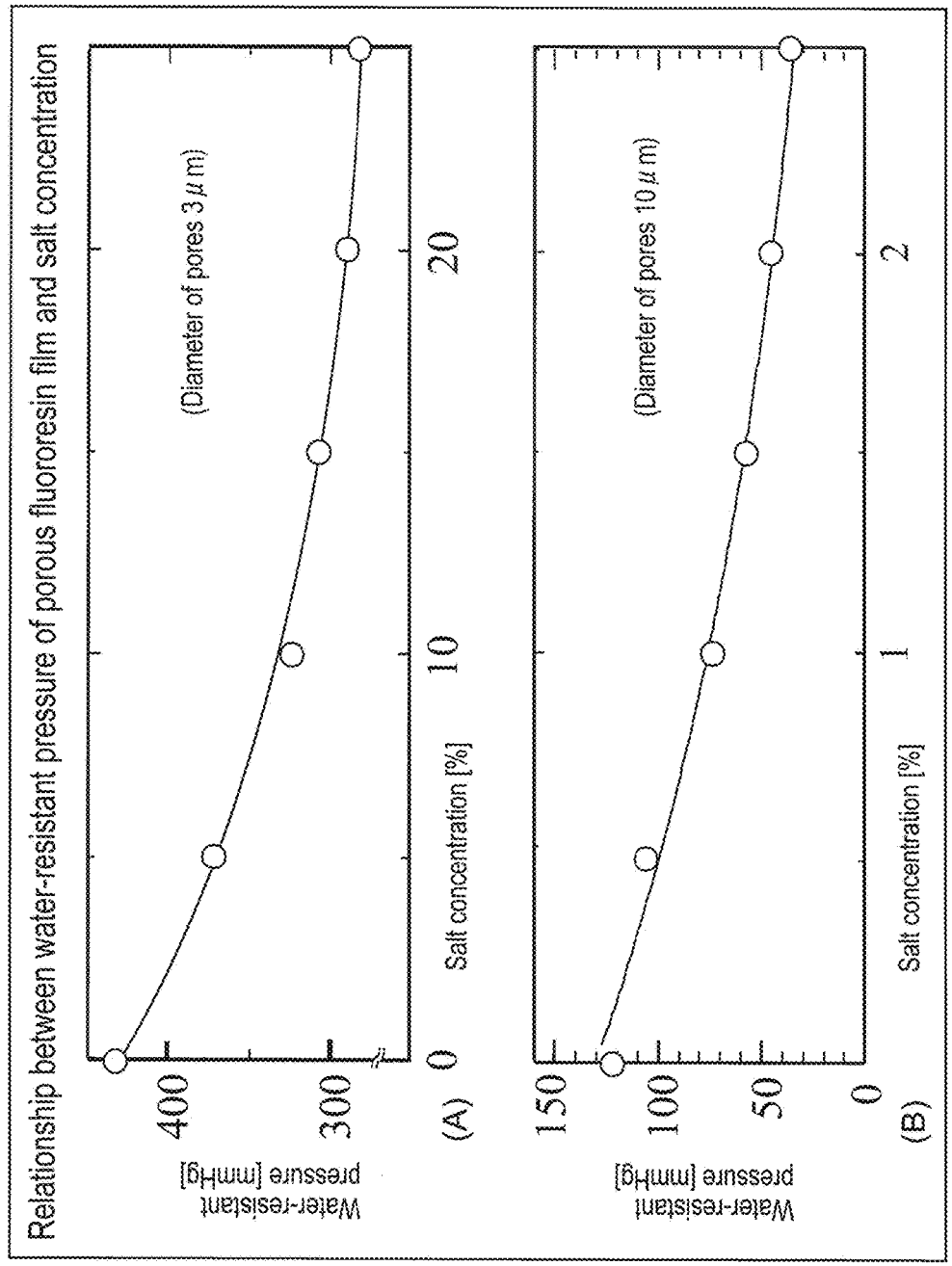
F I G. 28

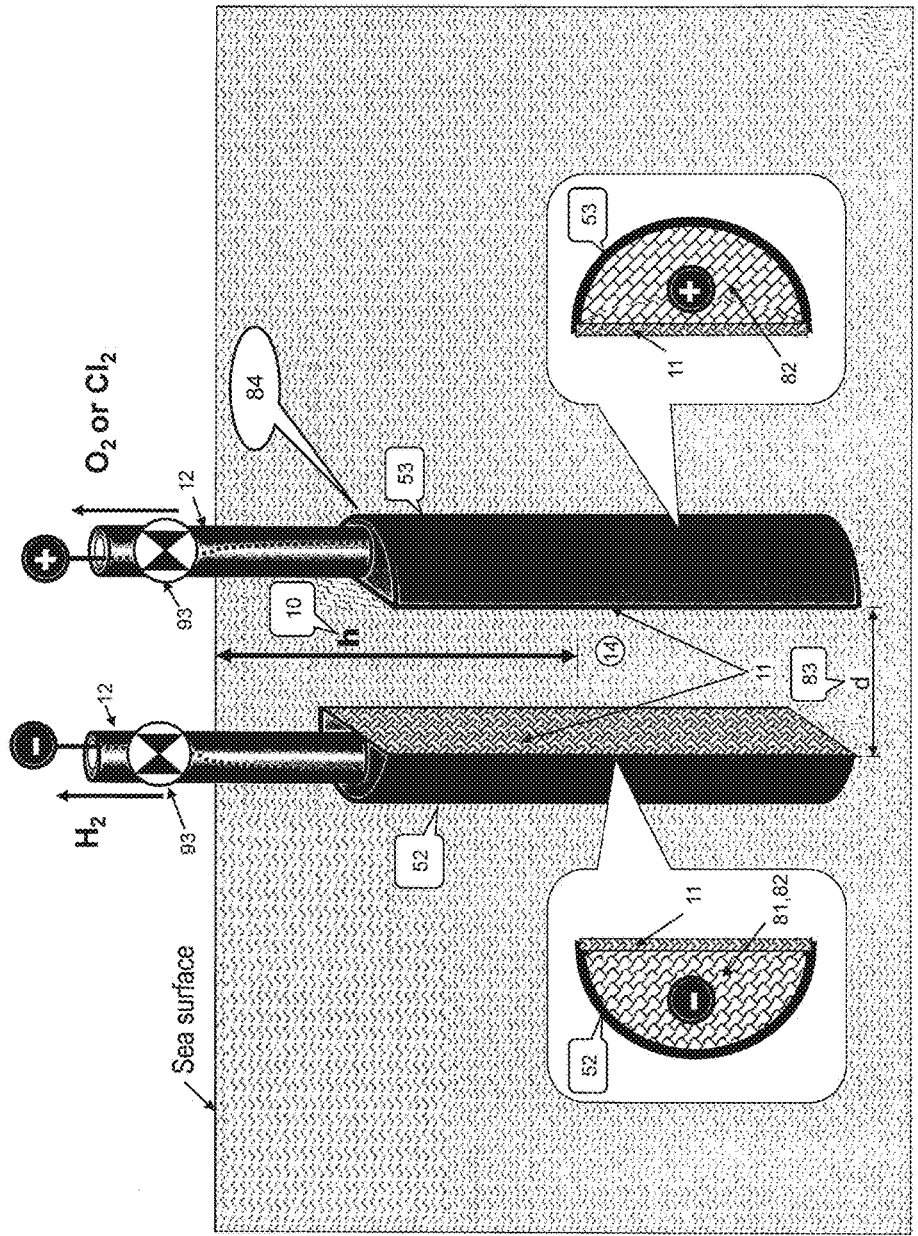
F I G. 29

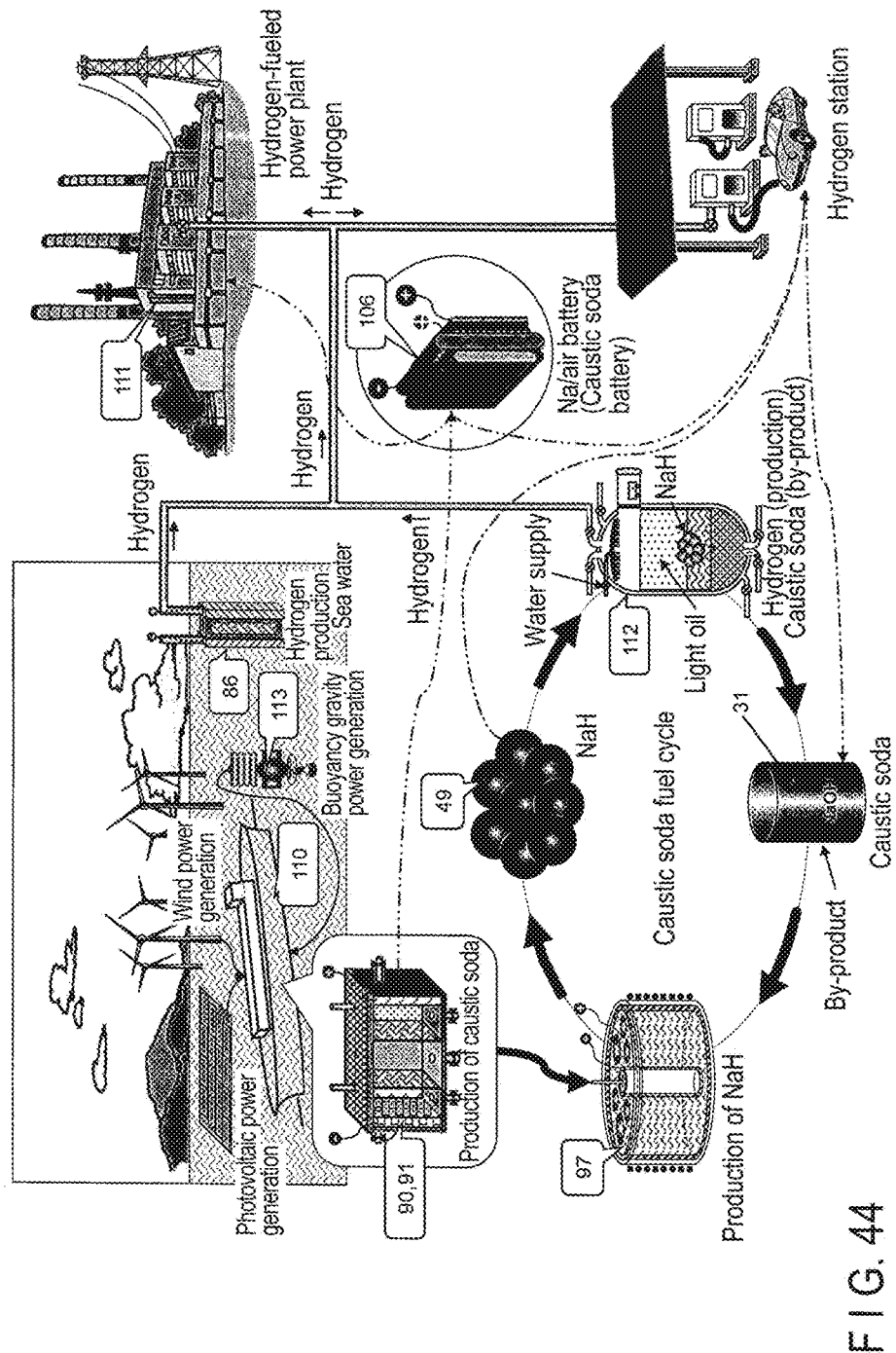
F I G. 44

ELECTROCHEMICAL REACTOR COMPRISING LIQUID-REPELLENT POROUS MEMBRANE

CROSS REFERENCE TO RELATED APPLICATIONS

This application is a Continuation application of PCT Application No. PCT/JP2014/073687, filed Sep. 8, 2014 and based upon and claiming the benefit of priority from prior Japanese Patent Application No. 2013-185290, filed Sep. 6, 2013, the entire contents of all of which are incorporated herein by reference.

BACKGROUND OF THE INVENTION

1. Field of the Invention

The present invention relates to an electrochemical reactor including an electrolytic refining device, a practical battery and capacitor, which utilizes resistance to fluid pressure of a liquid-repellent porous membrane.

2. Description of the Related Art

The base metal elements belonging to Group 1, Group 2 and Group 13 of the periodic table are ionized upon contacting water and immediately self-discharge, producing hydrogen. For this reason, these metal elements must be strictly prohibited from contacting water. Thus, as electrolytic refining to deposit these, there is no other production method than a molten salt electrolysis. In the practical batteries, there are no primary or secondary batteries which use an electrolyte solution with respect to Ca, Ba or Sr, which belongs to Group 1 or 2 of the periodic table. Further, there are primary batteries with respect to Be, Mg of the Group 2 elements, or aluminum, which is a Group 13 element of the periodic table, but there is no secondary battery with respect to these elements. As the secondary batteries, which include lithium ion batteries and sodium ion batteries of Group 1 elements, a nonaqueous electrolyte solution (organic electrolyte) or a solid electrolyte has been developed. Further, for a battery using sodium of Group 1 element, a sodium sulfur battery (NS battery), which operates at a high temperature of 300° C. or higher and uses sodium as a molten salt electrolyte, has been developed.

For practical batteries, a lighter electrode material, a higher electromotive force and a larger discharge capacity are presently in demand. Therefore, elements of Group 1 of the periodic table are ideal negative electrode materials, but it is difficult to avoid self-discharge. The reason why these practical batteries, electrolytic refining and capacitor causes self-discharge is that a negative electrode and a positive electrode are present in the same electrolyte solution. Under these circumstances, there are urgent technical developments in demand to inhibit self-discharge by separating the electrolyte and electrodes, and also to interrupt a base metal element of Group 1, 2 or 13 of the periodic table and water from each other.

For capacitors for power storage (capacitor), a larger capacity and a more rapid charge and discharge are desired. As a capacitor which fills these, an electrochemical capacitor is ideal, such as an electric double layer capacitor, a redox capacitor or a hybrid capacitor. Drawbacks of these capacitors are high leak current and self-discharge. Under these circumstances, there is an urgent technology development in demand to suppress the leakage current.

The self-discharge is a phenomenon in which the metal of the negative electrode dissolves and at the same time, electrons and hydrogen ions generated react with each other to produce hydrogen, with the result that the electrons do not move to the positive electrode, and thus current does not flow. As a general method of suppressing self-discharge in an aqueous electrolyte solution, Patent Literature 1 discloses that a nickel-based porous body is provided on a positive electrode for an alkali-storage battery, and the porous body is filled with particles of an active material which contains nickel and additives, thereby reducing self-discharge. Patent Literature 2 discloses a method of suppressing self-discharge by setting of such a shape of electrode that does not decrease the real reaction area even if the opposing area of the alkali storage battery electrode is increased. Patent Literature 3 discloses a long-life alkaline battery comprising, as a separator, a multi-layer member of a sheet comprising fibers containing sulfonated polyolefin resin fibers as a principal component, and a sheet subjected to a hydrophilization treatment other than sulfonation, with less self-discharge and high capacitance retention. Patent Literature 4 discloses an electrode for lithium batteries in which active material thin films which adsorb/release lithium, such as a microcrystal silicon thin film and an amorphous silicon thin film are provided on a charge collector via an interlayer. Patent Literature 5 discloses that as an electrode active material in a lithium battery, porous lithium titanate is excellent in the nonaqueous electrolyte impregnating properties and improves charge/discharging cycle characteristics. Patent Literature 6 discloses a sodium secondary battery comprising a positive electrode of a carbon-based positive electrode active material which can adsorb and release anions, and a negative electrode of a negative electrode material which can adsorb and release Na, which is, such as Sn or Zn. As to sodium sulfur batteries, in which sodium is molted, an atmosphere temperature of 300° C. is required to form a molten salt. But, Patent Literature 7 discloses the operation of a battery at an atmosphere temperature within a range of 60 to 130° C., which can be achieved by using a molten salt composite containing two or more types of molten salts MFSI comprising bisfluorosulfonylimide (FSI) for anions and alkali metal M for cations.

As to the isolation film between an electrolyte and an electrode, Patent Literature 8 discloses that a polyolefin microporous membrane having a pore diameter of 0.1 µm or less has thermal stability and therefore it is suitable as a separator for a high-capacity/high-output battery. Patent Literature 9 discloses that a scale-like inorganic porous membrane of silica, alumina or the like is provided on a positive electrode, a negative electrode or a separator, and thus the performance of a battery can be retained without degrading the ionic conductance. Patent Literature 10 discloses that an isolation film used for a nonaqueous secondary battery is a thermal-resistant porous membrane containing chlorine, or a multi-layered film of a thermal-resistant resin and porous polyolefin, or a multi-layered film of a layer including a thermal-resistant resin and a porous polyolefin.

As to the use of a water-repellent porous membrane, Patent Literature 11 discloses a fluorine-based water-repellent porous membrane having a porosity of 60 to 90% and an air permeability of 20 seconds or less is used in a solid polymer fuel cell. Patent Literatures 12, 13 and 14 each discloses a method of manufacturing a fluorine-based water-repellent porous membrane by irradiating a fluorine-based water-repellent porous membrane with an excimer laser beam in the presence of a compound comprising an atom and a hydrophilic group and having a bond energy therebetween of 128 or more kcal/mol. Further, Patent Literature 15 discloses a method of manufacturing a three-dimensional cell culture element for patients suffering from Parkinson's disease, Alzheimer disease, diabetes, osteomalacia and the like, in which inner pores of a fluorine-based water-repellent porous membrane are substituted with hydrophilic groups by photo-reaction caused by ultraviolet radiation, and dopamine-producing cells, fibrocytes, collagen production-promoting cells, stem cells, nucleus-pulposus cells, insulin-producing cells, etc. are cultured in the inner walls of the pores, which exhibit the hydrophilic properties. Furthermore, Masataka Murahara et al. reports in Non-patent Literature 1 that the water-resistant pressure of a water-repellent porous fluorine-based resin film with a pore diameter of 33 μm is 1500 torr, but the insides of the pores are photo-modified to be hydrophilic to lower the water-resistant pressure to 20 torr, and the thus modified film is used in an aqueous-humor regulating valve for glaucomatous patients.

CITATION LIST

Patent Literature

Patent Literature 1: JP H9-180714 A
Patent literature 2: JP 2009-181710 A
Patent literature 3: JP 2002-63890 A
Patent literature 4: WO 01/031724
Patent literature 5: JP 2012-12261 A
Patent literature 6: JP 2013-54987 A
Patent literature 7: JP 2009-67644 A
Patent literature 8: JP 2013-32535 A
Patent literature 9: JP 2011-222129 A
Patent literature 10: JP 2009-224097 A
Patent literature 11: WO 2007/80763
Patent literature 12: JP 2005-253305 A
Patent literature 13: U.S. Pat. No. 6,117,497
Patent literature 14: EP No. 0644227
Patent literature 15: JP 2011-184260 A
Patent literature 16: JP 2009-295789 A
Patent literature 17: JP 2013-138050 A
Patent literature 18: JP 2006-193612 A
Patent literature 19: JP 2012-30637 A
Patent literature 20: JP 2013-166406 A Non-Patent Literature Non-patent Literature 1: Proceeding of SPIE Vol. 4245, P. 221-227-(2001)
Non-patent Literature 2: Electric Double Layer Capacitor and Power Storage System Nikkan Kogyo Shimbun (1999)
Non-patent Literature 3: Consider Renewable Energy <Goodbye to Nuclear Power Plant> Power Publication (2011)
Non-patent Literature 4: "Wind Force" Save Corn From Ethanolization <Collection of Marine Resources and On-Sea Factory By Wind Power Generation, Power Publication (2007)

BRIEF SUMMARY OF THE INVENTION

Technical Problem

When the base metal element belonging to Group 1, 2 and 13 of the periodic table is dissolved in water, electrons generated and hydrogen ions simultaneously ionized from the water react with each other, producing hydrogen gas. The hydrogen gas annihilates the electrons generated on the base metal (negative electrode) and the current stops to flow to the positive electrode from the negative electrode. This phenomenon is called self-discharge. An object of the present invention is to produce a practical battery which suppresses the self-discharge and to collect a base metal element directly by electrolysis from an aqueous solution in which the base metal element is dissolved.

As an electrolyte used for electrochemical capacitors such as a double layer capacitor, a redox capacitor and a hybrid capacitor, a strong acid or strong aqueous alkali solution is used as disclosed in Non-patent Literature 2. Meanwhile, Patent Literature 16 discloses a double layer capacitor including a first electrode, a second electrode, a first separator and a second separator wound around into a flat shape, in which a winding core is provided to increase the surface pressure of both electrodes to a certain level or more, and the internal resistance is suppressed without increasing the thickness of the separators, thus decreasing the leakage current. Patent Literature 17 discloses that the internal resistance is reduced by changing the material of an electrode of a redox capacitor from nickel or stainless steel to aluminum or copper. Another object of the present invention is to suppress the internal resistance of the electrochemical capacitors, thereby reducing the leakage current.

In the electrolytic refining of metals to deposit only a desired metal on a negative electrode in an electrolyte, those having ionization energy smaller than that of hydrogen and easily affected by water or acid are called base metal elements, including lithium, potassium, barium, calcium, sodium, magnesium, aluminum, titanium, manganese, zinc, chromium, iron, cadmium, cobalt, nickel, tin and lead. Of these, those listed earlier react more violently with water. Those listed later more hardly react with water, but they react with an acid. But, magnesium, aluminum, titanium and the like easily form in the atmosphere, a chemically stable surface oxidation film, and once such a film is formed, thereafter, they become to exhibit high anti-corrosive properties even in water. Particularly, lithium, potassium and sodium of Group 1 of the periodic table, barium, calcium and magnesium of Group 2, and aluminum of Group 13 react violently with water, and thus it is impossible to electrolyze aqueous solutions of salts of these metals. Therefore, these metals are subjected to electrolytic refining by a molten salt electrolytic process, in which a salt of the metal is molten at high temperature and electric current is passed through the molten salt (electrolyte). Another object of the present invention is to find out how to carry out the molten salt electrolysis in an aqueous electrolyte solution.

Generally, batteries which cannot be charged are called primary batteries and those which can be both charged and discharged are called secondary batteries. It is desired that these batteries be able to supply a larger quantity of electricity and higher electromotive force using less active materials. The potential difference between electrodes varies depending on the materials of the electrodes and the ion concentration of the electrolyte. When the electrode potential of hydrogen ion (H+) is set to ±0V, negative electrode materials are:

Li=−3.045V>K=−2.925V>Ba=−2.925V>Ca=−2.840V>Na=−2.714V>Mg=−2.356V>Be=−1.84V>aluminum=−1.67V>Pb=−1.26V>Mn=−1.26V>Zn=−0.76V>nickel=−0.72V>S=−0.55V>Cr=−0.509V>Fe=−0.44V>Cd=−0.4V>Sn=−0.14V>Cd=−0.4V>Co=−0.28V, whereas positive electrode materials are:
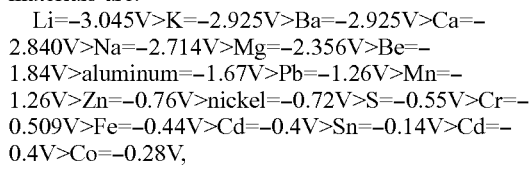
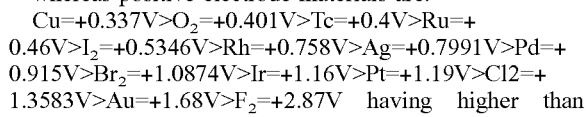
1.3583V>Au=+1.68V>F$_2$=+2.87V having higher than (H=±0V). For the negative electrode of a practical battery, a readily ionizable metal is required, whereas for the positive electrode, a metal having an extremely low ionization tendency or an oxidizing agent (which may be gaseous or liquid) is required. Another object of the present invention is to develop a practical secondary battery using an aqueous electrolyte solution in consideration of the electrode potentials.

In order to prevent mixing of negative electrode products and positive electrode products, such as metals, metal compounds or gases generated in electrolytic refining or electrolysis of the electrolyte in a practical battery, an isolation film (separator) is required. Of the requirements for the isolation film, it is most important that the film can pass ions, but not substances or electrolytes. It is further required that the isolation film have high insulation resistance, be resistant to acids or bases, heat or vibration, mechanically strong, and have a long life. Conventionally, a biscuit-firing material, a solid electrolyte, a filter paper, etc. have been used as an isolation film. Of these, ceramic solid electrolytes including alumina are most suitable for separating an aqueous electrolyte solution and a negative electrode product, but such ceramic solid electrolytes must be placed under high temperature environment in order to function as electrolytes. Of solid materials, a biscuit-firing diaphragm can be used in an aqueous electrolyte solution, but aqueous solution permeates inside of the biscuit firing freely, and therefore moisture cannot be blocked. This is also the case for filter paper. Therefore, another object of the present invention is to develop a film which can block an electrode part and an aqueous electrolyte solution from each other and further, if needed, can control entrance and exit of ions.

Solution to Problem

In solving the conventional problem, the present invention is different from a conventional method in that a water-repellent porous fluororesin film as an isolation film is used as a pressure switch. Conventionally, in an aqueous-solution electrochemical reaction, positive and negative electrodes are installed in an aqueous electrolyte solution. With this structure, it is difficult during an electrochemical reaction to avoid the insulation phenomenon caused by the gas generated at the interface between the aqueous electrolyte solution and the electrode. According to the present invention, the positive electrode and negative electrode inserted to the aqueous electrolyte solution are electrically insulated and isolated from each other with a water-repellent porous membrane, and only when making an electrochemical reaction to occur, the aqueous electrolyte solution is pressurized to fill fine pores in the water-repellent porous membrane with the aqueous electrolyte solution, thus imparting the role of a switch of electrical circuit to change the isolation film of an insulator into an electrically conductive material only at the time of the pressurization. Especially in a practical battery, an aqueous electrolyte solution is sealed in a bag made of a water-repellent porous membrane, and the battery is charged/discharged while pressurizing the water-repellent porous membrane bag, and pressurization is released when accumulating electricity. By the release of pressurization, the electrode and the electrolyte are insulated from each other, thereby avoiding an increase in self-discharge or internal resistance. Moreover, in electrolysis (electrolytic refining) as well, the electrode is not entirely in contact with the aqueous electrolyte solution, chances are low that the products in each electrode dissolve again into the electrolyte, thereby avoiding the insulation phenomenon caused between the electrode and the aqueous electrolyte solution by the gas generated from the electrodes. Further, when a mesh negative electrode is provided in the interface between an aqueous electrolyte solution and oil isolated by a water-repellent porous membrane and the aqueous electrolyte solution is electrolyzed while pressurizing the aqueous electrolyte solution, a negative-electrode product deposits in the oil of the back of the mesh electrode. By using an aqueous base metal salt solution here for the electrolyte, a base metal element, which is a water-disliking metal (Group 1 or 2 element of the periodic table, which reacts with water violently) can be deposited in the oil and further, moreover, heavy liquid separation (gravity classification) can be carried out.

The simplest method of avoiding contact between a compound of a base metal element and water is to use a molten salt of the base metal element. A water-free molten salt is an ideal electrolyte liquid. But, in order to make a molten salt, it is necessary to maintain the salt of the base metal element at a temperature higher than or equal to the melting point. Here, the amount of consumption of heat source therefore is not negligible. Under these circumstances, it is widely popular to prepare a mixed molten salt by mixing with another metal salt to lower the melting point of the salt. Patent Literature 15 shows in its FIG. 2 the relationship between mixed salts and melting points thereof, respectively. The elements in the state of liquid at ordinary temperature, which exist in the nature are only mercury and bromine, and the other elements cannot be liquefied at ordinary temperature. Here, if electrolysis can be carried out while a base metal and a base metal salt aqueous electrolyte solution are isolated from each other, electrolytic refining and a practical secondary battery can be realized. The ultimate object of the present invention is to develop such an isolation film. The necessary and sufficient conditions for the isolation film are that the film has excellent liquid retention properties for the electrolyte solution and low electric resistance. In the present invention, a fluororesin film, which exhibits a water-repellent property to an aqueous solution is adopted to achieve this object. With use of the fluororesin film, not only excellent liquid retention properties for electrolyte, but also zero electric resistance can be maintained. Further, a porous membrane is adopted as the fluororesin film, ions can pass through the inside thereof. That is, if the aqueous electrolyte solution is pressurized by a pressure equal to the water-resistant pressure of the water-repellent porous fluororesin film to, an ion-permeable film can be realized. The application of the water-resistant pressure serves the role of a mechanical switch for zero electric resistance/conduction.

As described, in electrolytic refining or charging and discharging of a practical battery or a capacitor, the aqueous electrolyte solution is pressurized by a pressure equal to the water-resistant pressure, and during storage of charge, it is not pressurized; therefore the liquid retention properties for electrolyte can be maintained. That is, during the storage of charge, the active materials of positive and negative electrodes are in an insulated state, and since the active materials do not react, there is no natural discharge. Further, the material of the isolation film is a fluororesin, and therefore it is excellent in alkali resistance, acid resistance, and chemical resistance even under high temperature (about 80° C.). Also, the film is excellent in mechanical strength, plasticity and heat-resisting property. Moreover, during charging and discharging, a pressure is applied from the aqueous electrolyte solution side, and therefore the film is brought into tight contact with the electrode during the operation. It is considered to be the best method for achieving the object to use a water-repellent porous fluororesin film as a diaphragm as described above.

In the case of a capacitor, if the dielectric is only an insulator such as oil, the internal resistance between the positive and negative electrodes can be neglected, but when dielectrics and electrically conductive materials constitute equivalent circuits electrically combined in parallel or in series, the internal resistance serves as a leakage current. Particularly, in electrochemical capacitors such as an electric double layer capacitor, a redox capacitor and a hybrid capacitor, the increase in internal resistance by the electrolyte inside of an electrode or between electrodes is inevitable. In addition, in the case of an aqueous electrolyte, the liquid may also leak. Thus, in the present invention, in order to prevent the liquid leakage and electric leakage during storage of charge, an aqueous electrolyte solution such as strong acid or strong alkali is enclosed in a bag made of a water-repellent porous fluororesin film, and the bag made of the water-repellent porous fluororesin film is sandwiched by a pair of electrodes consisting of a positive electrode and a negative electrode. During charging and discharging, the water-resistant pressure of the water-repellent porous membrane is applied to bring the surfaces of both electrodes and the aqueous electrolyte solution into contact with each other. Further, an electrically conductive material with voids, such as of metal fibers or carbon fibers, is enclosed together with the electrolyte in the bag of the water-repellent porous fluororesin film. With this structure, during charging and discharging in which the aqueous electrolyte solution is being pressurized, the electric resistance between aqueous electrolyte solutions is small, whereas during accumulating electricity in which the pressurization of the aqueous electrolyte solution is released, the aqueous electrolyte solution in the inner pores of the water-repellent porous fluororesin film is removed to evacuate the inside. Thus, it now functions as a low dielectric, and self-discharge is suppressed. On the other hand, during charging and discharging, the pores of the water-repellent porous fluororesin film are filled with the electrolyte by the pressurization of the aqueous electrolyte solution, transforming it into electrically conductive. Thus, a high charge is transferred with respect to the electric double layer capacitor or the redox capacitor.

Non-patent Literature 1 shows in its FIG. 6 a water-repellent porous fluororesin film (ePTFE) having a diameter of pores of 3 μm and a thickness of 100 μm, with which the difference in pressure (differential pressure) between both sides of the film at the time when the liquid starts to permeate is set as the water-resistant pressure of the film. The literature indicates that when physiological saline (BSS) is used as the solution, the water-resistant pressure is 300 mmHg, above which value, the flow of the physiological saline increases. Here, if the water-repellent porous fluororesin film is regarded as an electrical insulation film, it functions as an insulating film when the differential pressure between both sides of the film is lower than the water-resistant pressure, and the liquid starts to permeate at the water-resistant pressure, the film now functioning as a conducting film. A main point of the present invention is to use the water-resistant pressure of the water-repellent porous membrane as a pressure switch for passing of ions. Especially, since fluororesins exhibit water-repellent properties, the aqueous solution does not enter the pores of the porous film membrane when the differential pressure between both sides of the membrane is less than the water-resistant pressure. Further, the water-resistant pressure may vary depending on the diameter of pores or the salt concentration of the electrolyte. The relationship between the salt concentration of a porous fluororesin membrane (having a diameter of pores of 3 μm) and the osmotic pressure between both sides of the membrane is as follows. That is, the water-resistant pressure in water (salts-free; likewise hereinafter) is 430 mmHg; for a sodium chloride concentration of 10%, 330 mmHg; and for that of 20%, 280 mmHg. Thus, as the electrolytic concentration is higher, the water-resistant pressure becomes lower. The relationship between the salt concentration of a porous fluororesin membrane (having a diameter of pores of 10 μm) and the osmotic pressure between both sides of the membrane is that the water-resistant pressure in water is 130 mmHg, when the sodium chloride concentration is 1%, 7 mmHg, and when 2%, 50 mmHg; thus the water-resistant pressure is low in these cases. Thus, if the ON/OFF operation of the water-resistant pressure of the water-repellent porous membrane is utilized, electrolytic refining and a practical battery in an aqueous electrolyte solution can be realized.

The potential differences of the negative electrode materials of practical batteries are: $Li=Li^+=-3.045V$, $K=K^+=-2.925V$, $Ba=Ba^{2+}=-2.925V$, $Sr=Sr^{2+}=-2.89V$, $Ca=Ca^{2+}=-2.840V$, $Na=Na^+=-2.714V$, $Mg=Mg^{2+}=-2.356V$ and $Al=Al^{3+}=-1.67V$. The specific gravities thereof are Li:0.54, K:0.86, Na:0.97, Ca:1.55, Mg:1.74, Sr:2.54, Al:2.6, Ba:3.51, Fe:7.87, Cu:8.96 and Pb:11.35, respectively. On the other hand, in terms of the current supply amount, aluminum (Al) produces trivalent ions, and magnesium (Mg), barium (Ba), calcium (Ca) and the like produce divalent ions. It is desired in a practical battery that self-discharge, in which the amount of electricity stored decreases gradually with time, should be reduced and the internal resistance be decreased. Further, it is desired in a secondary battery that hydrogen should not be produced during charging, the ohmic resistance and polarization during charging should be low. It is further desired in practicality that the regeneration state after charge and discharge be excellent and be capable for repeated use. However, practically there is no such an electrode material which can satisfy all of these conditions. For example, in the case of a negative electrode material, lithium, which has the highest electromotive force, reacts violently in the presence of water to produce hydrogen, which causes self-discharge and blocks the electron flow.

As a solution to this, the present invention proposes the followings. That is, for convenience, let us now define the theoretical power generation efficiency as VI/g from the ionization potential of the negative electrode (V), the current density=valence (I) and the specific gravity (g/cm$^3$). The metals will be listed in the order of higher VI/g. That is, Li=−3.045×1/0.54=−5.64; Ca=−2.84×2/1.55=−3.66; K=−2.925×1/0.86=−3.40; Na=−2.724×1/0.97=−2.81; Mg=−2.356×2/1.74=−2.71; Al=−1.67×3/2.6=−1.92; Ba=−2.925×2/3.51=−1.67; Sr=−2.89×2/2.54=−1.57; S (negative divalent)=−0.55×2/2.07=−0.53; Mn=−1.1×2/7.42=−0.3; Zn=−0.76×2/7.12=−0.27; Pb=−0.13×2/11.34=−0.23; Cr=−0.51×3/7.2=−0.21; Fe (divalent)=−0.44×2/7.876=−0.11; Sn=−0.14×2/7.28=0.04; and Fe (trivalent)=−0.04×3/7.86=−0.015.

For the positive electrode of a practical battery, a metal having very small ionization tendency or an oxidizing agent (which may be gaseous or liquid) is required. Preferable examples thereof are: as metal, $Sb=Sb^{3+}=+0.2V$, $Bi=Bi^{3+}=+0.28$, $Cu=Cu^{2+}=+0.345$, $Hg=Hg^{2+}=+0.793$, $Ag=Ag^+=+0.808$, $Hg=Hg^{3+}=+0.86$, or as oxidizing gas or liquid, $O_2=OH^-=+0.4V$, $Br_2=Br^-=+1.08V$, $Cl_2=Cl^-=+1.36V$, $F_2=F^-=+2.87$, a permanganate salt, a chromic acid, a nitric acid, a halogen, a peroxide, an oxide, a metal salt, oxygen and sulfuric acid. The specific gravities thereof are: Sb:6.69; Bi:8.8; Cu:8.93; Hg:13.59; Ag:10.5; O2:1.429; $Br_2$ (liquid): 3.14; Cl2:3.21; and $F_2$:1.696. The metals will be listed in the order of higher theoretical power generation efficiency VI/g obtained from the ionization potential of the positive electrode (V), the current density=valence (I) and the specific gravity (g/cm$^3$). That is, $F_2$=+2.87×1/1.696=+1.692; $Cl_2$=+1.36×1/3.21=+0.424; $Br_2$=+1.08×1/3.14=+0.344; O2=+0.4×1/1.429=+0.28; Hg(trivalent)=+0.86×3/13.59=+0.19; Hg=+0.793×2/13.59=+0.117; Bi=+0.28×3/8.8=+0.095; Sb=+0.2×3/6.69=+0.09; Cu=+0.345×2/8.93=+0.077; and Ag=+0.808×1/10.5=+0.077. Therefore, an ideal combination of electrodes which exhibits the highest electromotive force is to use Li for the negative electrode and $F_2$ for the positive electrode and the electromotive force thereof is 5.915V (=+2.87−(−3.045)). As described, fluorine gas ($F_2$=−2.87V) generates the most electromotive force at the positive electrode, but it is highly toxic and therefore, generally, oxygen gas ($O_2$=−0.4V) is used. Here, in an oxygen (air)/base metal battery, the positive electrode thereof is air, and thus capacitance is infinite. But on the surface of the negative electrode of the oxygen/base metal battery, magnesium (Mg), aluminum (Al), zinc (Zn), etc., used for the negative electrode materials are oxidized to form an insulation film on the electrode surface, blocking electron flow. Here, with the use of the water-repellent porous fluororesin film of the present invention, self-discharge can be suppressed, and therefore oxidation of the electrode surfaces can be prevented.

In electrolytic refining, the amount of electricity required to deposit (decompose) 1-g equivalent weight (Eq) of metal as a negative electrode product by electrolyzing an electrolyte is 1 faraday (F)=96500 coulombs (Eq=molecular weight (M)/valence (n) of ion). Since the intensity of current obtained when an electric amount of 1 coulomb flows for one second is defined as 1 A, the amount of electricity of current of A ampere flowing for t seconds (Q coulombs) is: Q=At. Here, the amount (m) of the metal depositing as a negative electrode product is obtained from:

$$m=Eq \times Q/96500=Eq \times At/96500 (m:Q=Eq:96500).$$

The amount of energy accumulated in a practical battery is equivalent to the amount of power required for electrolytic refining, and therefore the current (A) required to deposit m (g) in 1 second is obtained from:

$$A=m \times 96500/Eq \times t.$$

Therefore, the current (A) required to deposit 1 kg in 1 hour is obtained from:

$$A=1000 \times 96500/(Eq \times 3600)=26806/Eq.$$

The discharge capacity per the unit time and unit weight of a practical battery (Weight energy density accumulated in battery (W×time (h)/kg)=voltage (V)×amount of electricity (A×h)/density of electrode (kg)=AVh/kg=Wh/kg) is given by 26806×V×n/M [Wh/kg] (V: electromotive force, M: mass number of reactant, n: valence). The discharge capacities (Wh/kg) by combinations of various types of base metal negative electrode materials and various types of gas positive electrode materials (oxygen or halogen) obtained when this formula is applied to a practical battery are presented in FIG. 1. Note that the discharge capacities in the case where the gas weight of the positive electrode material is neglected (mass being zero) are parenthesized in the following list. The base metal/halogen batteries, in particular, exhibit high attractive electromotive forces and therefore are preferable. For example, the following data can be obtained: $Li/Cl_2$ (16,888)>$Li/Br_2$ (15,815)>$Li/I_2$ (13,709)>$Al/F_2$ (13,522) >$Al/Cl_2$ (9,025)>$Mg/Cl_2$ (8,185)>$Na/F_2$ (6,515)>$CaBr_2$ (5,254)>$Ca/Cl_2$ (5,112)>$Na/Br_2$ (4,429)>$K/F_2$ (3,980)>$Na/I_2$ (3,788)>$Mg/Br_2$ (3,784)>$Mg/I_2$ (3,177). But, here, halogen gas needs to be handled, which accompanied by danger and requires cautions in handling. On the other hand, in the case of base metal/oxygen, the air can be used as the positive electrode. Therefore, it is possible to provide a safe and light battery. The batteries in which oxygen is used for the positive electrode will now be listed in the order of higher discharge capacity: $Li/O_2$ (11,680)>$Be/O_2$ (6,672)>$Al/O_2$ (6,165)>$Mg/O_2$ (6,067)>$Ca/O_2$ (4,343)>$Na/O_2$ (3,636).

Thus, firstly, the present invention provides, according to a first aspect, an electrochemical reactor comprising a positive electrode with a first major surface and a second major surface on an opposite side to the first major surface; a negative electrode with a first major surface and a second major surface on an opposite side to the first major surface, wherein the positive electrode and the negative electrode faces each other by their first major surfaces and arranged apart from each other to define a space therebetween; an electrically conductive liquid and/or dielectric liquid filling the space; a first (solution) isolation member (isolation means) provided on the first surface of the positive electrode to isolate the positive electrode from the liquid, wherein the first isolation member comprises a first liquid-repellent porous membrane having a plurality of pores; a second (solution) isolation member (isolation means) provided on the first surface of the negative electrode to isolate the negative electrode from the liquid, wherein the second isolation member comprises a second liquid-repellent porous membrane having a plurality of pores; and a pressure-applying member which pressurizes the liquid to fill the plurality of pores of the first and second liquid-repellent porous membranes with the liquid, thereby causing an electrochemical reaction involving the positive electrode and the negative electrode.

In one embodiment of the present invention, the liquid-repellent porous membrane can be formed of a fluororesin, polypropylene resin, or polyethylene resin, and the liquid is an aqueous electrolyte solution, which can be pressurized by a pressure equal to the liquid-resistant pressure of the liquid-repellent porous membrane.

In another embodiment, the liquid-repellent porous membrane is formed of a fluororesin, and the liquid is an oil, which can be pressurized by a pressure equal to the liquid-resistant pressure of the liquid-repellent porous membrane.

In a still another embodiment, the liquid-repellent porous membrane is made of porous carbon, and the liquid may be a molten salt electrolyte.

Further, in an embodiment of the present invention, the first liquid-repellent porous membrane and the second liquid-repellent porous membrane are combined together to constitute a sealed container. The inside of the sealed container may correspond to the space. Further, in another embodiment, the first liquid-repellent porous membrane and the second liquid-repellent porous membrane may be films separate from each other. Further, the positive electrode and the negative electrode may be provided in a positive electrode chamber and a negative electrode chamber, respectively, whose openings opposing each other are closed by the respective liquid-repellent porous membranes.

The electrochemical reactor of the present invention may be an electrolytic device, a primary battery, a secondary battery or a capacitor.

In the electrochemical reactor, when a predetermined pressure is applied to the conductive or dielectric liquid, the liquid enters the pores of each water-repellent porous membrane to bring each electrode into contact with the liquid, thereby causing a desired electrochemical reaction (in which the positive electrode and the negative electrode involve) to occur. When the pressure is released, the contact between each electrode and the liquid is cancelled. That is, the isolation film functions as an ON/OFF switch to activate/deactivate the electrochemical reaction by applying or not applying the predetermined pressure.

The principle of the ON/OFF switch of the water-repellent porous membrane (isolation film) is shown in FIG. 2. That is, a sealed container 1 made from a water-repellent porous membrane 11 is interposed between a negative electrode chamber 3 accommodating a negative electrode and a negative electrode chamber 4 accommodating a positive electrode, and a aqueous electrolyte solution 14 is accommodated in the sealed container 1. Here, as shown in FIG. 2(A), when the aqueous electrolyte solution 14 is pressurized with a pressure-applying member 6 (for example, cylindrical weight) by a pressure less than the water-resistant pressure of the water-repellent porous membrane 11 (in the figure, not pressurized), the electrolyte solution does not enter the pores of the water-repellent porous membrane 11, and therefore an electrical insulation state is established for a voltmeter VM to indicate zero. On the other hand, as shown in FIG. 2(B), when the aqueous electrolyte solution 14 is pressurized with the pressure-applying member 6, the aqueous electrolyte solution enters the pores of the water-repellent porous membrane 11, which makes the voltmeter VM to be a positive side, exhibiting an electromotive force.

In a limited field of the electric field, the water-repellent porous membrane can be used for electrolytic devices, practical batteries, or capacitors (see FIG. 3A and FIG. 3B). In the electrochemical reactor of the present invention (an electrolytic device, a practical battery device or a capacitor), a charge/discharge is carried out by applying a predetermined pressure (liquid-resistant pressure) to the liquid, and it is stopped under a pressure less than the predetermined pressure. In this manner, the liquid-repellent porous membrane (isolation film) allows the pores to pass the solution and ions by applying a pressure equal to the liquid-resistant pressure to the liquid, and thus functions as a switch to create an electrically conductive state, that is, an electronic ON/OFF switch.

Here, the water(liquid)-resistant pressure of the water (liquid)-repellent porous membrane is the differential pressure between the pressure on an injection side (primary side) of the water(liquid)-repellent porous membrane and that of an exit side (secondary side) and is the minimum differential pressure by which liquid can enter the pores of the porous membrane. A liquid is on one side and a gas or a liquid is on the other side. The liquid may be an aqueous solution of an electrolyte or a nonelectrolyte, a dielectric liquid such as an oil or pure water, or a base metal element-based molten salt solution. The gas may be hydrogen, oxygen, gaseous chlorine or the like generated at a negative electrode or a positive electrode by electrolysis of an aqueous solution, or hydrogen injected into a molten salt.

Liquids can be classified into electrically conductive materials and dielectric materials by the electrical properties. The conductive liquids include aqueous electrolyte solutions and molten salt electrolytes and the aqueous electrolyte solutions are used for electrolysis, batteries or electrochemical capacitors. In this case, the liquid-repellent porous membrane can be formed from a fluororesin, a polypropylene resin or a polyethylene resin, and as described above, the membrane functions as an electronic switch. When the solution is a molten salt electrically conductive material, a porous carbon film is used to function as both isolation film and negative electrode of a molten salt, and metal hydride is produced in the process in which the anions of the hydrogen gas migrates from the negative electrode side to the positive electrode side of the molten salt. On the other hand, the dielectric liquids include oil-based liquids and aqueous liquids, and the oil-based liquids can be used for collection of negative electrode products, recovery of products from a member functioning as both oil capacitor and negative electrode, or for an oil-based capacitor. In collection of negative electrode products in particular, a Group 1 element of the periodic table is separated from water, and subjected to gravity classification in an oil, whereas in collection of oil capacitors and negative electrode products, a charge is given to the oil side by making the interface of the aqueous electrolyte solution and the oil into a negative electrode surface, in which the negative electrode products are subjected to gravity classification on the oil side.

When applied to only capacitors, nitrobenzene and oil, which have high dielectric constant, are used as oil capacitors, whereas pure water, formic acid and the like are used as aqueous capacitors. A capacitor is of such a structure that a positive electrode plate, a water-repellent porous membrane, a dielectric solution, a water-repellent porous membrane and a negative electrode plate are arranged in this order. For charging/discharging, the dielectric solution is pressurized at liquid-resistant pressure to the water-repellent porous membrane to fill the inside of the water-repellent porous membrane with the dielectric solution. In storage of charge, the fluid pressure of the dielectric solution is released to free the dielectric solution inside the water-repellent porous membrane, and the water-repellent porous membrane itself functions as a low dielectric constant capacitor. Thus, when accumulating electricity, a three serial capacitor structure in which a high dielectric constant capacitor is sandwiched between two low dielectric constant capacitors is taken, whereas a single capacitor structure is taken when charging and discharging.

On the other hand, when the isolation film is a solid dielectric which exhibits oil-repellent properties, and especially it is a fluororesin, oil should be mixed into the aqueous solution. Since fluororesin exhibits lipophilic properties, the oil is adsorbed on the surface of the fluororesin. By utilizing this property, a little amount of oil is mixed into the aqueous dielectric to form an ultra-thin oil layer on the dielectric solution side of the fluororesin, and further an electrode is brought into tight contact with the opposite side of the fluororesin to form a high dielectric. Thus, an electrochemical reactor using an analog switch to control electron transfer between electrodes can be provided.

In the electrochemical reactor of the present invention, when the water-repellent porous membrane is made from a polymer resin, a hydrophilic group or a water-repellent group is introduced to the surface and pore wall of the existing porous membrane, or an appropriate material is selected from those having different pore diameters, or the salt concentration or liquid temperature of the aqueous electrolyte solution is changed, or a potential is applied between these water-repellent porous membranes, so as to change the value of the water-resistant pressure of the film. Thus, an aqueous electrolyte solution which can pass a water-repellent porous membrane according to the hydraulic pressure of the aqueous electrolyte solution can be obtained, or the quantity of ion can be controlled.

In order to increase the water-resistant pressure, it suffices if the diameter of the pores of the water-repellent porous membrane is enlarged. However, if the diameter of the pores is enlarged, the mechanical strength of the membrane is weakened. Here, if the fluororesin which exhibits water-repellent properties and oil-repellent properties is reformed into hydrophilic, the wettability with water increases to lower the water-resistant pressure. However, if both surfaces of the fluorine-based porous membrane are reformed into hydrophilic, the film increases its wettability with respect to both an aqueous solution as well as an electrode, damaging the retention of electric insulation. Patent Literatures 12, 13 and 14 disclose a method of manufacturing a fluorine-based water-repellent porous membrane by irradiating a fluorine-based water-repellent porous membrane with an excimer laser beam in the presence of a compound containing an atom having a bond energy of 128 kcal/mol or more, and a hydrophilic group. Patent Literature 15 discloses a method of imparting wettability to an inner pore wall by substituting the inner holes of a fluorine-based water-repellent porous membrane with a hydrophilic group by the photoreaction of ultraviolet radiation. Non-patent Literature 1 discloses that the water-resistant pressure of a water-repellent porous fluororesin film having a pore diameter of 33 μm is 1500 torr, but the water-resistant pressure is dropped to 20 torr by photo-reforming of the inside of pores into hydrophilic. Further, Non-patent Literature 1 indicates that the water-resistant pressure lowers if the salt concentration of an aqueous electrolyte solution increases. Patent Literature 18 discloses the fact that the water-resistant pressure lowers if the temperature of the aqueous electrolyte solution is increased, and also electro-wetting which enhances the hydrophilic properties by applying electric potential between these water-repellent porous membranes. Thus, the quantity of ion which can penetrate the water-repellent porous membrane can be controlled in an analog fashion according to the hydraulic pressure of the aqueous solution.

In the electrochemical reactor of the present invention, according to one embodiment, a liquid-repellent porous membrane (isolation film) is placed in an open container such as sea, salt lake, hot-spring, mineral spring ponds, aqueous solution waste storage ponds, thermokeeping bath, reservoirs, water supplies, pools, open containers including a large-sized tank, sealed containers such as bags, tubes and small containers or sealed containers in which a smaller sealed container is inserted. Here, the aqueous electrolyte solution in the space permeates from the water-repellent porous membrane by pressurization and the electrochemical reaction of the aqueous electrolyte solution takes place between a positive electrode and a negative electrode.

By pressurizing the aqueous electrolyte solution in the isolation tools with a pressure-applying member, the aqueous electrolyte solution permeates from the water-repellent porous membrane to electrically couple the positive electrode and the negative electrode, thus inducing the electrochemical reaction of the aqueous electrolyte solution to occur. The isolation tool can be classified into a sealed container and an open container, as shown in FIG. 4.

The chemical reactor (FIG. 4(A)) using a sealed container refers to a bag, a tube, a small container or the like, a surface of which contacting a pair of positive and negative electrodes is a water-repellent porous membrane. A solution of electrolyte or dielectric is sealed in this sealed container and an arbitrary outer surface is directly pressurized (FIG. 5(A)) with a pressure-applying member 6 as shown in FIG. 5. Or the solution in the sealed container is pressurized with a cylinder (syringe) 6, a rubber syringe, a pipette 7 or the like, manually or with an electric device, or with a pressurizing device with a ratchet 8, or the solution is pressurized by a water tank 9 placed at such a high level that can create a pressure head equal to the water-resistant pressure, and connected to the container with a connection tube 6, and setting the potential head (h) 10 of the electrolyte solution (FIG. 5(B)).

As shown in FIG. 4(B), an open container 11 refers to sea, salt lake, hot-spring or mineral spring, filled with a huge quantity of electrolyte solution, a storage pond storing aqueous solution waste or electrolyte, or a tank such as a reservoir, a thermokeeping bath, a water pond, service water or a pool. Generally, the hydraulic pressure rises by about 1 atmosphere as the depth from the water surface of the sea or lake increases by 10 meters. Since this is equivalent to the pressure of the solution at the depth, the isolation tool of this region can be regarded as an open container. Here, an electrode product collecting chamber in which a pair of positive electrode and negative electrode are arranged while interposing a water-repellent porous membrane is sunk in the huge quantity of electrolyte solution to a certain depth where a hydraulic pressure equal to the water-resistant pressure of the water-repellent porous membrane can be obtained while maintaining a regular interval, and the aqueous electrolyte solution is directly electrolyzed.

The chemical reactor which uses a sealed container in an open container has, as shown in FIG. 4(C), a structural body in which a sealed container 1 is inserted in an open container 2, so that the sealed container 1 is pressurized with the hydraulic pressure within the open container 2 to carry out electrolysis between the positive and negative electrode chambers tightly attached to the sealed container 1. The sealed container 1 is provided with at least one water-repellent porous membrane a in addition to the two water-repellent porous membranes attached to the pair of electrodes. Further, in the sealed container 1, an aqueous solution having high dielectricity of sulfuric acid or caustic soda (sodium hydroxide), or the like is placed, and water or an aqueous electrolyte solution which has passed the water-repellent porous membrane a by the hydraulic pressure of the open container is supplied to carry out electrolysis in the sealed container 1. In place of this open container, a double container structure in which the sealed container 1 is inserted into a large-sized sealed container may be used, in which the sealed container 1 is pressurized with the hydraulic pressure in the large-sized sealed container to carry out electrolysis between the positive and negative electrodes tightly attached to the sealed container 1. With the hydrogen producing device having the double container structure, hydrogen can be produced efficiently from non-electrolytic water such as sea water, it is also possible to produce hydrogen by putting the chemical reactor into freshwater of a lake or a swamp, or a low-concentration aqueous electrolyte solution such as salt water or a mineral spring, which is another feature of the present invention. Or an electrochemical reactor comprising a pressure-applying member to pressurize a gas filled inside of the sealed container of the liquid-repellent porous membrane to pressurize the gas to permeate into a molten salt from the pores of the liquid-repellent porous membrane.

Next, the method of pouring an aqueous electrolyte solution into the hollow sealing bag made of a water-repellent porous membrane will be described. The material for the water-repellent porous membrane is, for example, fluororesin, polypropylene resin, polyethylene resin or the like, and of these, fluororesin has the highest chemical resistance and heat-proof temperature. As shown in FIG. 6, examples of the method of filling the inside of the hollow sealed bag 1 made from the water-repellent porous membrane 11 with the aqueous electrolyte solution 14 are as follows. That is, the aqueous electrolyte solution 14 is directly injected into a hollow bag with a liquid injection cylinder (syringe) 6 (FIG. 6(A)). Or utilizing the water-repellent porous membrane 11 which does not pass water but passes gas, the hollow sealed bag 1 in which a solute 15 such as a chemical is sealed in advance is placed in a water vapor atmosphere to induce a hydrolysis and a dissolution reaction with the solute, thereby reserve water inside, or a hollow sealed container in which a solute such as a chemical is sealed in advance is inserted into a sealed container while the inside of the hollow sealed bag is opened to atmosphere by a communicating pipe, and water in the sealed container is pressurized with a hydraulic pressure equal to the water-resistant pressure, to inject water into the sealed container for hydrolysis, thereby producing an aqueous electrolyte solution (FIG. 6(B)). Or while one water-repellent porous membrane 11 of a hollow sealed bag is being suctioned from a suction opening 94 under a negative pressure lower than the water-resistant pressure with a vacuum pump, the aqueous electrolyte solution 14 is injected into the container from a water-repellent porous membrane 11 on the other side, to reserve the aqueous electrolyte solution 14 in the sealed container 1 in the sealed container (FIG. 6(C)). Or an alcohol 13 is applied one wall of a hollow sealed container and a solvent or the aqueous electrolyte solution 14 is allowed to enter from the alcohol-applied surface. Thereafter, the system is let stand or heated to evaporate the alcohol, thereby reserving the aqueous electrolyte solution in the bag (FIG. 6(D)). As to the alcohol-applying method, Non-patent Literature 1 and Patent Literature 12 disclose that the surface tensions of water, fluororesin and methyl alcohol are 72.3 dyn/cm, 28.5 dyn/cm and 22.3 dyn/cm, respectively. These literatures also indicate that in the case of a porous fluororesin, water, which has a surface tension higher than that of the fluororesin, does not permeate the pores of the porous material, but methyl alcohol, which has a surface tension lower than that of the fluororesin permeates the pores. Further, these also mentions that since alcohol has high water affinity, if water is placed on a porous fluororesin in which alcohol has been made to permeate, only when the alcohol exists, water permeates the pores of the material.

As shown in FIG. 7, in the electrochemical reaction of an aqueous electrolyte solution, a pair of a positive electrode and a negative electrode is formed of electrode plates in the case of batteries or capacitors, or from electrode chambers comprising means to collect electrode products in the case of electrolytic devices.

For the electrodes subjected to a battery, if the electrode plates are a negative electrode of an amphoteric element, Mg or a metallic element having an ionization tendency higher than that of hydrogen excluding those of Group 1 or 2, and a positive electrode of oxygen, graphite fluoride, or a metallic element having an ionization tendency lower than that of hydrogen, both electrodes are bare electrodes exposed to outside air. Or if the negative electrode is of an element from Group 1 or 2 and the positive electrode is of a halogen or a halide compound, both electrodes can be made into the electrode chambers shielded from the outside air.

For the electrodes subjected to electrolysis, the electrode chamber is classified into a gas-permeable electrode chamber, a base metal collecting electrode chamber filled with oil, and an acidic/basic aqueous solution collecting electrode chamber filled with water. When the electrode product is a gas, the insides of both electrodes are formed into a porous electrode exhibiting a texture of mesh, fibers, porous material or grains of a metal or carbon, or a gas-permeable electrode chamber having such a structure that the back surface of the porous electrode includes a gap. When the electrode product is an element from Group 1, 2 or 13, the negative electrode is formed into an electrode chamber structure filled with oil, or an electrode chamber with the porous electrode whose pores or gap at the back surface thereof are filled with an oil to subject negative electrode products to heavy liquid separation, or an electrode chamber filled with an oil (oil-filled electrode chamber) provided with a electrode plate at the back of the oil to be used as a dielectric capacitor and also a power storage medium. Or when the electrode product is made into an acid aqueous solution by ionic reaction with water, such a structure is taken that the front side of the positive electrode plate is filled with water to which dilute acid is added in advance. When the electrode product is a basic aqueous solution, the structure of an electrode chamber (water-filled electrode chamber) is taken, in which the front of the negative electrode plate is filled with water to which dilute alkali is added in advance, and also such a structure is taken that the water-filled electrode chambers of both electrodes are provided with an inlet for supplying water and an outlet for feeding a produced acidic or basic aqueous solution, and with a produced gas collecting inlet at an upper portion thereof, or that water is circulated in the pores of the porous electrode made of carbon or in the gap at the back surface to collect a gaseous halogen, sulfite or nitrous acid by absorbing it into water.

When the electrodes are subjected to a capacitor, positive/negative electrode plates are bare electrodes of a single plate type which sandwiches an oil or aqueous dielectric both via water-repellent porous membranes, or an electric double layer type, in which organic molecules are adsorbed on the surface of an activated carbon electrode, or redox type electrodes of, for example, a metal oxide, an electrically conductive polymer or activated carbon, in which the redox electrodes isolated from each other by a water-repellent porous membrane are short-circuited with electrically conductive fibers filled with electrolyte. With the redox structure, a high charge can be stored in the oxide films of both the positive/negative electrode plates. Further, for storing an acidic or basic aqueous electrolyte solution in a sealed container (bag) made of a water-repellent porous membrane, electrically conductive fibers are enclosed, thus making it possible to reduce the internal resistance.

In one embodiment, the electrochemical reactor can be represented by an equivalent circuit shown in FIG. 8. This circuit is named the "Murahara circuit". As shown in the equivalent circuit of FIG. 8, this electrochemical reactor electrolyzes an aqueous electrolyte solution by using the interface between an aqueous electrolyte solution and an oil as the negative electrode, to deposit cathode products in the oil layer and subject them to heavy liquid separation (gravity classification). The reactor includes a virtual negative electrode 19 to electrolyze the aqueous electrolyte solution 14 having an electric resistance (R) to deposit base metal in the oil-filled electrode chamber 16. The virtual negative electrode 19 is practically a border between the oil side and the water side, and this interface can be established when the oil side and the water side are perpendicular to the earth's axis, otherwise, a water-repellent porous membrane is used. This water-repellent porous membrane 11 is taken as a switch (S), and only when the pressure of the aqueous electrolyte solution equal to the water-resistant pressure is applied to the water-repellent porous membrane 11, the switch (S) is short-circuited to carry out electrolysis. In more detail, the interface between the oil of the oil layer and the aqueous electrolyte solution which constitute the oil-filled electrode chamber 16 is assumed as the negative electrode 19. That is, an electrical circuit including the oil layer as the oil capacitor $(C_1+C_2)$ and the aqueous electrolyte solution 14 as a water rheostat (R) uses the interface between the oil layer and the aqueous electrolyte solution as the negative electrode 19 of the oil capacitor and comprises an intermediate electrode 18 between the positive electrode 17 and the negative electrode 19 of the oil capacitor, to form a dielectric 1 ($C_1$) between the positive electrode 17 and the intermediate electrode 18 and a dielectric 2 ($C_2$) between the intermediate electrode 18 and the negative electrodes 19.

One of the features of the present invention here is that the interface between the oil layer and the aqueous electrolyte solution functions as a negative electrode. That is, only when a voltage (E) 20 is continuously applied to the dielectric 1 ($C_1$) between the positive electrode 17 and the intermediate electrode 18, and also the switch (S) of the water-repellent porous membrane 11 is short-circuited in the state that the positive electrode 17 of the oil capacitor is used as the positive electrode of the aqueous electrolyte solution 14, a serial circuit is formed to move the charge stored in the oil capacitors $(C_1+C_2)$ to the aqueous electrolyte solution 14 to give the voltage 20 higher than or equal to the decomposition voltage, thus subjecting the negative electrode products to heavy liquid separation in the oil layer in the dielectric 2 ($C_2$). Here, the dielectric 1 ($C_1$) may be substituted by a fixed capacitor to give charge to the dielectric 1 ($C_1$), and simultaneously, the aqueous electrolyte solution 14 as water rheostat (R) may be connected between the negative electrode 19 of the dielectric 2 ($C_2$) and the positive electrode 16 of the dielectric 1 ($C_1$) to give the voltage 20 higher than or equal to the decomposition voltage, thereby subjecting the negative electrode products to heavy liquid separation in the oil layer in the dielectric 2 ($C_2$).

FIG. 9 is a conceptual diagram showing an oil capacitor which uses the interface of an oil side and an aqueous electrolyte solution side as the negative electrode. FIG. 9(A) is a diagram showing a structure of a virtual negative electrode using a water-repellent porous membrane. Note here that the interface of the oil and the aqueous electrolyte solution is not influenced by the earth's axis. FIG. 9(B) is a diagram showing a structure of such a case that the virtual negative electrode has a plane vertical to the earth's axis and the specific gravity of the oil is less than one. FIG. 9(C) is a diagram showing a structure of such a case that the virtual negative electrode has a plane vertical to the earth's axis and the specific gravity of the oil exceeds one.

As shown in FIG. 9(A), in the case where the virtual negative electrode (the interface between the oil side and the aqueous electrolyte solution side) 19 is inclined to the earth's axis at an arbitrary angle, the virtual negative electrode 19 is formed only when the water-repellent porous membrane 11 is inserted between the oil side and the aqueous electrolyte solution side 19 to pressurize the aqueous electrolyte solution 14. If the virtual negative electrode 19 is a plane vertical to the earth's axis, the water-repellent porous membrane 11 is not necessarily required. Or, if the density (specific gravity) of the oil is lower than that of the aqueous electrolyte solution 14 (the specific gravity being less than one), an oil layer 23 is formed in an upper portion of the aqueous electrolyte solution 14. If the density of the oil is higher than that of the aqueous electrolyte solution 14 (the specific gravity being more than one), the oil layer 24 is formed in a lower portion of the aqueous electrolyte solution 14. In addition to the above, the charge 20 is given to the dielectric 1 ($C_1$ in FIG. 8(A)) and simultaneously, the aqueous electrolyte solution 14 is connected between the negative electrode 19 of the dielectric 2 ($C_2$ of FIG. 8(A)) and the positive electrode 17 of the dielectric 1 to give the voltage 20 higher than or equal to the decomposition voltage, thus subjecting the negative electrode products to heavy liquid separation in the oil in the dielectric 2 ($C_2$ of FIG. 7(A)), to be unloaded from a collecting port 26.

In one embodiment, a pair of positive and negative gas-permeable electrode chambers can be sunk into sea or a salt lake, which is of a low-concentration aqueous electrolyte solution, at a level of the head position under the sea surface, and thus it is possible to produce hydrogen and oxygen or chlorine directly from sea water (hydrogen-producing apparatus, see FIG. 10). In general, the hydraulic pressure increases by about one atmosphere each time the object sinks from sea level or the water surface by 10 m. When this natural phenomenon is used and the air-permeable positive and negative electrode chambers are sunk to a depth of the hydraulic pressure equivalent to the water-resistant pressure of the water-repellent porous membrane, there will be no necessity for artificially applying the pressure. For example, when a pair of positive and negative electrode chambers, whose electrode surfaces are slightly separated from each other, is sunk to the depth where the water-resistant pressure of the water-repellent porous membrane under sea surface is obtained, to apply an electric potential to both electrodes, hydrogen, oxygen, or chlorine can be produced. Therefore, the low-concentration aqueous electrolyte solution (aqueous sodium chloride solution) 14 of an open container 2 such as sea or salt lake is injected into a pair of negative electrode chamber 3 and a positive electrode chamber 4 through the water-repellent porous membrane 11, as shown in FIG. 10(A). With the gas-permeable electrode chambers 3 and 4, salt water is electrolyzed to produce hydrogen at the negative electrode chamber 3 and oxygen or chlorine at the positive electrode chamber 4. Here, each of the positive and negative electrodes is made of a porous electrode of a metal or carbon having a mesh texture, fibrous state, or grain form, and the topmost portion of each of the gas-collecting electrode chambers 3 and 4 comprises a produced-gas collecting hose 12, thus constituting a pair of electrode chambers 3 and 4, which are set close to each other in the aqueous electrolyte solution (sea water) 14. This pair or a group of connected pairs of positive and negative electrode chambers are set under the sea surface, where the hydraulic pressure equal to the water-resistant pressure of the water-repellent porous membrane is obtained, and electrolysis is carried out only by applying a potential between both electrodes to separately collect hydrogen at the negative electrode chamber and oxygen or chlorine at the positive electrode chamber. In the present invention, an electrode is not directly inserted into an aqueous electrolyte solution, and therefore the insulating state between the electrode and the electrolyte is not created by an electrode product. Further, over the water-repellent porous membrane as the border, the pressure on the electrolyte side is higher than that of the electrode product side. With this structure, the collecting efficiency of the electrode product is high. If the sealed container 1 is substituted for the open container 2, it can be used also on land as shown in FIG. 10(B). The aqueous electrolyte solution (salt water) 14 of the sealed container 1 is pressurized with a pressure-applying member 6 or the water tank 9 installed at the head position 10 communicated via a communicating tube 5, sea water, concentrated sea water or a water-added electrolyte is directly electrolyzed, to separately collect hydrogen gas at the negative electrode chamber 3 and oxygen or chlorine gas at the positive electrode chamber 4.

In one embodiment, freshwater is injected into a concentrated aqueous electrolyte solution sealed in a hermetically sealed container through a water-repellent porous membrane (for freshwater permeation) 27 from an outer wall of the sealed container, to carry out electrolysis, thus making it possible to directly produce hydrogen and oxygen or chlorine at high efficiency (see FIG. 11).

As shown in FIG. 11(A), a hydrogen-producing apparatus 30 comprising a sealed container formed of a water-repellent porous membrane filled with a high-solubility and high-conductivity aqueous electrolyte solution (high-concentration aqueous electrolyte solution), such as dilute sulfuric acid or a caustic soda aqueous solution is sunk in an open container 2 such as freshwater lake, pond, sea water or hot-spring, and thus while a low-concentration aqueous electrolyte solution 14 such as freshwater, sea water, hot spring water, or high-temperature wastewater is injected into the sealed container 1 from a water-repellent porous membrane 27 for injecting aqueous solution attached thereto, the aqueous solution is electrolyzed to produce hydrogen. In the state where a high-concentration aqueous electrolyte solution such as dilute sulfuric acid, a caustic soda aqueous solution or the like is enclosed in the sealed container 1, the low-concentration aqueous electrolyte solution 14 is supplied into the sealed container continuously from the water-repellent porous membrane (for freshwater permeation) 27 attached to the outer wall of the sealed container 1, thereby producing hydrogen continuously. Note that in order to make two kinds of aqueous electrolyte solutions of different concentrations between an interior and an exterior of the sealed container 1 to permeate the pores of the water-repellent porous membrane under the same water-resistant pressure, different types of water-repellent porous membranes a (11) and b (27), with the size of pores being larger in the water-repellent porous membrane b (27) than in the membrane a (11), should be selected, if they may differ. Or if the water-repellent porous membranes a (11) and b (27) are of the same type, pore walls of the side of water-repellent porous membrane b (27) brought into contact with the low-concentration aqueous electrolyte solution are substituted by a hydrophilic group to promote the wettability with water, thereby enabling both the low-concentration aqueous electrolyte solution and high-concentration aqueous electrolyte solution to permeate the water-repellent porous membrane a (11) and the water-repellent porous membrane b (27) at the same hydraulic pressure or pressure values close to each other. If the water-repellent porous membranes a (11) and b (27) are of the same type, the simplest method is that the hydraulic pressure on the side of the low concentration aqueous electrolyte solution is made positive (high) or the pressure on the outlet side of the water-repellent porous membrane a in which the high-concentration aqueous electrolyte solution is contained with pressure is made negative (suction). The negative pressure means to suction the gas generated by gas-permeable electrode chambers such as the negative electrode chamber 3 and the positive electrode chamber 4 coming into contact with the water-repellent porous membrane a (11) with a gas-transportation vacuum pump within a range that the differential pressure between the hydraulic pressure applied to the low-concentration aqueous electrolyte solution and the pressure of the generated gas in the gas-permeable electrode chamber on the exit side of the water-repellent porous membrane a (11) is higher or equal to the sum of the water-resistant pressure of the water-repellent porous membrane b (27) and the water-resistant pressure of water-repellent porous membrane a (11). During electrolysis, a great amount of gas is generated, and therefore it is necessary to collect generated gas and deal with gas pressure simultaneously in the gas-permeable electrode chamber. Therefore, it is desirable to provide a pressure regulating valve 93 in a stage prior to a produced-gas collecting port 12 of the gas-permeable electrode chambers, namely, the electrode chamber 3 and the positive electrode chamber 4.

Usually, the water-resistant pressure of a water-repellent porous membrane will become low, as the concentration of the electrolyte generally becomes high as shown in the relationship of the water-resistant pressure and salt concentration of the porous fluororesin film of FIG. 28.

In particular, in the case where an aqueous electrolyte solution obtained as the low-concentration aqueous electrolyte solution 14 or freshwater 88 or the like is mixed with a high-concentration aqueous electrolyte solution such as dilute sulfuric acid or dilute alkali in the sealed container 1 through the water-repellent porous membrane b (27) is electrolyzed between the negative electrode chamber 3 and the positive electrode chamber 4 brought into contact with the water-repellent porous membrane a (11) to generate gas in the gas-permeable electrode chambers, and thus a pressure (Pg) is created due to the gas in each gas-permeable electrode chamber, when the differential pressure between the hydraulic pressure $P_{lb}$ applied to the water-repellent porous membrane b (27) by the low-concentration aqueous electrolyte solution 14 and the hydraulic pressure $P_{la}$ applied to the water-repellent porous membrane a (11) by the high-concentration aqueous electrolyte solution is the water-resistant pressure $P_{lba}$ of the water-repellent porous membrane a (11), and also the differential pressure between the hydraulic pressure $P3_{lag}$ of the high-concentration aqueous electrolyte solution and the pressure (Pg) within the gas-permeable electrode chamber is the water-resistant pressure $P_{lag}$ of the water-repellent porous membrane a (11), the relationships: $P_{lb}-P_{la} \geq P_{lba}$ and $P_{la}-Pg=P_{lag}$ must be satisfied simultaneously. In order words, in order to satisfy $P_{lb}-Pg \geq P_{lba}+P_{lag}$, the hydraulic pressure $P_{lb}$ applied to the low concentration aqueous electrolyte solution 14 should be high (positive pressure) or the pressure (Pg) in the gas-permeable electrode chamber to maintain should be negative by suctioning with a vacuum pump through a pressure regulating valve 93. Thus, the total of the water-resistant pressures of all the water-repellent porous membranes regulates the hydraulic pressure $P_{lb}$ applied to the beginning of the reaction system and the gas-pressure cable Pg applied in the end to have an electrolysis, thus producing hydrogen, oxygen, or chlorine. In practice, the same water-repellent porous membranes are used for the water-repellent porous membranes a (11) and b (27), and the hydraulic pressure $P_{lb}$ applied to the low concentration aqueous electrolyte solution 14 is made a positive pressure, or the pressure Pg in the gas-permeable electrode chamber is made negative. With such a simple operation, the electrolysis can be carried out to produce hydrogen directly from within sea water or lake. More specifically, That is, the sealed container 1 in which s high-concentration aqueous electrolyte solution such as dilute sulfuric acid or dilute alkali is enclosed is inserted to the open container 2, which is the sea or lake where a low-concentration aqueous electrolyte solution exists, and the sealed container 1 is sunk to a pressure head position, where electrolysis is carried out continuously.

This method can be used on the land as shown in FIG. 11(B). The sealed container 1 is inserted to a large-sized sealed container 29, and the hydraulic pressure of tap water 28 is pressurized higher than or equal to the water-resistant pressures of the water-repellent porous membrane 11 and the water-repellent porous membrane (for freshwater permeation) 27 while water supply, thereby producing hydrogen continuously. In place of tap water, a container filled with freshwater or sea water or a thermokeeping bath of hot spring is used, and while pressurizing at a pressure higher than or equal to the water-resistant pressure of the water-repellent porous membrane, water can be supplied with pressure by means of mechanical pressurization or through a communicating tube from a head position. What is important here is to equalize or approximate the water-resistant pressure of the water-repellent porous fluororesin film (electrode isolation film) 11 and that of the water-repellent porous membrane (for freshwater permeation) 88 caused by the freshwater. A pair of or plurality of hydrogen-producing apparatus 30 each comprising consists of a pair of gas-permeable electrode chambers 3 and 4 are connected to electrolyze the aqueous electrolyte solution under a pressure equal to the water-resistant pressure of the water-repellent porous membrane and at a voltage higher than or equal to the decomposition voltage of water, and thus hydrogen gas can be produced in the negative electrode chamber and oxygen gas or gaseous chlorine in the positive electrode chamber.

In one embodiment, caustic soda can be directly produced inside a negative electrode chamber by performing electrolysis while applying hydraulic pressure on the water-repellent porous membrane without using a diaphragm or ion exchange membrane as in a conventional method. As shown in FIG. 12, caustic soda 31 is produced as follows. That is, an aqueous base metal salt solution 32 of, for example, sodium chloride, Chile saltpeter or sulfate of soda is pressurized with the water-resistant pressure of the water-repellent porous membrane 11 or the hydraulic pressure higher than or equal thereto, for electrolysis, and thus the base metal hydroxide (caustic soda) 31 is produced in a water-filled electrode chamber 40 isolated by the water-repellent porous membrane 11.

As shown in FIG. 12(A), a hydraulic pressure equal to the water-resistant pressure is applied to the aqueous base metal salt solution (aqueous sodium chloride solution) 32 in the sealed container 1, and the water-filled electrode chamber 40 comprises inside a metal such as nickel or a carbon electrode. Further, water of 80° C. at highest is supplied from a water supply inlet 34. Here, water supplied may be at room temperature, but since the solubility of caustic soda is high at high temperature. Therefore, to produce caustic soda efficiently, around 80° C. is desirable. In particular, at the start of the electrolysis, the electric resistance of the water in the water-filled electrode chamber 40 is high, and therefore it is necessary to add in advance a dilute caustic soda aqueous solution. It comprises the water supply inlet 34 for supplying water to the water-filled electrode chamber 40, a negative electrode product collecting port 35 for collecting concentrated base metal hydroxides (concentrated caustic soda aqueous solution) 31 generated, and a produced-gas (hydrogen gas) collecting pipe 12 at the top portion. On the other hand, the positive electrode is formed of the gas-permeable electrode chamber 41, and comprises a positive electrode 37 of, for example, fibrous carbon, granular carbon or porous carbon, tightly attached to the water-repellent porous membrane 11. It also comprises a produced-gas collecting pipe 12 for directly collecting gases generated on the positive electrode surface, such as gaseous chlorine, nitrous acid gas and sulfurous acid gas. But, considering transportation of the product, an aqueous solution is more convenient than a gas. Therefore, as shown in FIG. 12(B), the structure of the water-filled electrode chamber 40 is adopted as a positive electrode, and here to have the reaction of negative ion and water, a dilute hydrochloric acid aqueous solution is added in advance to water of room temperature, supplied from the water supply inlet 34, and then, electrolysis is carried out between the negative electrode plate 36 and the positive electrode plate 38 through the water-repellent porous membrane 11 to have an ionic reaction ($2Cl^-+2H_2O \rightarrow 2HCl+O_2$). The acid (hydrochloric acid) 33 generated here, is collected through a concentrated acid (hydrochloric acid) outlet port 42 and oxygen is collected through the produced-gas collecting pipe 12.

In one embodiment, a water-repellent porous membrane is used as an ON/OFF switch for ion, to deposit a base metal element, which is most hydrophobic, by electrolysis of an aqueous solution (a base metal collecting device). As shown in FIGS. 13(A) and (B), in order to produce a base metal on a negative electrode by electrolyzing the aqueous base metal chloride solution in the sealed container 1, a mesh negative electrode 43 of a metal or carbon is brought into contact with a negative electrode side of the sealed container 1 via an isolation film of the water-repellent porous membrane 11, to form an oil-filled electrode chamber 16 whose back side is filled with oil 23. With this structure, base metals of the negative electrode product whose specific gravity is lighter than the oil 23 (namely, Li, K and Na) are collected though the negative electrode product collecting port 35 provided in an upper portion of the oil-filled electrode chamber 16, whereas those base metals whose specific gravity is heavier than the oil 23 (namely, Mg, Ca, Ba and Sr) are collected through the negative electrode product collecting port 35 provided at the bottom of the oil-filled electrode chamber 16. There are two methods of collecting positive electrode products, namely, in the form of gas and in the form of liquid. To collect in the form of gas, as shown in FIG. 13(A), the positive electrode should be formed of a gas-permeable electrode chamber 41, and comprises a positive electrode 37 of, for example, fibrous carbon, granular carbon or porous carbon, tightly attached to the water-repellent porous membrane 11. It also comprises a produced-gas collecting pipe 12 for directly collecting gases generated on the positive electrode surface (chlorine). But, considering transportation of the product, an aqueous solution is more convenient than a gas. Therefore, as shown in FIG. 13(B), the structure of the water-filled electrode chamber 40 is adopted as a positive electrode, and here to have the reaction of negative ion and water, a dilute hydrochloric acid aqueous solution is added in advance to water of room temperature, supplied from the water supply inlet 34, and then, electrolysis is carried out between the negative electrode plate 43 and the positive electrode plate 38 through the water-repellent porous membrane 11 to have an ionic reaction ($2Cl^-+2H_2O \rightarrow 2HCl+O_2$). The acid (hydrochloric acid) 33 generated here, is collected through a concentrated acid (hydrochloric acid) outlet port 42 and oxygen is collected through the produced-gas collecting pipe 12.

In one embodiment, the interface between an aqueous base metal salt solution of an element of Group 1 or 2 of the periodic table and an oil, may be used as a virtual negative electrode, and the aqueous base metal salt solution can be electrolyzed to deposit a negative electrode product in the oil layer. A as shown in FIGS. 14(A) and (B), in the oil-filled electrode chamber 16 separated by the sealed container and the water-repellent porous membrane 11, the aqueous base metal salt solution 32 is electrolyzed between a virtual negative electrode surface 19 of the interface of the oil 23 and the aqueous base metal salt solution 32, and a positive electrode 37 (when a gas-permeable electrode chamber is used) or a positive electrode plate 38 (when a water-filled electrode chamber is used), to deposit a negative electrode product in the oil 23 in the oil-filled electrode chamber 16. Although FIG. 13 shows the gas collecting electrode 41 as the positive electrode, the water-filled electrode chamber 40 can also be used. FIG. 14(A) shows a structure of the oil-filled electrode chamber 16 in which two capacitors C1 and C2 are arranged in series, and it comprises a positive electrode plate 17 on an opposite side to the water-repellent porous membrane 11 of the oil-filled electrode chamber 16. As an intermediate electrode plate 18 is inserted between the water-repellent porous membrane 11 and the positive electrode plate 17 to apply a voltage (E) 20 to the capacitor C1 formed between the intermediate electrode plate 18 in the oil tank and the positive electrode plate 17 in an oil tank. On the other hand, the aqueous base metal salt solution 32 is pressurized in the sealed container 1 and the interface between the aqueous solution of the aqueous base metal salt solution 32, transmitted through the water-repellent porous membrane 11 and the oil is used as the virtual negative electrode side 19, thus short-circuiting the positive electrode plate 17 in the oil-filled electrode chamber 16 and the positive electrode 37 in the gas collecting electrode 41 or the positive electrode plate in the water-filled electrode chamber 40. As a result, only if the capacitor C2 is formed between the intermediate electrode plate 18 in the oil tank and the virtual negative electrode side 19 and further the hydraulic pressure of the aqueous base metal salt solution 32 is pressurized by a pressure equal to the water-resistant pressure of the water-repellent porous membrane, an electrolysis is carried out to deposit base metals in the oil of the oil-filled electrode chamber 16. FIG. 14(B) shows the case where the intermediate electrode plate 18 is not provided in the oil tank of the oil-filled electrode chamber 16, but a solid capacitor C1 is provided outside the system of the oil-filled electrode chamber 16. With this stricture, when the positive electrode plate 17 in the oil tank and the positive electrode 37 in the gas collecting electrode 41 or the positive electrode plate in the water-filled electrode chamber 40 is short-circuited, a capacitor C2 is formed between the positive electrode plate 17 in the oil tank and the virtual negative electrode side 19. Here, only if the hydraulic pressure of the aqueous base metal salt solution 32 placed between the positive electrode 37 (gas collecting electrode 41) or the positive electrode plate 38 (water-filled electrode chamber 40), and the virtual negative electrode side 19 is pressurized by a pressure equal to the water-resistant pressure of the water-repellent porous membrane, electrolysis is carried out to deposit base metals in the oil of the oil-filled electrode chamber 16. Thus, when the hydraulic pressure of the aqueous base metal salt solution 32 is maintained at a pressure equal to the water-resistant pressure of the water-repellent porous membrane 11, the desired base metal can be selected by heavy liquid separation in the oil of the oil-filled electrode chamber 16. Thus, when the positive electrode is the gas-permeable electrode chamber, a positive-electrode product gas can be extracted continuously or when it is the water electrolytic chamber, concentrated inorganic acid such as concentrated hydrochloric acid or a positive-electrode product gas such as oxygen gas can be extracted continuously.

In one embodiment, when a porous carbon film is used as both an isolation film for molten salt and a negative electrode, metal hydride can be formed in the process of transferring moves anions of hydrogen gas from the negative electrode side to the positive electrode side of the molten salt. As shown in FIG. 15, the base metal hydroxide molten salt (caustic soda) 46 is ionized by a molten-salt heating heater 48 into the state of $Na^+ + OH^-$. On the other hand, the electrode chamber which constitutes a negative electrode is the gas-permeable electrode chamber 41 and hydrogen gas is supplied with pressure into the gas-permeable electrode chamber 41 through a hydrogen-gas injection port 47 is pressurized into the base metal hydroxide molten salt (caustic soda) 46 through the member 44 functioning both as the porous-carbon negative electrode plate and the isolation film. In this state, when the voltage (E) 20 higher than or equal to the decomposition voltage of generation of hydrogen anion is applied between the member 44 functioning both as the porous-carbon negative electrode plate and the isolation film and the positive electrode plate 38, hydrogen anion ($H^-$) is generated to cause an ionic reaction with the base metal hydroxide molten salt (caustic soda) 46 in the ionic state of $Na^+ + OH^-$, thus forming a base metal hydride ($Na^+ + H^- = NaH$). Here, the specific gravity of caustic soda molten salt (NaOH) is 2.13, but since the specific gravity of sodium hydride (NaH) is as light as 0.92, the base metal hydride (sodium hydride) 49 surfacing from the base metal hydroxide molten salt (caustic soda) 46 while crystallizing and solidifying as upper residual is collected from a base metal hydride collecting port 51. The base metal hydride thus generated violently causes hydrolysis with water to produce hydrogen twice as much as with a simple base metal element. Further, as shown in FIG. 16, the melting point of hydroxides of elements of those of Group 1 (Li, K and Na), those of Group 2 (Mg, Ca, Sr and Br) and that of Group 13 (aluminum) are remarkably low as compared to oxides thereof. Of these, the melting points of hydrides are higher than hydroxides thereof except for Mg and Al. Further, the specific gravity of hydride is lower than hydroxide. Therefore, those except Mg and Al can form molten salts at relatively low temperatures, and when reacted with hydrogen anion, the thus produced hydrides can be surfaced as upper residuals, and subjected to gravity classification simply. Especially, as to the Group 1 elements, the melting point is higher in the hydride than in the element itself. The melting point of Na is 98° C., that of NaH is 800° C. and that of K is 64° C., whereas the melting point of KH is as high as 417° C. Although K and Na, which have extremely low melting points, require severe cautions for handling, when they are hydrogenated, the melting points become higher, the specific gravity becomes lighter, and also twice as much hydrogen can be obtained by hydrolysis. Therefore, it is expected as a hydrogen producing source for, for example, hydrogen power generation or a hydrogen car. According to the Fire Services Law, Na is a third class hazardous material, and a spontaneously combustible and water-reactive substance; however, the melting point of NaH is low, and especially that of Na is as lower as 98° C. for the reason stated above. Cautions are required for handling, since it may react to moisture in the air, causing explosion. When metallic sodium (Na) and sodium hydride (NaH) are compared with each other generally in safety, both are third-class hazardous materials and water-reactive chemicals, which violently react with water, according to the Fire Services Law. However, the class of hazardous material for sodium hydride is as low as Class II as compared to the case of metallic sodium of Class I and thus it is comparatively safe and easy to handle. Generally, metallic sodium is stored in kerosene, whereas grains of sodium hydride (NaH) are coated simply with a paraffin sheet and are comparatively safe to handle. Further, when metallic sodium is made to react with water, 0.5 mol of hydrogen (H) is generated: (Na+H$_2$O→1/2H$_2$+NaOH). But in the case of sodium hydride (NaH), it generates 1 mol (twice as much hydrogen): (NaH+H$_2$O→H$_2$+NaOH). Thus, sodium hydride (NaH) is promising as a hydrogen (H2)-producing material. Thus, although sodium (Na) is unstable if not kept in oil and there is danger of explosion by conditions, once converted into sodium hydride (NaH) by hydrogenation, the melting point becomes 800° C., which is safe and long-term storable. Therefore, it becomes suitable to be used to produce hydrogen by making it react with water when necessary. On the other hand, in the case of MgH$_2$ or AlH$_3$, which has a melting point lower than that of a hydroxide thereof, a method of collecting the products while cooling the steam with a cooled wall provided at an upper portion of the molten salt tank is adopted. Here, since a fluororesin may be affected if brought into direct contact with metallic sodium, an oil such as gas oil or petroleum should be mixed thereto when placing a making water-repellent porosity fluorine membrane and metallic sodium close to each other.

In one embodiment, there is provided a primary or secondary battery having a structure in which a sealed container formed of a water-repellent porous membrane (envelope-type) filled with an aqueous electrolyte solution is sandwiched between with the plates of a positive electrode and a negative electrode. This battery is of such a mechanism that a pressure equal to the water-resistant pressure of the water-repellent porous membrane is applied to the aqueous electrolyte solution to have an electrochemical reaction between both positive and negative electrodes for charging and discharging, and the pressurization on the aqueous electrolyte solution is released to avoid self-discharge between the electrodes for storage of charge. As shown in FIG. 17, a sealed container (envelope-type) 55 containing the aqueous electrolyte solution 14, whose both sides are made of the water-repellent porous membranes 11, is sandwiched between a negative electrode chamber (for battery) 52 and a positive electrode chamber (for battery) 53. Then, a pressure equal to the water-resistant pressure of the water-repellent porous material 11 is applied to the aqueous electrolyte solution 14 in the sealed container (envelope-type) 55 with a pressure-applying member 6 for charging (FIG. 17(A)), and charge is applied to the negative electrode chamber (for battery) 52 and the positive electrode chamber (for battery) 53 through the aqueous electrolyte solution 14 having passed through the water-repellent porous material 11 for charging. After the completion of charging, the pressurization on the aqueous electrolyte solution 14 in the sealed container 55 (envelope-type) is released to avoid the self-discharge between both electrodes, thereby storing the charge (FIG. 17(B)). For discharging, again, a pressure equal to the water-resistant pressure is applied to the aqueous electrolyte solution 14 in the sealed container 55 (envelope-type) of the water-repellent porous membrane (FIG. 17(C)). For electrodes of batteries, safety and long-term stability are important. Therefore, the following items should be considered for the structure of electrode chambers. That is, in the case where the negative electrode plate is made of an amphoteric element (Zn, Al, Sn or Pb) or Mg, or a metallic element excluding a Group 1 or Group 2 element, which has an ionization tendency higher than that of hydrogen (that is, Ti, Mn, Cr, Ga, Fe, Cd, Co, Ni or Fe), the surroundings of the electrode plate tightly attached to the water-repellent porous membrane is not necessarily isolated from the external environment. On the other hand, in the case where the negative electrode is of a Group 1 or Group 2 element and consists of a solid body, for storing negative electrode products of a Group 1 or Group 2 element in the cavity inside the porous electrode of carbon, it is necessary to enclose the electrode plate in a box, or cover with a coating, a water-repellent processed membrane or a resin film to isolate it from the external environment. In the case of the positive electrode, that is, if the positive electrode plate uses a metal having an ionization tendency lower than that of hydrogen, a metal oxide, air or oxygen, it is not necessarily required to isolate the electrode plate attached to the water-repellent porous membrane with the external environment. Or if the positive electrode is of a halogen gas except for fluorine or a metal halide, it is necessary to cover the surroundings of the electrode plate attached to the water-repellent porous membrane with a box, coating, water-repellent processed membrane or a resin film, or mold the entire battery to isolate it from the external environment. However, if the positive electrode plate is of a water-repellent material or subjected to a water-repelling treatment, a water-repellent porous membrane is not required, but it can be directly put into an aqueous electrolyte solution.

In the primary or secondary battery of the present invention, a high electromotive force and discharge capacity can be achieved by using a base metal for the negative electrode and oxygen or halogen for the positive electrode (FIG. 1). In this battery, an aqueous electrolyte solution can be made from a compound of a base metal element and oxygen or a halogen element. In this case, the discharge capacity becomes higher, as the solubility of the compound in water is higher at room temperature. In order to perform highly efficient charging, it is desirable that the solubility of a base metal hydroxide (FIG. 18) or base metal halide (FIG. 19) in water be high at room temperature when starting charging. At starting discharging, in order to continuously outputting high-capacity power for a long time, the dissolution density of the hydroxylated base metal hydroxide or base metal halide should desirably at a low state. At the end of discharging, the dissolution density should desirably be high and also close to saturation. When performing high-speed charging or high power discharging, it is desirable to warm the aqueous electrolyte solution (with, for example, hot spring, industrial waste heat, motor-cooling circulatory water). The solubility of the compound becomes higher when the temperature becomes higher to some extent except for NaCl, whose property is not dependent on the rise in temperature. Especially, in the case of Ba(OH)$_2$, the solubility is 5% at room temperature, but it rises abruptly from 40° C., and reaches a solubility of 60% at 80° C. The solubility of each of compound candidates in water at 60° C. is shown in FIG. 20. In FIG. 2, a quadruple circle indicates a solubility of 80%; a triple circle indicates a solubility of 60 to 80%; a double circle indicates a solubility of 30 to 60%; a single circle indicates a solubility of 10 to 30%; a small circle indicates a solubility of 1 to 10%: x indicates a solubility of 1% or less; and a triangle (Δ) indicates a compound which will dissolve if an alkali is added. Aqueous electrolyte solutions with high solubility shown in FIG. 18 and those with high discharge capacity shown in FIG. 1 should desirably used.

The batteries according to the present invention include an oxygen/base metal battery. In order to lighten batteries, a metal with light specific gravity is adopted for the negative electrode and the air in the atmosphere is used for the positive electrode. As indicated by the calculated value of the discharge capacity of the base metal/oxygen battery shown in FIG. 1, when calculated in consideration of the weight of oxygen, a Li/O battery has 6,165 Wh/kg, but oxygen can be supplied from the atmosphere, and therefore, neglecting the weight of oxygen, it can exhibit a high discharge capacity (as 11,680 Wh/kg). Similarly, an Mg/O battery exhibits 3,658 Wh/kg, but neglecting the air, it will be high as 6,067 Wh/kg. An Al/O battery exhibits 3,264 Wh/kg, but neglecting the air, it will be high as 6,165 Wh/kg. However, according to the relationship between the solubility of hydroxylated base metal and temperature in FIG. 18, either $Mg(OH)_2$ or $Al(OH)_3$ hardly dissolves into water, and as a result, the negative electrode is covered with an oxide film, blocking the flow of electrons. This is also the case for $Ca(OH)_2$. It is known that Al, which belongs to the amphoteric elements, dissolves if caustic soda is added to the aqueous electrolyte solution (as $Al(OH)_3+NaOH \rightarrow Na[Al(OH)_4]$), but in the present invention, only Na/O, K/O, Ba/O, Li/O and Sr/O batteries are considered. The reason for this is that in room temperature environment, the order in efficiency ranking of these batteries is: K/O>Na/O>Li/O>Ba/O>Sr/O (or Ba/O where the temperature is high, such as hot spring), and the efficiency order in discharge capacity is: Li/O>Be/O>Al/O>Mg/O>Ca/O>Na/O>Sr/O>K/O>Ba/O. The structure of a battery constructed in consideration of these results is shown in FIG. 21. Here, for the positive electrode chamber (for battery) 53, oxygen or air is used, whereas for the negative electrode chamber (for battery) 52, a Group 1, Group 2, and/or Group 13 metal element are used. Moreover, in a sealed container (envelope-type) 55 whose opposing walls are made of a water-repellent porous membrane 11, a base such as caustic soda, caustic potash (potassium hydroxide) or barium hydroxide, or an acid such as sulfuric acid, hydrochloric acid or nitric acid is accommodated as the aqueous electrolyte solution 14. Especially, the oxygen electrode of the positive electrode chamber (for battery) 53 makes air or oxygen adsorbed to the carbon-made porous electrode plate 58 (activated carbon) to form a collector electrode plate 64 of a positive electrode. Further, an auxiliary positive electrode 56 for charging (mesh electrode) is provided between the water-repellent porous membrane 11 and the carbon-made porous electrode plate (activated carbon) to void generation of heat of the carbon-made porous electrode plate 58 (activated carbon) (FIG. 21(A)), or the surface in contact with the water-repellent porous membrane 11 of the positive electrode is formed into a source of supply of oxygen as a metal oxide (CuO or $Al_2O_3$) 59 of a metal plate 60 (FIG. 21(B)).

On the other hand, the negative electrode chamber (for battery) 52 is formed into an outside air isolation type negative electrode 57 formed by adsorbing negative electrode products of a Group 1 or Group 2 element and/or Group 13 element to the pores inside or on the surface of a solid-body electrode of a Group 1, or Group 2 element and/or Group 13 element or a carbon-made electrode plate, and the surroundings of the negative electrode is covered with a resin film 61 or the inside of the negative electrode is filled with an oil 22 to isolate it from the external environment.

In this battery (primary or secondary battery), charging is carried out while the aqueous electrolyte solution 14 is pressurized, and when the charge is completed, the pressurization on the aqueous electrolyte solution 14 is released to store charge. For discharging, the aqueous electrolyte solution 14 is pressurized to start discharging.

The batteries of the present invention include a metal/chlorine battery, whose electrode structure can be made maintenance-free. Generally, halogen gas is poisonous. Therefore, metal chloride (solid) is used as a positive electrode in the present invention. As shown in FIG. 22, a metal chloride aqueous solution is sealed as the aqueous electrolyte solution 14 in the sealed container (envelope-type) 55 whose opposing walls are formed of a water-repellent porous membrane 11. The electrode chamber 52 attached to the water-repellent porous membrane 11 comprises negative electrode plates (for battery) 62 and 65 and a positive electrode chamber 53 provided as a metal plate (for battery) 64 via a metal chloride 63. The metal chloride 63 as the positive electrode is directly in contact with the porous membrane 11. In this battery (primary or secondary battery), charging is carried out while the aqueous electrolyte solution 14 is pressurized with the pressure-applying member 6. Then, positive ions of the metal contained in the aqueous electrolyte solution 14 are deposited on the negative electrode plate 62. When the metal chloride 63 of the metal is generated on the surface of the metal plate 64 of the positive electrode to complete charging, the pressurization on the aqueous electrolyte solution 14 is released to store charge. For discharging, pressure is applied to the aqueous electrolyte solution 14 with the pressure-applying member 6. FIG. 22(A) is a conceptual diagram of a single-layer battery, and FIG. 22(B) is a conceptual diagram of a multilayer battery.

A multilayer battery (FIG. 22(B)) is formed by connecting single-layer batteries (FIG. 22(A)) in series. The structure of the positive electrode chamber 53 of a single-layer battery includes a metal chloride film 63, which is a portion of a single metal plate, that is brought into contact with the water-repellent porous membrane 11 is chlorinated, and a collector electrode plate 64, which is a not chlorinated metal portion. The electrode configuration between the first layer and the second layer of the multilayer battery includes a positive electrode (a chloride of the metal used for the negative electrode) 66 brought into contact with the first layer and the collector electrode plate 64 of the single-layer battery used as the negative electrode plate 65 of the second layer, and subsequent layers arranged similarly. In the case of primary batteries, the aqueous electrolyte solution 14 may be of an arbitrary metal chloride including sodium chloride. Here, in a single-layer battery, the combination of a negative electrode and a positive electrode may be metals arbitrarily selected from Zn, Mg, Al, Ni, Pb, etc., or which may be of the same metal, and the positive electrode may be a chloride of an arbitrarily selected metal. In a multilayer primary battery, both the negative electrode and the positive electrode are of the same metal, and the positive electrode is made of a chloride of the metal used for the negative electrode. In the case of secondary batteries, the aqueous electrolyte solution 14 is of a chloride of the metal used for the negative electrode, and in a single-layer secondary battery, the combination of a negative electrode and a positive electrode are those arbitrarily selected from Zn, Mg, Al, Ni, Pb and the like, or which may be of the same metal. Note that it is desirable to make coarse the electrode surface on the positive electrode interposed between the opposing surfaces of the sealed container (envelope-type) 55 to increase the surface area, and also to provide a cover for the outer walls of the positive electrode or the entire battery device to protect metal chloride from moisture. As to this metal/chlorine battery, as shown in FIG. 19, the order of metal chlorides in solubility at room temperature is, from high to low, as follows: $ZnCl_2>CdCl_2>LiCl>BeCl_2>CaCl_2>MnCl_2>NiCl_2>FeCl_2>CoCl_2>MgCl_2>AlCl_3>B$ On the other hand, as shown in FIG. 1, the order in discharge capacity is: $BeCl_2>LiCl>AlCl_3>MgC_{l2}>CaCl_2>NaCl>KCl>SrCl_2>ZnCl_2>BaCl_2$.

As for the present invention, although Zn, Mg, Al, nickel and

Pb are recommended as a negative electrode plate usable in the atmosphere, but also Group 1 and Group 2 metals can be used as well. In this case, the negative electrode is an electrode made by adsorbing Group 1 and 2 elements as negative electrode products on the solid electrode of Group 1 or 2 element, or the pores in the surface or inside of the carbon-made porous electrode plate, and further it is necessary to cover the surroundings of the negative electrode with a resin film, or to make the inside of the negative electrode filled with oil, to isolate it from the external environment.

The batteries of the present invention further include metal/bromine and metal/iodine batteries. Generally, a halogen gas is a harmful gas, but at room temperature, bromine (boiling point of 58.8° C.) is in a liquid state and iodine (boiling point of 113.6° C.) is in a solid state. Further, the order of metal bromides in solubility at room temperature is, from high to low, as follows: $ZnBr_2 > LiBr > CaBr_2 > MnBr_2 > NiBr_2 > FeBr_2 > CoBr_2 > SrBr_2 > CdBr_2 > NaBr > KBr > BaBr_2$. On the other hand, as shown in FIG. 1, the order in discharge capacity is: $CaBr_2 > MgBr_2 > NaBr > LiBr > KBr > SrBr_2 > MnBr_2 > NiBr_2 > FeBr_2 > BaBr_2$. Moreover, the order of metal iodides in solubility at room temperature is, from high to low, as follows: $ZnI_2 > CaI_2 > BaI_2 > NaI > SrI_2 > LiI > KI > MgI_2 > CaI_2 > CoI_2 > PbI_2$. On the other hand, as shown in FIG. 1, the order in discharge capacity is: $LiI > NaI > CaI_2 > MgI_2 > KI > SrI_2 > ZnI_2 > BaI_2 > PbI_2 > CoI_2 > CdI_2$. Based on this, with the present invention, a positive electrode chamber which stores halogen in the pores inside a solid body was considered. In this positive electrode, as shown in FIGS. 22(A) and (B), activated carbon grains or carbon fibers 67 in a container isolated from the external environment mixed with a bromine liquid 68 or iodine grains 69, and the positive electrode chamber 53 is tightly attached to the water-repellent porous membrane 11 of the sealed container (envelope-type) 55. The collector electrode plate 64 is provided on the back surface. On the other hand, as the negative electrode, a bare electrode plate made of a metal element having an ionization tendency higher than that of hydrogen except for amphoteric elements or Mg or Group 1 or 2 elements may be used, or a solid electrode may be used when using a Group 1 or 2 element. Or, a negative electrode product of a Group 1 or 2 element need be deposited and stored in the pores inside the carbon-made porous electrode plate, and the surroundings of the negative electrode be covered with a resin film or the inside of the negative electrode is filled with oil to isolate it from the external environment. For the aqueous electrolyte solution 14 of this battery, an aqueous solution of a bromide or an iodide of a metal element used for the negative electrode is used, and the atmosphere temperature of the positive electrode needs to be maintained always lower than or equal to the boiling point. In the negative electrode, as shown in FIG. 22(A), a metal element having an ionization tendency higher than that of hydrogen, except for amphoteric elements (Zn, Al, Sn and Pb) and Mg or Group 1 or 2 elements, (that is, Ni, Pb, Ti, Mn, Cr, Ga, Fe, Cd, Co, Ni or Fe) is used as the negative electrode plate (bare electrode plate) 62 which is not affected if exposed to the outside air. Or as shown in FIG. 22(B), when using a Group 1 or 2 metal, the negative electrode chamber (for battery) 52 is formed into an outside air isolation type negative electrode 57 formed by adsorbing negative electrode products of a Group 1 or Group 2 element to the pores inside or on the surface of a solid-body electrode of a Group 1, or Group 2 element (Li, Na, K, Ca, Sr or Ba) or a carbon-made porous electrode plate, and electrons are extracted from the collector electrode plate 64. Further, the surroundings of the negative electrode are covered with a resin film 61 or the inside of the negative electrode is filled with an oil 22 to isolate it from the external environment. In this battery (primary or secondary battery), charging is carried out while the aqueous electrolyte solution 14 is pressurized, and when the charge is completed, the pressurization on the aqueous electrolyte solution 14 is released to store charge. For discharging, the aqueous electrolyte solution 14 is pressurized to start discharging.

The batteries of the present invention include further a metal/fluorine battery. Fluorine gas is deadly poisonous and generally is very difficult to handle. However, as shown in FIG. 1, the electrode potential is +2.87V, which is 7.175 times higher as compared to +0.4V of oxygen. The discharge capacity is large as NaF (3,568 Wh/kg)>KF (2,676 Wh/kg) >AlF3 (2,589 Wh/kg), but a few kinds are available. Further, fluorides have strong bond and most of them are insoluble in water, with very few exceptions of KF, NaF and $AlF_3$ having solubilities of 50%, 4% and 0.5%, respectively, at room temperature. Thus, a promising negative electrode material is only potassium (K), whereas sodium (Na) and aluminum (Al) are inefficient. On the other hand, if fluoridated graphite is used for a positive electrode, deadly poisonous fluorine gas can be avoided to manufacture K/F, Na/F and Al/F batteries. As the aqueous electrolyte solution 14 of these batteries, an aqueous solution of potash fluoride is the optimal. But, since aluminum fluoride is insoluble, caustic soda and caustic potash may be added to the aqueous electrolyte solution 14. In this manner, an Al/F primary battery having an electromotive force of 4.54V can be obtained. A K/F primary or secondary battery has an electromotive force of 5.79V, and is lightweight, and therefore it is promising as a high-discharge capacity battery. In the positive electrode, as shown in FIG. 24(A, B), the positive electrode chamber 53 is made of graphite 70, and tightly attached to the water-repellent porous membrane 11 of the sealed container (envelope-type) 55, and further comprises the collector electrode plate 64 on the back surface. On the other hand, as the negative electrode, an Al negative electrode plate 71 is tightly attached to the water-repellent porous membrane 11 of the sealed container (envelope-type) 55, and caustic soda or caustic potash is added to aluminum fluoride to prepare the aqueous electrolyte solution, and thus a primary battery is prepared (FIG. 24(A)). As shown in FIG. 24(B), when using potassium (K) and sodium (Na) for a primary or secondary battery, the negative electrode chamber (for battery) 52 is formed into an outside air isolation type negative electrode 57 formed by adsorbing negative electrode products of Group 1 and/or Group 2 element to the pores inside or on the surface of a solid-body electrode of Group 1 and/or Group 2 element (Li, Na, K, Ca, Sr or Ba) or a carbon-made porous electrode plate, and electrons are extracted from the collector electrode plate 64. Further, the surroundings of the negative electrode are covered with a resin film 61 or the inside of the negative electrode is filled with an oil 22 to isolate it from the external environment. Here, charging and discharging are carried out while the aqueous electrolyte solution 14 in the sealed container (envelope-type) 55.

The capacitors of the present invention include a capacitor of such a structure that positive and negative electrode plates are respectively provided in contact with opposing surfaces of a sealed container made of a liquid-repellent porous membrane (envelope-type) in which a dielectric liquid or an electrolyte solution is sealed. In this capacitor, for charging and discharging, a pressure equal to the liquid-resistant pressure of the liquid-repellent porous membrane is applied to this electrolyte solution to carry out an electrochemical reaction between both electrodes, and for accumulating electricity, the pressurization on the electrolyte solution is released. As shown in FIG. 25 (conceptual diagram), this capacitor has a structure in which a positive electrode chamber 53 and a negative electrode chamber 52 are provided on outer surfaces of both opposing side walls of a sealed container 55 made of the water-repellent porous membrane (envelope-type) and containing an oil-based or aqueous dielectric liquid 72 or an aqueous electrolyte solution 14. The electrodes which constitute a pair of positive and negative electrode chambers 52 and 53 arranged on both opposing side walls of a sealed container (envelope-type) 55 made from a water-repellent porous membrane, comprises an electric double-layer capacitor electrode 74 in which organic molecules are adsorbed on the surface of a electrode plate 73 or a carbon electrode of, for example, activated carbon, graphite or nano-carbon, or a redox capacitor electrode 75 made of an oxide film formed on the surface of an electric conductor, an electrically conductive polymer, activated carbon or the like, or a hybrid capacitor electrode 76 of activated carbon, polyphenol, graphite lithium titanate or the like. In this capacitor, for charging, a pressure equal to the liquid-resistant pressure of the liquid-repellent porous membrane 11 is applied to a dielectric liquid 72 or an electrolyte solution 14 to apply a charge between both electrodes (FIG. 25(A)), the application of the pressure is released for storage of charge (FIG. 25(B)), and a pressure equal to the liquid-resistant pressure is applied for discharge. An encircling dotted line 77 shown in FIG. 25(B) is drawn for convenience as the liquid-repellent porous membrane 11 and the electrodes 73, 74, 75 and 76 of the electrode chambers 52 and 53 are separated, but they are in contact in practice. Here, since there is no pressure applied, the pores of the liquid-repellent porous membrane 11 do not contain liquid. For this reason, the water-repellent porous membrane 11 is considered to be a low-dielectric constant film.

Therefore, as shown in FIG. 25(D), if the dielectric solution enters the pores, as an electrical circuit, it can be expressed as a variable capacitor ($C_2$) is formed, which operates according to pressurization, and if an aqueous electrolyte solution enters the pores, it can be indicated as a rheostat (R). That is, when accumulating electricity, there is no dielectric liquid but only air in the pores of the liquid-repellent porous membrane 11, and therefore it is considered that a capacitor ($C_1$) which stores charge is connected in series by the low-dielectric constant capacitor ($C_2$) on both ends. If a pressure is applied thereto, in the case of a dielectric liquid, $C_1=C_2$ results, whereas in the case of an electrolyte, the value R becomes infinitely close to 0 for charging or discharging.

The capacitors of the present invention include an electric double-layer capacitor and a redox electrochemical capacitor. In this capacitor device, positive and a negative electrode chamber are high dielectric constant capacitors, and the insides of the sealed container (envelope-type) of the water-repellent porous membrane include an electrically conductive material and an electrolyte. Further, the water-repellent porous membrane is a switch which puts on and off the continuity between the positive and negative electrode chambers. FIG. 26 is a diagram briefly showing the electric double-layer capacitor, and FIG. 27 is a diagram briefly showing the redox capacitor. As shown in FIGS. 26 and 27, a porous electrical conducting materials 78 of, for example, metal fiber, carbon fiber or activated carbon filled in the sealed container (envelope-type) 55 made of the water-repellent porous membrane interposed between a pair of positive and negative electrode chambers 52 and 53 is dampened with an aqueous electrolyte solution 14 such as dilute sulfuric acid 79 or rare caustic soda 80 and the aqueous electrolyte solution 14 is pressurized a pressure-applying member 6 by a pressure equal to the water-resistant pressure of the liquid-repellent porous membrane 11 to make the aqueous electrolyte solution to pass the pores of the liquid-repellent porous membrane 11 (FIG. 26(A), FIG. 27(A)) for charging. For storage of charge, the pressurization on the electrolyte solution is released (FIG. 26(B), FIG. 27(B)). For discharging, a pressure equal to the water-resistant pressure is again applied with the pressure-applying member 6. The encircling dotted line 77 shown in FIG. 26(B) and FIG. 27(B) is drawn for convenience as the water-repellent porous membrane 11 and the electrode chambers 52 and 53 are separated. But they are in contact in practice. Here, the pressure is not applied, and therefore there is no liquid in the pores of the liquid-repellent porous membrane 11. In this state, the water-repellent porous membrane 11 is considered as a low-dielectric constant film. Therefore, as shown in FIG. 26(D) and FIG. 27(D) along with equivalent circuits, when not pressurized, the aqueous electrolyte solution 14 does not enter the pores of the water-repellent porous membrane 11, and thus a low-dielectric constant capacitor ($C_2$) is formed. If pressurized, the aqueous electrolyte solution 14 enters the pores of the water-repellent porous membrane 11 to turn on the switch (S) as an electrical circuit, and thus the positive electrode chamber and negative electrode chamber are short-circuited via the sealed container (envelope-type) 55 made of a water-repellent porous membrane to connect two high-dielectric constant capacitors ($C_1$) in-series for charging and discharging. If the pressurization on the aqueous electrolyte solution 14 is released, the two low-dielectric constant capacitors ($C_2$) and the two high-dielectric constant capacitors ($C_1$) are connected in series to store charge. On the other hand, the negative electrode chamber 52 and the positive electrode chamber 53 are the same in structure, but the electric double-layer capacitor and the redox capacitor differ from each other.

As to the structure of the negative electrode chamber and the positive electrode chamber 53 of the electric double-layer capacitor, the activated carbon grains 67 tightly attach to the water-repellent porous membrane 11 and the collector electrode plate 64 is provided on the opposite surface, thus isolating the positive and negative electrode chambers 52 and 53 from the outside air, as shown in FIGS. 26(A), (B) and (C).

The structure of the negative electrode chamber 52 and the positive electrode chamber 53 of the redox capacitor comprises, as shown in FIGS. 27(A), (B) and (C), a redox-capacitor metal plate (Al) 108 for a and a redox-capacitor metal oxide film ($Al_2O_3$) 109 as a dielectric, prepared by electrically oxidizing the surface of the metal plate, which faces the water-repellent porous membrane 11. Each of the metal plates functioning as positive and negative electrodes is tightly attached to the porous membrane 11 through the metal oxide film 109.

In the present invention, base metal elements can be separately collected from an aqueous solution in which base metal salts are mixed. A plurality of sets of the above-described hydrogen-producing apparatus and base metal collecting devices are connected in series, and electrolytic refining is carried out in these devices starting from the hydrogen-producing apparatus in the order of a lower decomposition voltage of the metal deposited from the aqueous electrolyte solution containing a plurality of base metal salts mixed thereinto. Then, the unreacted aqueous electrolyte solution is transferred to the subsequent base-metal collecting device, where electrolytic refining of the aqueous electrolyte solution is carried out under pressurization. Here, while the devices are operating in the order of the decomposition voltage from being low to high, the base metals are collected accordingly.

According to one embodiment of the present invention, provided is an offshore or seaside factory which produces hydrogen or caustic soda on the spot from sea water as a raw material using natural power sources obtained at sea or power, for example, midnight electric power from a seaside thermal power plant. In this embodiment, at the on-ocean and/or seaside factory, caustic soda or hydrogen is produced as described above, and further, from the produced hydrogen and caustic soda, sodium hydride produced as described above on the ocean or land. Furthermore, on the land, water is poured onto sodium hydride to produce hydrogen, and caustic soda, which is produced as a by-product, is reproduced again sodium hydride. Thus, a caustic-soda fuel cycle can be established. Moreover, caustic soda, which is an intermediate product, can also be used as an aqueous electrolyte solution for secondary batteries.

Further, according to the present invention, a predetermined substance is put into a container formed of a water-repellent porous membrane, and the container is put into a liquid of an aqueous solution or water of an electrolyte or a nonelectrolyte. Under a fluid pressure equal to the water-resistant pressure of the water-repellent porous membrane, the liquid permeates the pores of the water-repellent porous membrane to have an ionic reaction, a hydrolysis reaction or a dissolution reaction between the substance inside the container and itself.

For example, according to the present invention, in the container (reaction chamber) of the water-repellent porous membrane, contained is a substance which produces gas by hydrolysis or contacting water, a substance which produces heat by hydrolysis or contacting water, a substance which absorbs heat by hydrolysis or contacting water, or a water-soluble organic compound, or the like and the reaction chamber is put in a liquid of water or an aqueous nonelectrolyte solution contained in the sealed container. Then, a pressure that makes the difference between the external and internal pressures of the reaction chamber larger than or equal to the water-resistant pressure of the water-repellent porous membrane is applied to the water-repellent porous membrane through the liquid to introduce this liquid into the reaction chamber. Here, the substance contained in the reaction chamber reacts to this water to cause reactions of gas generation, thermogenesis, heat absorption and dissolution. The gas and aqueous solution obtained here can be used for transfer of chemicals or nutrients to a living body or addition of an organic compound to an aqueous solution, etc.

Further, according to the present invention, a tube or the like for spraying chemicals, made of a water-repellent porous membrane, is provided for a desired site, in which a hose is connected between a chemical supply inlet of the tube and a chemical aqueous solution supply source, and a pressure higher than or equal to an the water-resistant pressure of a water-repellent porous membrane can be applied to this chemical aqueous solution continuously or intermittently as needed at the chemical supply inlet, thereby making it possible to supply the chemical aqueous solution at a desired place. The chemical aqueous solution includes, for example, a chemical, a nutritive material and a fertilizer.

Furthermore, according to the present invention, a capsule in which a hydrolysis exothermic agent is sealed is provided at the tip of an endoscope and a hydraulic pressure higher than or equal to the water-resistant pressure is applied thereto through a water-repellent porous membrane, to cause a hydrolysis exothermic reaction, thereby warmly heat cancer cells in an organ with the heat thus generated.

Effect of the Invention

As mentioned above, according to the present invention, an water-resistant pressure or a hydraulic pressure higher than or equal thereto is applied to a porous fluororesin film which exhibit high electric insulation in an aqueous electrolyte solution, such as sea water and salt lake water, the aqueous electrolyte solution and/or ions permeate the pores of the porous fluororesin film. Based on this, the quantity of aqueous solution and ion which can pass through the water-repellent porous membrane can be controlled in an analog fashion, and thus the function of a switch can be assigned. The water-repellent porous membrane is used as an isolation film between the aqueous electrolyte solution and the positive and negative electrode chambers, and a pressure is applied to the aqueous electrolyte solution to cause electrolysis of the aqueous solution, which produces electrode products at each of the positive and negative electrode chambers. The thus produced products are separated and collected from the aqueous electrolyte solution. In this manner, hydrogen, caustic soda, a base metal element, etc. can be directly extracted from aqueous electrolyte solutions such as sea water and salt lake water. This technology can be applied not only to electrolytic refining, but also for to practical batteries or larger-scale capacitor. Conventionally, there is only such a method of carrying out a molten salt electrolysis at high temperature using high power. However, according to the present invention, electrolysis of aqueous solutions can be carried out at ordinary temperature, thereby creating significant economical effect. In particular, metallic sodium obtained from sea water can be expected as an alternative to petroleum energy. Further, it never drains as an energy resource which is not unevenly distributed in the world. This technology can contribute to create the world without resource war. Moreover, a base metal/air battery and a base metal/halogen battery, which are made of uses, for example, lithium, sodium or calcium as a raw material, for which an electrolyte can be used directly in the form of an aqueous solution can be used as a storage battery for renewable power which is likely to be influenced by climate. Further, it can be used as a lightweight and high-efficiency battery to contribute to development of electric vehicles, which further contributes to progress of the hydrogen society which does not output carbon dioxide or radiation.

BRIEF DESCRIPTION OF THE SEVERAL VIEWS OF THE DRAWING

FIG. 1 shows a comparison between a base metal/oxygen battery and a base metal/halogen battery in discharge capacity.

FIG. 2 is an explanatory diagram of the principle of the pressure switch of a liquid-repellent porous membrane (isolation film), and (A) shows the case where the aqueous electrolyte solution is at an water-resistant pressure or less, whereas (B) shows the case where the aqueous electrolyte solution is at the water-resistant pressure or higher.

FIG. 3A shows a comparison between the electrical properties of the solution and the role of the liquid-repellent porous membrane in the electronic switch of the liquid-repellent porous membrane (isolation film).

FIG. 4 briefly shows a chemical reactor comprising an isolation tool for the electrolyte solution provided between positive and negative electrodes, in which (A) indicates the case where the isolation tool forms a sealed container of a liquid-repellent porous membrane, (B) indicates the case where the chemical reactor is located in an open container, and (C) indicates the case where the isolation tool forms a sealed container of a liquid-repellent porous membrane and the sealed container is located in an open container.

FIG. 12 is a diagram briefly showing a device of manufacturing a base metal hydroxide (caustic soda), and (A) shows a device which manufactures a base metal hydroxide (caustic soda) on a negative electrode, and a positive electrode product gas (chlorine) on a positive electrode, and (B) shows a device which manufactures a base metal hydroxide (caustic soda) on a negative electrode and an acid (hydrochloric acid) on a positive electrode.

FIG. 16 compares and shows the melting point and specific gravity of base metal hydride and a base metal hydroxide.

FIG. 20 shows the water-solubility of an electrolyte used for a base metal/oxygen battery or a base metal/halogen battery.

FIG. 28 is a graph showing the relationship between the water-resistant pressure of the porous fluororesin film and salt concentration, in which (A) shows the case where the diameter of the pores of the porous fluororesin film is 3 μm and (B) shows the case where the diameter of the pores of the porous fluororesin film is about 10 μm.

FIG. 29 is a diagram briefly showing a hydrogen-producing apparatus used under sea surface.

FIG. 44 is a diagram briefly showing a caustic soda fuel cycle.

DETAILED DESCRIPTION OF THE INVENTION

Figure 3B:
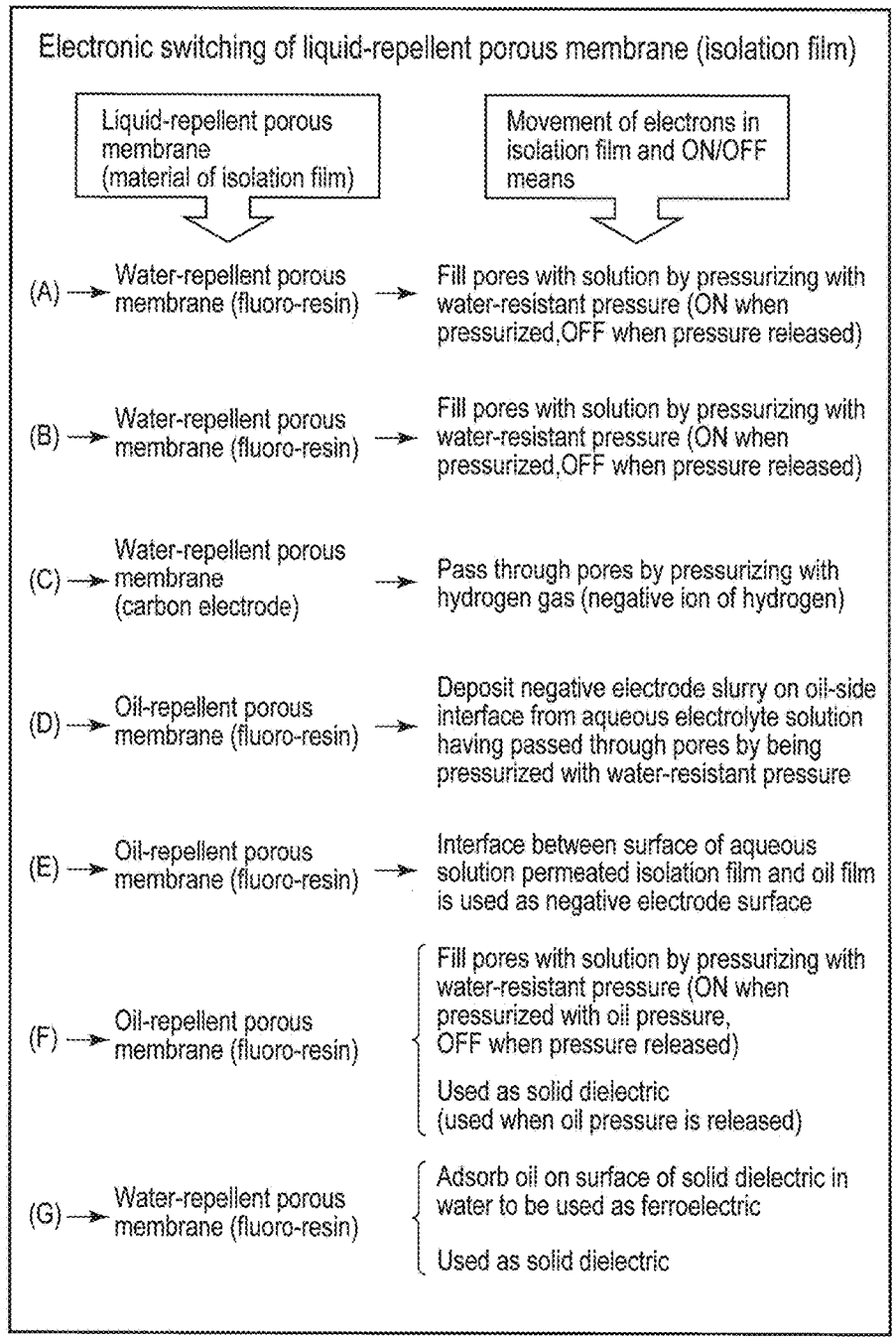
FIG. 3B shows another comparison between the electrical properties of the solution and the role of the liquid-repellent porous membrane in the electronic switch of the liquid-repellent porous membrane (isolation film).
Figure 5:
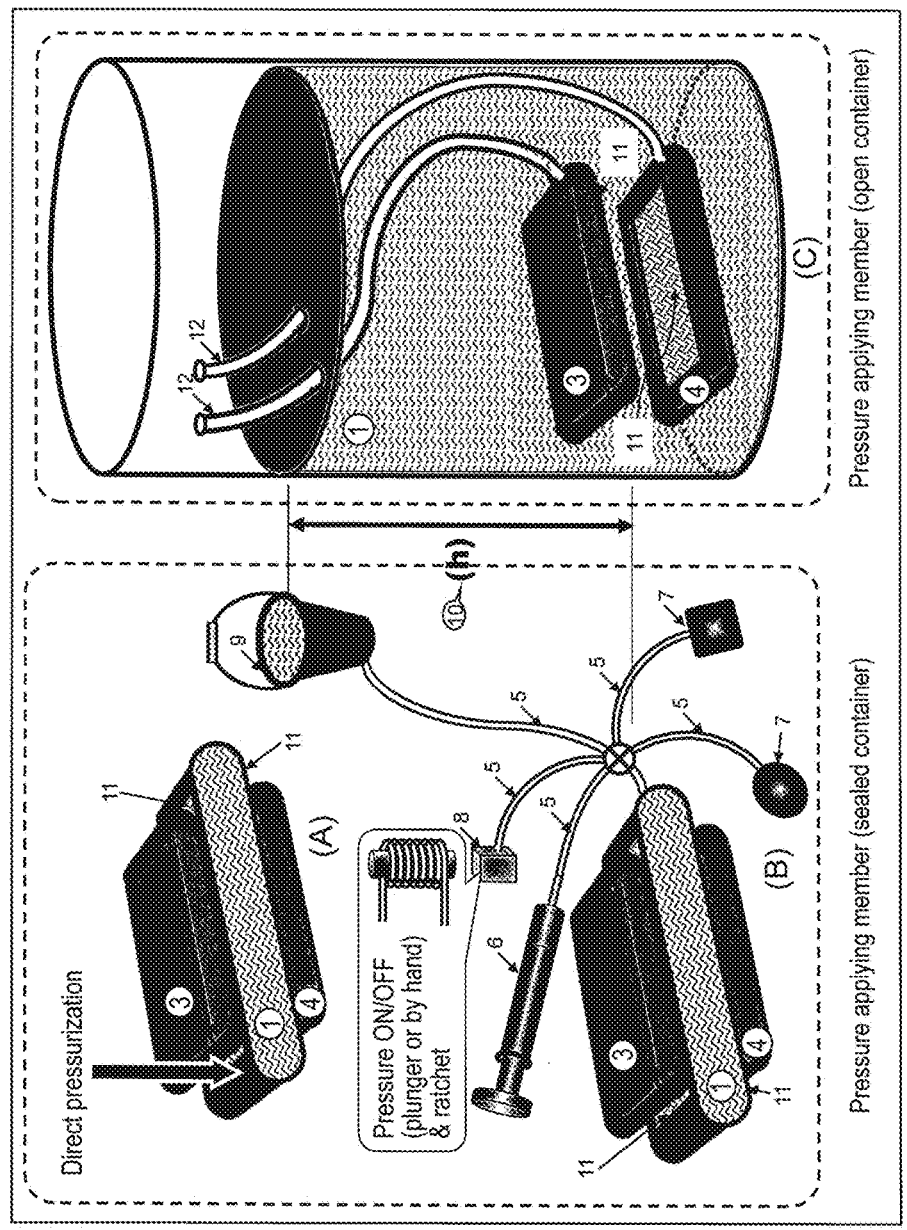
FIG. 5 briefly shows a pressure-applying member, in which (A) indicates the case where the sealed container formed of a liquid-repellent porous membrane is pressurized directly, (B) indicates the case where manual or electrical pressurization using a communicating tube is employed, or a hydraulic pressure from a pressure head is used, and (C) indicates the case where the head pressure is applied to the sealed container in an open container.
Figure 6:
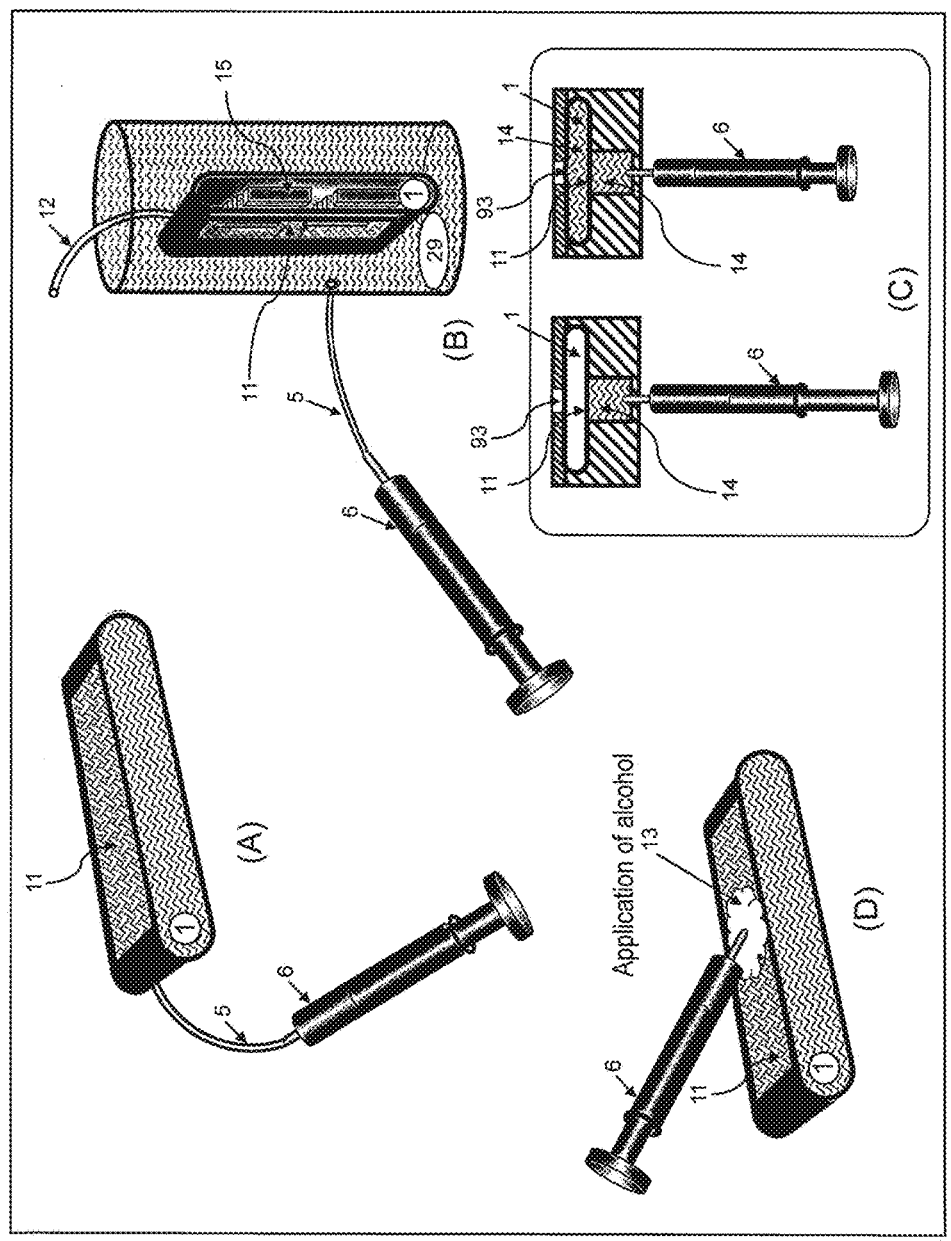
FIG. 6 is an explanatory diagram of a method of filling the inside of a hollow sealed container (bag) of a water-repellent porous membrane with an aqueous electrolyte solution, in which (A) indicates the case where the aqueous electrolyte solution is poured directly into the hollow sealed container (bag), (B) indicates the case where water or steam is applied with pressure to the solute put in the hollow sealed container (bag), (C) indicates the case where the aqueous electrolyte solution is supplied with pressure into the hollow sealed container (bag) through a water-repellent porous membrane, and (D) indicates the case where alcohol is applied on the water-repellent porous membrane of the hollow sealed container (bag) to reserve the aqueous electrolyte solution.

Effective embodiments of the present invention will be described in detail with reference to FIG. 28 to FIG. 47.

FIG. 28 is a graph plotting measured values of the water-resistant pressure of the water-repellent porous fluororesin film, which is the basis of the present invention, showing the relationship between the electrolyte concentration of an aqueous electrolyte solution and the minimum pressure required for an aqueous electrolyte solution to pass through the water-repellent porous fluororesin film (a minimum pressure difference between both sides of the water-repellent porous fluororesin film, required for an aqueous electrolyte solution to pass through the water-repellent porous fluororesin film, which is sometimes called permeation pressure difference). The water-resistant pressure is set forth in Japanese Industrial Standard (JIS) L1092:2009.

FIG. 28(A) shows results of the case where aqueous sodium chloride solutions of different concentrations were used as aqueous electrolyte solutions for a water-repellent porous membrane of a fluororesin (PTFE porous membrane NTF-1133 of NITTO DENKO CORPORATION) having a diameter of pores of 3 μm. Generally, the water-resistant pressure is a value with respect to pure water. Further, the salinity (sodium chloride) concentration of sea water is generally about 3% by weight, and the underwater saturated concentration of sodium chloride is about 25% by weight. Then, sodium chloride of various concentrations from 0% to 25% by weight was added to water, and the relationship between the concentration of sodium chloride and water-resistant pressure at room temperature was measured. The water-resistant pressure of the fluororesin-made water-repellent porous membrane was 430 mmHg (0.57 atmosphere) at a concentration of sodium chloride of 0%, 320 mmHg (0.42 atmosphere) at a concentration of sodium chloride of 10%, 280 mmHg (0.37 atmosphere) at a concentration of sodium chloride of 20%, 270 mmHg (0.36 atmosphere) at a concentration of sodium chloride of 25%. Thus, as the concentration of sodium chloride increases, the water-resistant pressure decreases. Further, the water-resistant pressure tends to decrease if the temperature of the aqueous electrolyte solution increases.

FIG. 28(B) shows results of the case where aqueous sodium chloride solutions of different concentrations were used as aqueous electrolyte solutions for a water-repellent porous membrane of a fluororesin (F-3011-3 of FLON INDUSTRY) having a diameter of pores of 10 μm. The water-resistant pressure of the fluororesin-made water-repellent porous membrane was 120 mmHg (0.16 atmosphere) at a concentration of sodium chloride of 0% and 50 mmHg (0.07 atmosphere) at a concentration of sodium chloride of 2%.

As can be seen from the results shown in FIG. 28(A) and FIG. 28(B), if the diameter of the pores of the porous membrane becomes greater, the water-resistant pressure becomes less. Moreover, since the water-resistant pressure decreases, if the electrolytic concentration increases under the same pressure (hydraulic pressure), the electrolytes of various concentrations separated by the liquid-repellent porous membrane flow from the higher concentration side to the lower. That is, when an aqueous electrolyte solution with high concentration is present in the sealed container formed of the liquid-repellent porous membrane and an aqueous electrolyte solution with low concentration is present on an outer side of the sealed container, the aqueous electrolyte solution leaks to the outside of the sealed container. In order to avoid this, it is necessary to lower the pressure in the electrode chamber tightly attached to the sealed container and to control the pressure difference so that the low-concentration aqueous electrolyte solution on the outer side of the sealed container enters the inside of the sealed container through the liquid-repellent porous membrane, and takes the route to flow into the electrode chamber through another liquid-repellent porous membrane.

Figure 7:
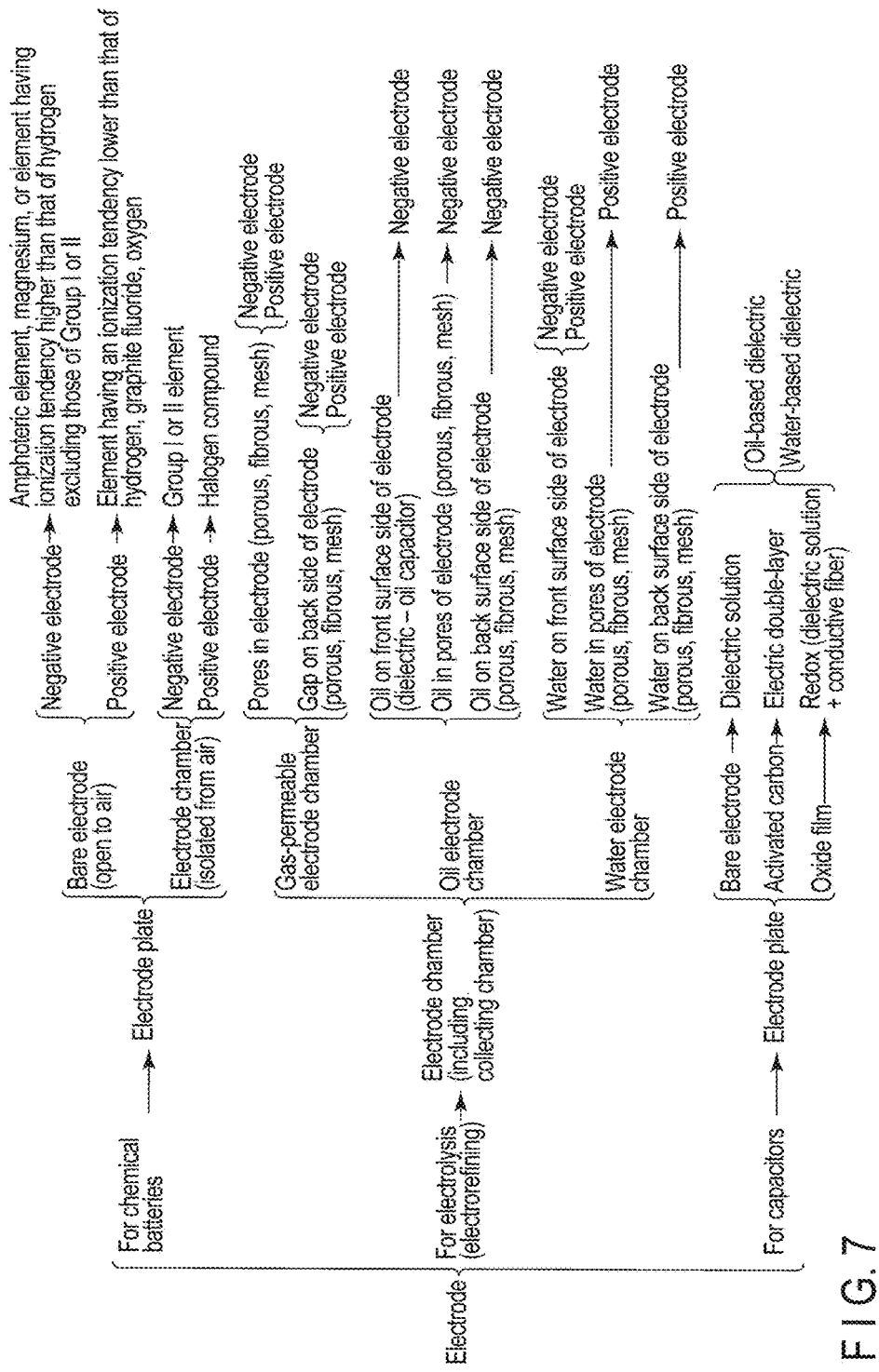
FIG. 7 shows the relationship between the structure and use of the positive and negative electrodes isolated by a water-repellent porous membrane.
Figure 8:
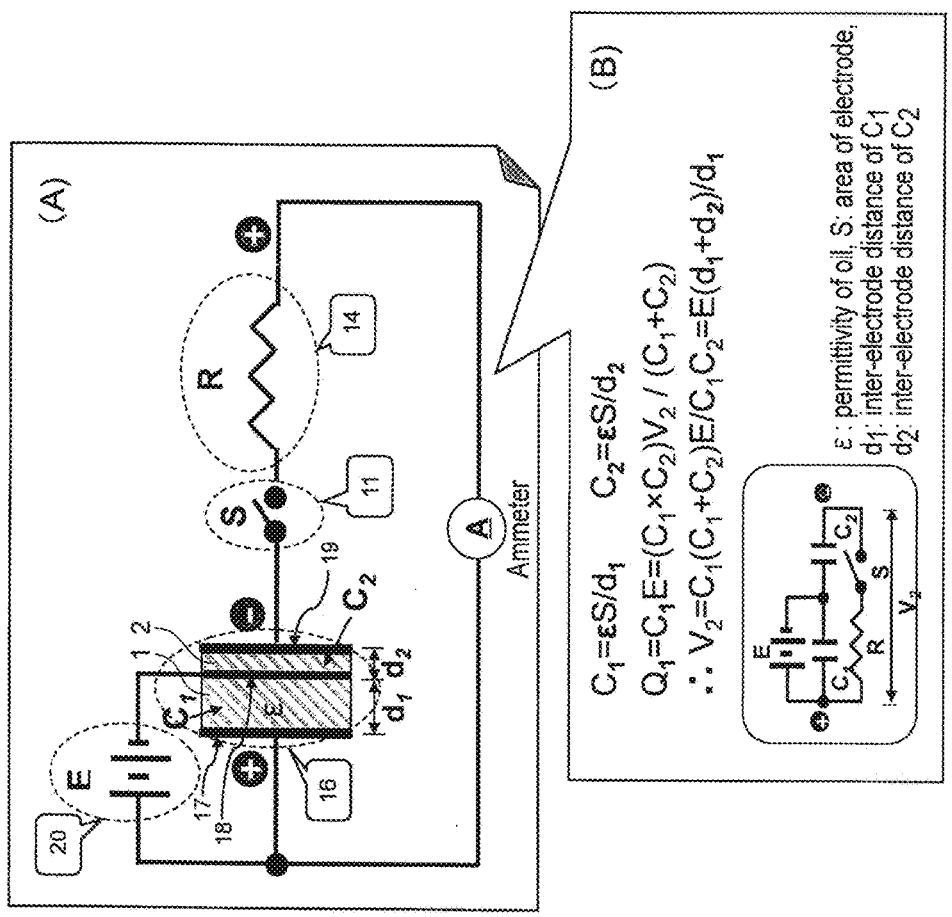
FIG. 8 shows an equivalent circuit for electrolyzing an aqueous electrolyte solution using the interface between an aqueous electrolyte solution side and an oil side as the negative electrode surface, in which (A) indicates a conceptual diagram of the Murahara circuit, and (B) indicates an electrical circuit (formula).
Figure 9:
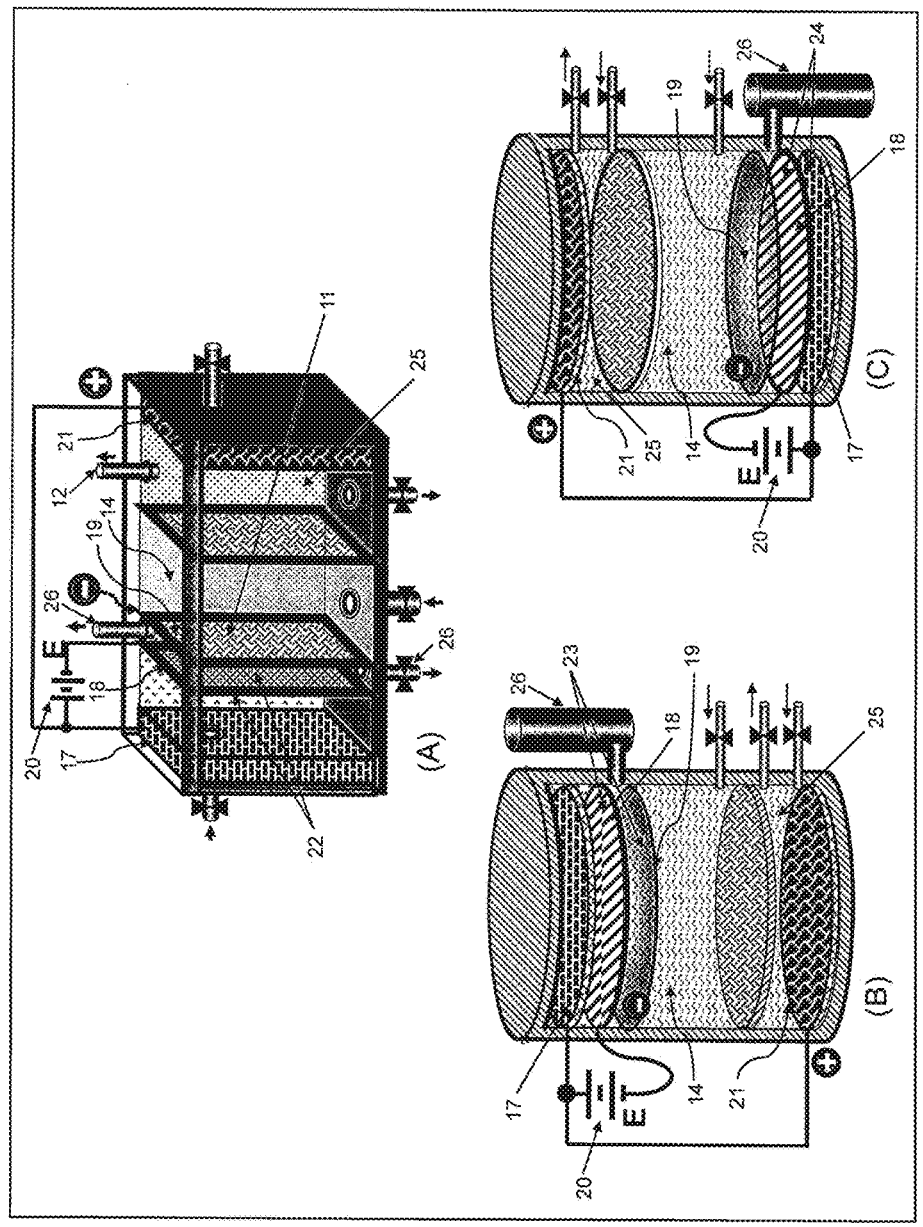
FIG. 9 is a conceptual diagram of an oil capacitor which uses the interface between an oil and an aqueous electrolyte solution as the negative electrode, in which (A) is a structural diagram of a virtual negative electrode using a water-repellent porous membrane, (B) is a structural diagram showing the case where the virtual negative electrode makes a vertical plane with respect to the earth's axis and the specific gravity of the oil is less than 1, and (C) is a structural diagram showing the case where the virtual negative electrode makes a vertical plane with respect to the earth's axis and the specific gravity of the oil exceeds 1.
Figure 10:
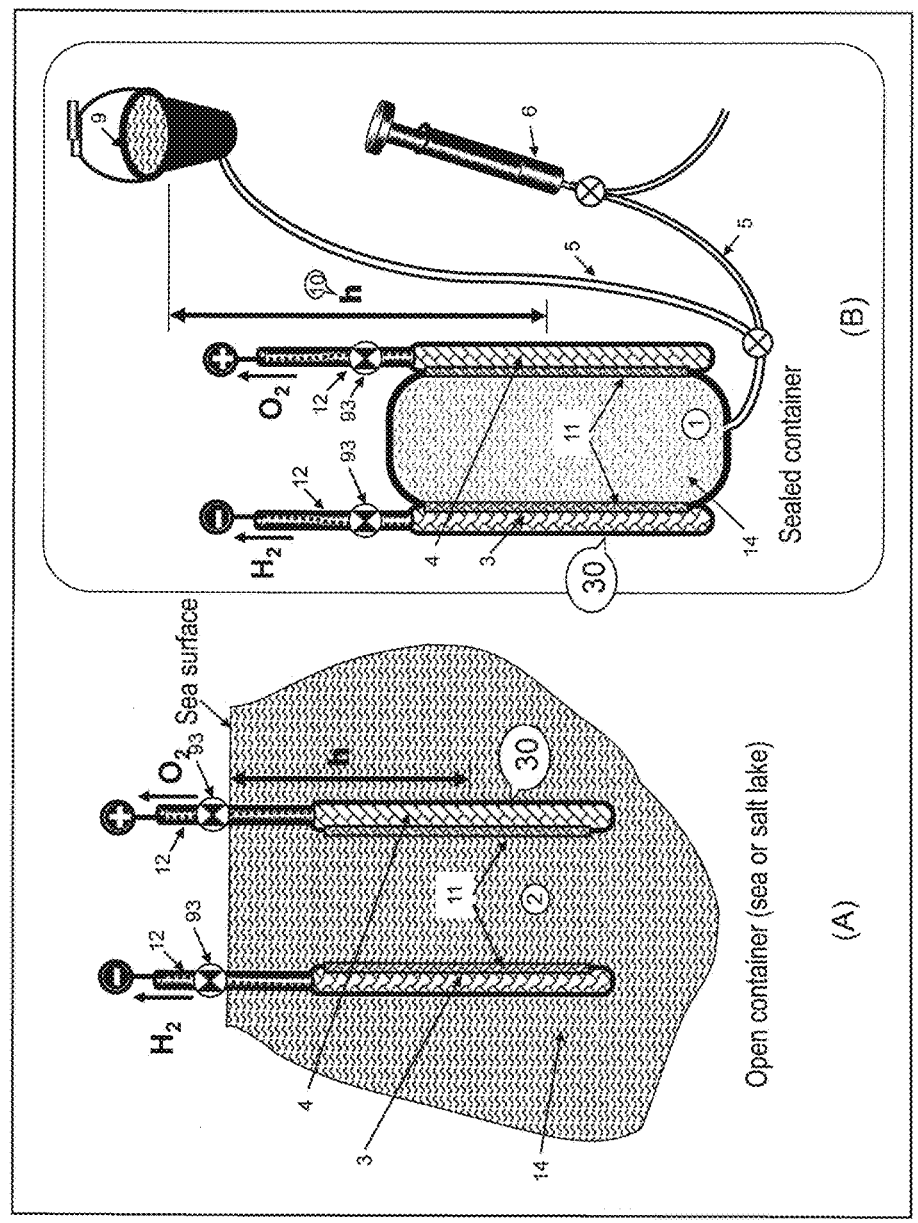
FIG. 10 is a diagram briefly showing a device for manufacturing hydrogen by sinking a gas-permeable electrode chamber under a sea surface and electrolyzing sea water directly, in which (A) shows an electrolytic device utilizing the hydraulic pressure under the sea surface and (B) shows the electrolytic device which pressurizes salt water on land.

FIG. 29 is a diagram briefly showing a hydrogen-producing apparatus used under sea surface. The negative electrode chamber 52 and the positive electrode chamber 53 each formed from a gas-permeable electrode chamber with a porous electrode, listed in FIG. 7, are sunk under a sea hydrogen.

In the hydrogen-producing apparatus 84 used under sea surface of FIG. 29, the outer walls of the positive and negative electrode chambers 52 and 53 were each formed from a vinyl-chloride resin pipe longitudinally cut into half and the opening made by the cutting in half was closed with a PTFE porous membrane (NTF-1133 of NITTO DENKO CORPORATION) 11 having a diameter of pores of 33 μm. As shown in a cross section of the negative electrode chamber 52, a stainless steel fiber 81 ("Web" Naslon (registered trademark) of Nippon Seisen Inc.) was put in the negative electrode chamber 52, and as shown in the sectional view of the positive electrode chamber 53 on the other side, a carbon cloth (carbon fiber) 82 was put in the positive electrode chamber 53. Further, the produced-gas collecting hose 12 was connected with an uppermost part of each of the electrode chambers 52 and 53 and positive and negative electrode lead lines were provided the insides of the collecting hoses 12, respectively.

Here, the aqueous electrolyte solution 14 is sea water and the average salinity concentration of sea water is 3.5% by weight. Moreover, the water-resistant pressure of the porous fluororesin film with a diameter of pores of 3 μm for an aqueous sodium chloride solution having a concentration of 3.5% by weight is known to be 380 mmHg from the relationship between the water-resistant pressure of the porous membrane and salt concentration shown in FIG. 28(A). Since the hydraulic pressure was 1 atmosphere (760 mmHg) at a depth of 10 meters in water, the potential head (h) 10 was set to about 5 m under the sea surface. The temperature of the sea water was 23° C. and the conductivity was 0.03 S/cm. Here, when the inter-electrode distance d (83) was fixed to 10 mm and a voltage of 1.5V was given between both electrodes, the power requirement per 1 m$^3$ of hydrogen and 0.5 m$^3$ of oxygen was 18.3 kWh. When the voltage between both electrodes was 2.5V or higher, chlorine was generated from the positive electrode. Note that when the hydrogen-producing apparatus 84 used here was placed on the land, and the inter-electrode distance d (83) was fixed to 10 mm and a voltage of 1.5V was given between both electrodes using an aqueous electrolyte solution (with a conductivity of 0.18 S/cm) in which the sodium chloride concentration was condensed to 25% by weight, the power requirement per 1 m$^3$ of hydrogen and 0.5 m$^3$ of oxygen was about 10 kWh.

Figure 30:
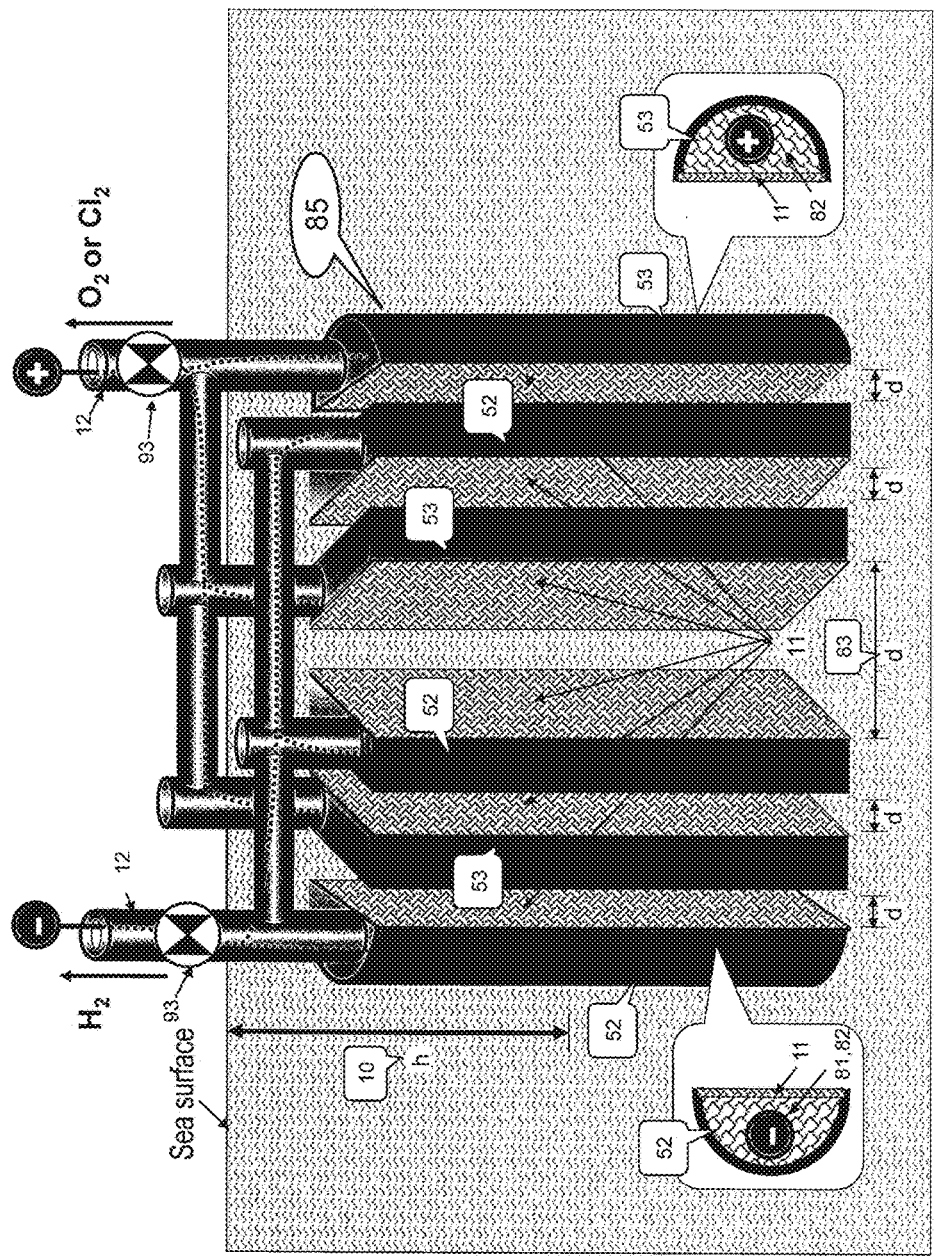
FIG. 30 is a diagram briefly showing a multistage type hydrogen-producing apparatus used under sea surface.

FIG. 30 is a diagram showing the structure of a multistage type hydrogen-producing apparatus used under sea surface, for electrolyzing sea water under a sea surface to produce hydrogen. The negative electrode chamber 52 and the positive electrode chamber 53 each made of a gas-permeable electrode chamber with a porous electrode, as listed in FIG. 7, are sunk under a sea surface, the sea water is electrolyzed directly to produce hydrogen. The average concentration of the sea water used as the aqueous electrolyte solution 14 is 3.5% by weight. The water-resistant pressure for an aqueous sodium chloride solution having a concentration of 3.5% is known to be 380 mmHg from the relationship between the water-resistant pressure of the porous fluororesin film with a diameter of pores of 3 μm and salt concentration shown in FIG. 28(A). Thus, the multistage type hydrogen-producing apparatus 84 used under sea surface was descended to about 5 m under the sea surface (potential head (h) 10) for test.

In a multistage type hydrogen-producing apparatus 85 of FIG. 30, a PTFE porous membrane (NTF-1133 of NITTO DENKO CORPORATION) having a diameter of pores of 3 μm was used as a fluororesin-made water-repellent porous membrane 11 for positive and negative electrode chambers 52 and 53, and the outer walls of the positive and negative electrode chambers 52 and 53 were each formed of vinyl chloride. A product gas collecting hose 12 was connected to the uppermost parts of the electrode chambers 52, and the negative electrode chambers 52 and the positive electrode chambers 53 are arranged successively alternately. Thus, hydrogen gas produced at each of the negative electrode chambers 52 and oxygen produced at the positive electrode chambers 53 are collected at once through the pipe. In this test, the multistage type hydrogen-producing apparatus 84 used under sea surface includes three sets of hydrogen-collecting negative electrode chambers 52 and oxygen-collecting positive electrode chambers 53 arranged in parallel with a distance (83) between adjacent electrodes being fixed to 10 mm. The electrode material of the negative electrode chambers 52 was a stainless steel fiber 81 ("Web" Naslon (registered trademark) of Nippon Seisen Inc.), whereas the positive electrodes are electrode chambers of the same structure as that of the negative electrodes, in which a carbon cloth (carbon fiber) 82 was enclosed. Since it is in the sea water, the salt concentration of the electrolytic was 3.5% by weight, the temperature of the sea water was 23° C. and the conductivity was 0.03 S/cm. When a voltage of 1.5V was applied between both electrodes, the power requirement per 1 m$^3$ of hydrogen and 0.5 m$^3$ of oxygen was about 17 kWh.

Figure 11:
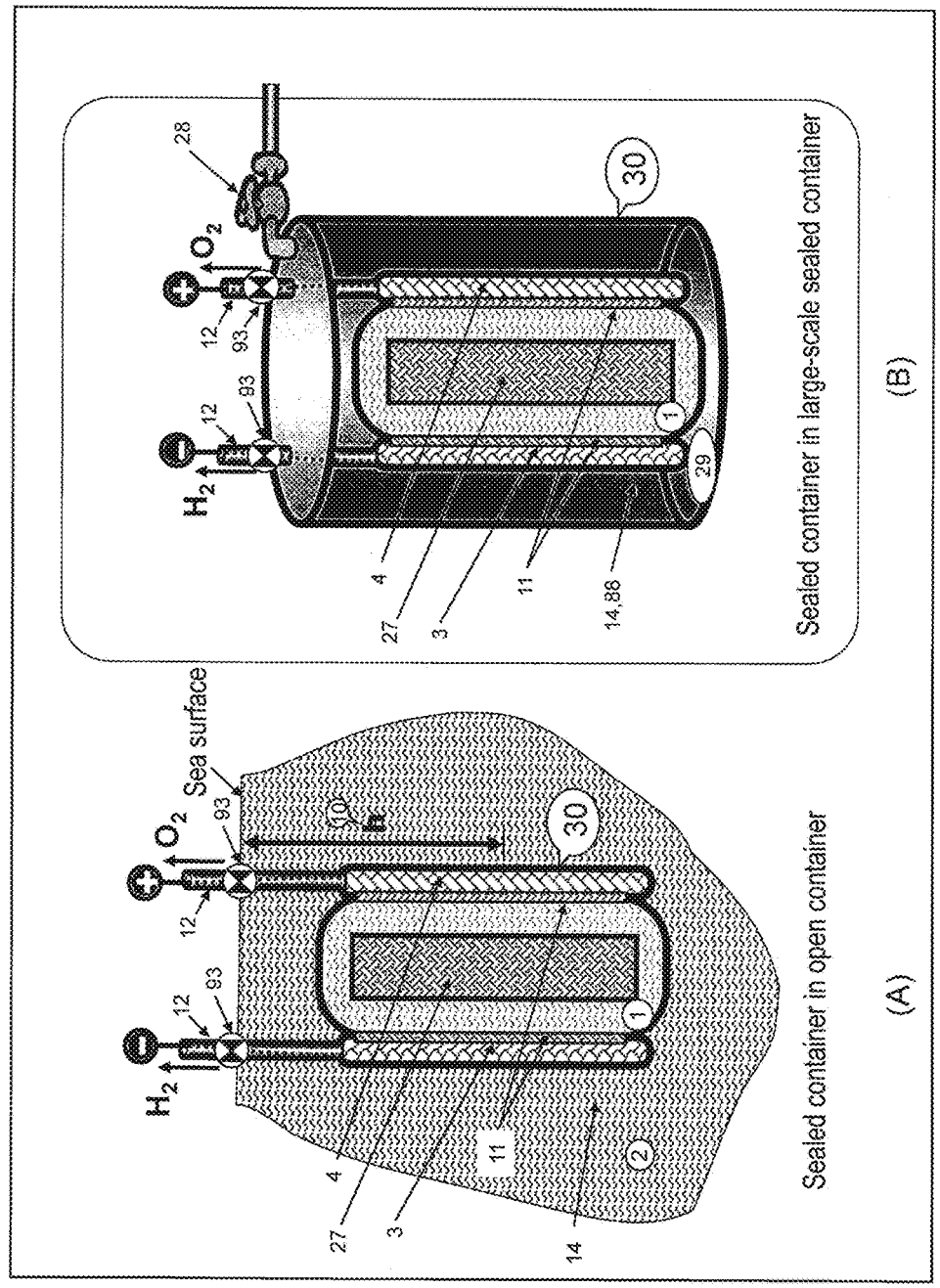
FIG. 11 is a diagram briefly showing a hydrogen-producing apparatus which electrolyzes water in a sealed container inserted into an open container or a large-scale sealed container, in which (A) shows an electrolytic device using the hydraulic pressure under the water surface of a freshwater lake, and (B) shows the electrolytic device pressurizing with tap water.
Figure 31:
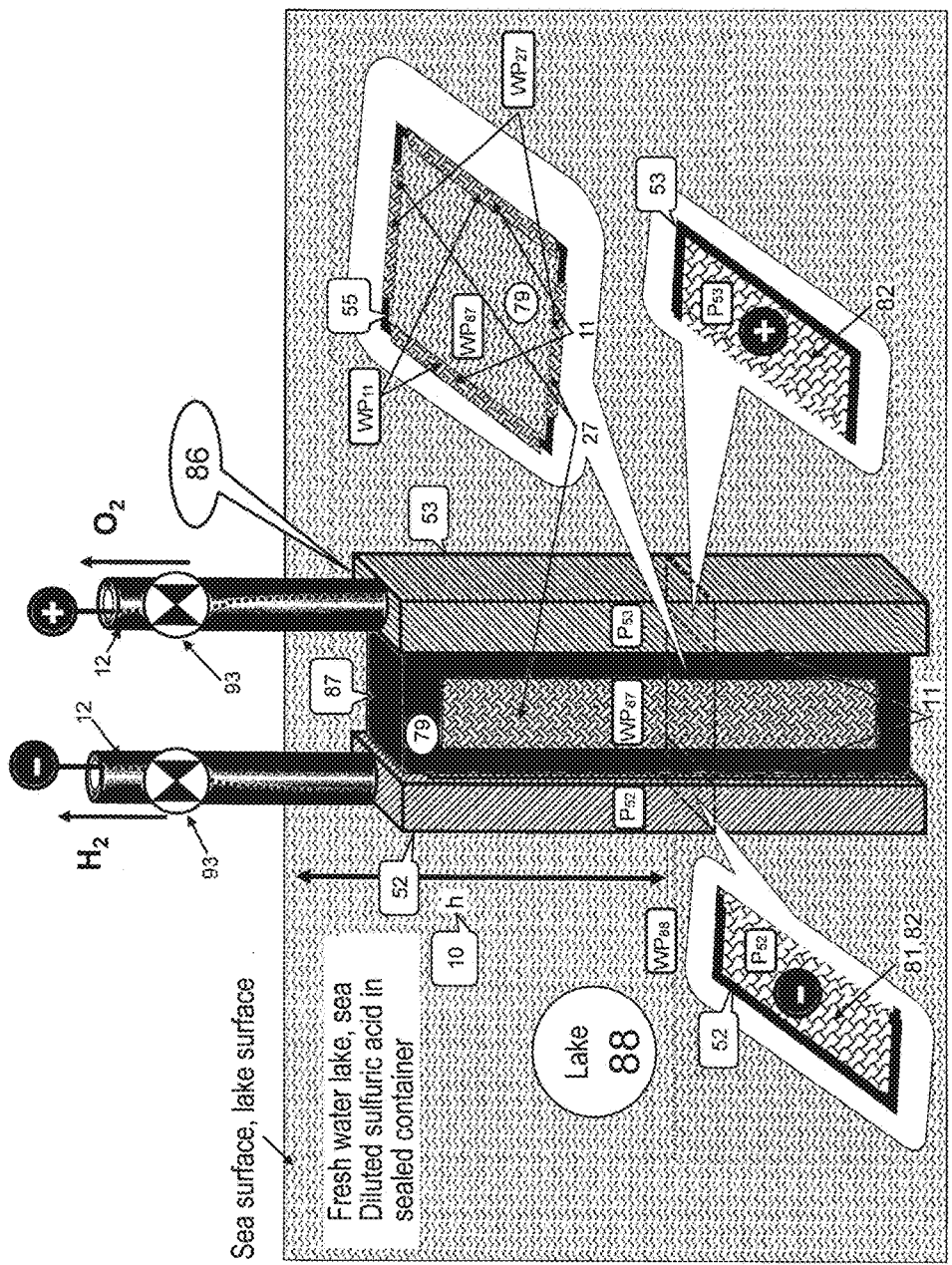
FIG. 31 is a diagram briefly showing a hydrogen-producing apparatus used under lake surface.

FIG. 31 is a diagram showing the structure of a hydrogen-producing apparatus used under lake water surface. The principle is, as shown in FIG. 11, that freshwater is supplied with pressure from an outer wall of a sealed container into a high-concentration aqueous electrolyte solution sealed hermetically in the sealed container of a water-repellent porous membrane through a water-repellent porous membrane for supplying the aqueous solution with pressure, to directly produce hydrogen and oxygen or chlorine at high efficiency. The sealed container of a water-repellent porous membrane, filled with the high concentration aqueous electrolyte solution (high-solubility and high-conductivity aqueous electrolyte solution) is sunk into an open container such as a freshwater lake, pond or sea. Thus, while freshwater or a low-concentration aqueous electrolyte solution is being supplied with pressure from the water-repellent porous membrane for supplying aqueous solution with pressure, attached to the sealed container, the aqueous solution is electrolyzed to produce hydrogen.

FIG. 31 shows a hydrogen-producing apparatus 86 under the surface of a lake (or sea) comprising a quadrangular prism-shaped sealed container 87 interposed between a negative electrode chamber 52 and a positive electrode chamber 53. The quadrangular prism-shaped sealed container 87 includes four side surfaces, two of which (those in contact with the positive and negative electrode chambers 52 and 53) are made from a water-repellent porous material 11, and at least one of the other surfaces is made from a water-repellent porous membrane (for freshwater permeation) 27. In the quadrangular prism-shaped sealed container 87, about 3-normality sulfuric acid and 4-normality aqueous caustic soda solution are contained to reinforce electrolytic dissociation. The freshwater 88 or low concentration aqueous electrolyte solution entering the water-repellent porous membrane 27 of the freshwater-osmosis quadrangular prism-shaped sealed container 87 from outside is electrolyzed by the positive and negative electrode chambers to produce hydrogen and oxygen. The acid and alkali used here are called ionization catalysts. It should be noted that the water-resistant pressure in the aqueous sodium chloride solution of the water-repellent porous fluororesin film (having a diameter of pores of 33 µm) of FIG. 28(A) was 430 mmHg with water and 330 mmHg with 10% of aqueous sodium chloride solution, and thus there was a pressure difference of 100 mmHg. Here, the diameter of the pores of the water-repellent porous fluororesin film (electrode isolation film) 11 is set less by selection than that of the water-repellent porous membrane (for freshwater permeation) 27 or the water-repellent porous fluororesin film (electrode isolation film) 11 is subjected to a treatment of imparting hydrophilic properties, to equalize or approximate the water-resistant pressure of the water-repellent porous fluororesin film (electrode isolation film) 11, due to the salt concentration to the water-resistant pressure of the water-repellent porous membrane (for freshwater permeation) 27, due to freshwater, which is a feature of the present invention. Note that the hydrogen-producing apparatus 86 is applicable also to seas and hot spring water other than lake. With the device structure of the present invention, since the product gases from the positive and negative electrode chambers are collected on the water surface by suctioning the gases on the water surface. Therefore, if the gas pressures of the positive and negative electrode chambers are suctioned each with a vacuum pump, it is not necessary to descend the hydrogen-producing apparatus 87 to the head position. Moreover, since the gas pressures of the positive and negative electrode chambers 52 and 53 are lower than the hydraulic pressure of freshwater or a rare electrolyte entering the water-repellent porous membrane (for freshwater permeation) 27, sulfuric acid never flows out into external freshwater from the water-repellent porous membrane (for freshwater permeation) 88 of the sealed container. Further, since the gas pressure of each of the positive and negative electrode chambers can be controlled by suctioning the gas from the positive or negative electrode chamber with a vacuum pump, the water-repellent porous fluororesin films (electrode isolation films) 11 and 27 may be of the same material. Furthermore, it is required to set the hydraulic pressure outside the sealed container being applied to the water-repellent porous membrane (for freshwater permeation) 27 to high, and the gas pressure on the electrode chamber side to low, thereby creating a pressure difference. Furthermore, in order to maintain the pressure on the gas generation side to a certain level or below, it is easiest to provide a pressure regulating valve 93 in front of the product gas extraction outlet to adjust it by the pressure of the gas generated by the gas-permeable electrode chambers 52 and 53. With use of the hydrogen-producing apparatus 86 under the surface of a lake, having the above-described structure, in which 1 to 5-normality sulfuric acid or 1 to 10-normality caustic soda is contained in the quadrangular prism-shaped sealed container 87, when the freshwater 88 equivalent to the production amounts of hydrogen and oxygen is supplied from outside for electrolysis, it is possible to product hydrogen and oxygen continuously. In the present invention, this sulfuric acid and caustic soda are referred to as ionization catalysts. In this test, a 10 to 100-mm-wide quadrangular prism-shaped sealed container 87 was disposed between positive and negative electrode chambers, and as the electrode material of the negative electrode chamber 52, a stainless steel fiber 81 ("Web" Naslon (registered trademark) of Nippon Seisen Inc.) was used as shown in its cross section, whereas in the positive electrode, a carbon cloth (carbon fiber) 82 was enclosed. Measurements were carried out for two separate cases where 2.5-normality-sulfuric acid and 2.5-normality-caustic soda are sealed in the quadrangular prism-shaped type sealed container 87. The hydrogen-producing apparatus 86 was sunk into a 3-m-deep pool, and while evacuating the negative electrode chamber 52 and the positive electrode chamber 53 via the pressure-regulating valves 93 respectively to maintain the gas-pressure of each to 200 to 400 mmHg. Thus, the efficiency of hydrogen production was measured. The conductivity of sulfuric acid to be put into the high-concentration aqueous electrolyte solution 79 was 0.8 S/cm. To compare, the conductivity of 2.5-normality caustic soda was 0.3 S/cm. Here, when a voltage of 1.5V was applied between both electrodes of the hydrogen-producing apparatus 86, the power requirement per 1 $m^3$ of hydrogen and 0.5 $m^3$ of oxygen for the case where the high-concentration aqueous electrolyte solution was sulfuric acid was 5.2 kWh, whereas it was 2.3 kWh for the case of caustic soda.

Figure 32:
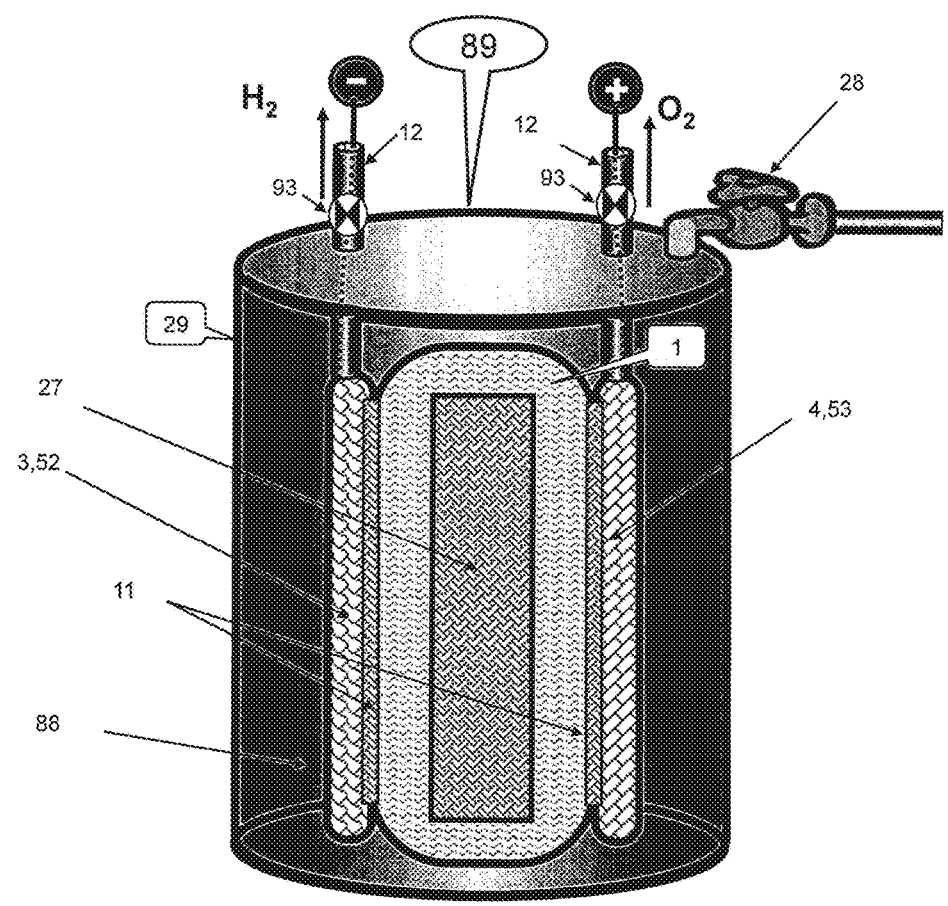
FIG. 32 is a diagram briefly showing the simple hydrogen-producing apparatus using tap water pressure.

FIG. 32 is a diagram showing the structure of a simple hydrogen-producing apparatus utilizing the pressure of tap water. FIG. 11(B) shows the principle thereof, in which a sealed container made of a water-repellent porous membrane is inserted in a large-sized sealed container, and tap water is supplied thereto while pressurizing the water at a pressure higher than or equal to the water-resistant pressure of the water-repellent porous membrane, thus producing hydrogen continuously.

In the simple hydrogen-producing apparatus 89 utilizing the pressure of tap water, shown in FIG. 32, after a sealed container 1 of a water-repellent porous membrane was inserted to a large-sized sealed container 29, the hydraulic pressure of tap water 28 is pressurized further with a pressure higher than or equal to the water-resistant pressure of the water-repellent porous membrane (for freshwater permeation) 27 and at the same time, freshwater (tap water) 88 is supplied thereto with pressure through the water-repellent porous membrane (for freshwater permeation) 27 to maintain the about 3N (about 8%) aqueous sulfuric acid solution. Thus, electrolysis is carried out in the positive and negative electrode chambers 3 and 4 (gas-permeable electrode chambers 52 and 53) simultaneously, and hydrogen is collected from a product gas collecting hose 12 of the negative electrode chamber 3, whereas oxygen from the product gas collecting hose 12 of the positive electrode chamber 4. For the gas collection, in order to adjust the pressure of the freshwater (tap water) 88 and to maintain the pressure on the gas producing side to a certain level or less, a pressure regulating valve 93 is provided in front of the product gas extraction outlet, as a control mechanism to adjusts the pressure of the gas produced by each of the gas-permeable electrode chambers 52 and 53. Especially, sulfuric acid having a concentration of 2 to 5 has the highest conductivity, and therefore, for maintaining this concentration, a pressurization device is additionally provided to adjust the injection pressure of freshwater at the faucet to balance between hydrogen and oxygen produced, for the chambers by means of vacuum evacuation and compressor.

Figure 33:
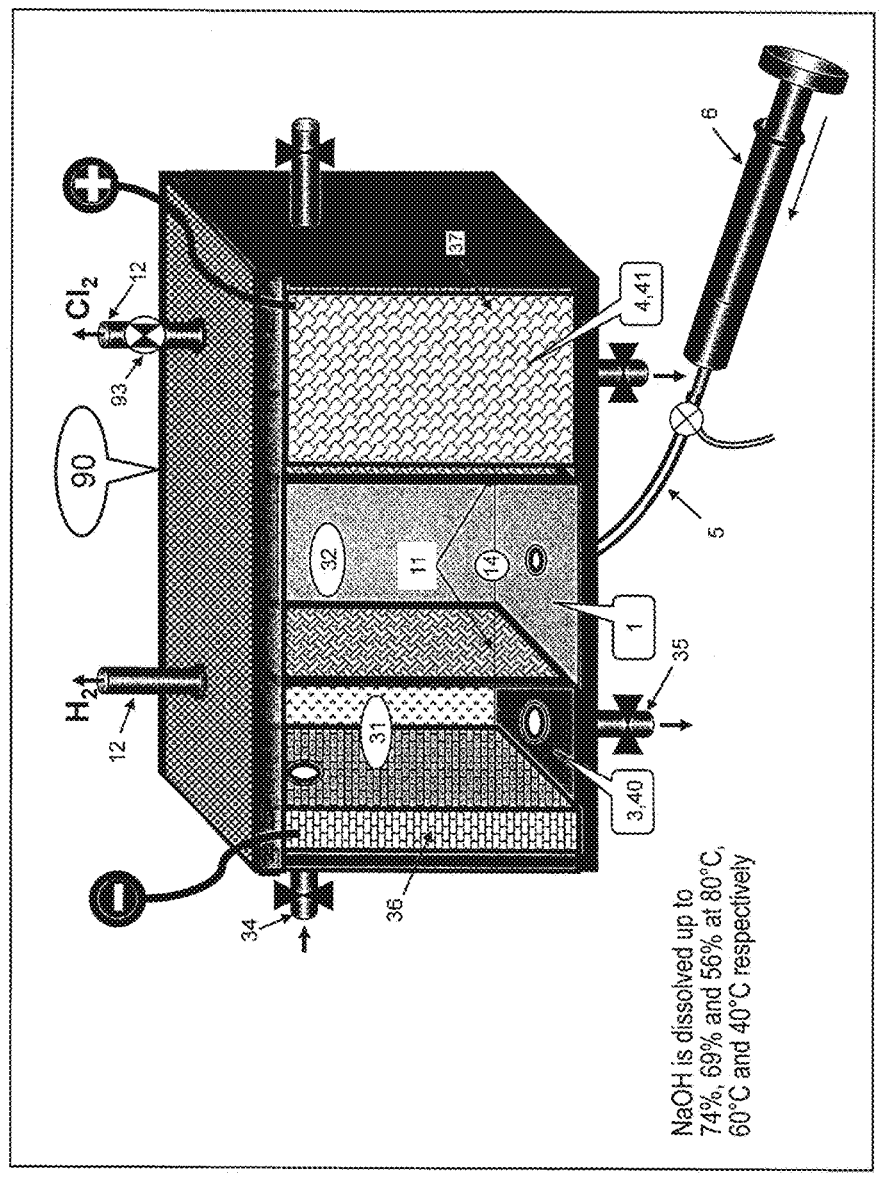
FIG. 33 is a diagram briefly showing a device which produces caustic soda and gaseous chlorine directly from an aqueous sodium chloride solution.

FIG. 33 shows a device for producing caustic soda and chlorine directly from an aqueous sodium chloride solution. FIGS. 12(A) and (B) show the principle thereof, in which a pressure equal to the water-resistant pressure of the water-repellent porous membranes constituting the sealed container, attached to the positive and negative electrode chambers, respectively, is applied to an aqueous sodium chloride solution during electrolysis, and thus caustic soda is produced in the negative electrode chamber. A pressure equal to the water-resistant pressure is applied to the water-repellent porous membranes via the aqueous sodium chloride solution.

Figure 18:
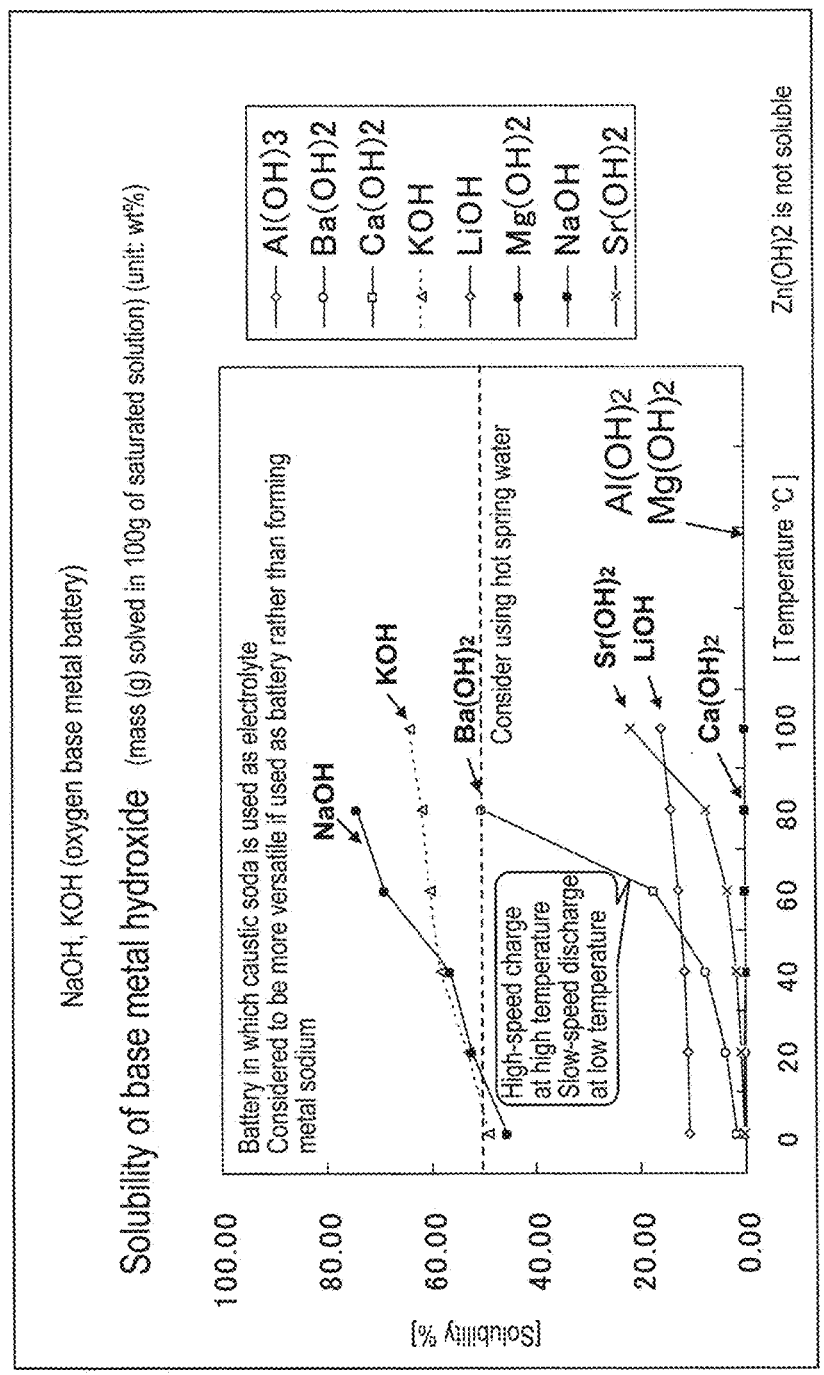
FIG. 18 shows the relationship between the solubility and temperature of hydroxylated base metal.

As shown in FIG. 33, a device 90 for producing caustic soda and chlorine directly from an aqueous sodium chloride solution comprises, at its center, a sealed container 1 defined by two water-repellent porous membranes 11 placed apart from each other. A negative electrode chamber 3 provided on one side of the sealed container 1 constitutes an electrode chamber 40 to be filled with water, and a negative electrode plate 36 of carbon or nickel is also provided. A positive electrode chamber 4 provided on another side of the sealed container 1 constitutes a gas-permeable electrode chamber 41, in which a porous electrode material is provided. Then, the sealed container 1 is filled with an aqueous sodium chloride solution 32 having a concentration of 26% by weight. The solubility of sodium chloride is hardly influenced by atmospheric temperature, but caustic soda to be produced is influenced by atmosphere temperature. As shown in FIG. 18, the solubility of caustic soda at a temperature of 40° C. is 56%, and at a temperature of 80° C. is 74%, and thus the solubility increases, as the temperature is higher; therefore in order to manufacture a high-concentration caustic soda 31, it is desirable to pour hot water into the electrode chamber 40, or to heat the electrode chamber 40 with a heater. In this experiment, as a simple method, hot water of 100° C. or less was poured in from the water supply inlet 34 of the negative electrode chamber 3. One possible idea devised here is to raise the electrolytic efficiency by adding diluted caustic soda 31 in advance to the water in the negative electrode chamber 3 at the start of electrolysis. Here, the water-repellent porous membrane 11 is pressurized with a pressure equal to the water-resistant pressure with the pressure-applying member 6 while maintaining the concentration of the aqueous sodium chloride solution 32 at 26% at all times to produce the caustic soda 31 at the negative electrode chamber 40 and collect concentrated caustic soda from the negative electrode product collecting port 35 and hydrogen gas with a product gas collecting hose 12 attached to the uppermost part. Moreover, gaseous chlorine is collected with the product gas collecting hose 12 attached to the uppermost part of the positive electrode chamber 4. In order to maintain the pressure on the gaseous chlorine producing side at a certain level or below, a pressure regulating valve 93 is provided in front of a product gas extraction port, which adjust the gas pressure of the caustic soda producing chamber 31 not to become 1 atmosphere or higher. When a voltage of 4V was applied between both electrodes and the current density was set to 20 A, the production amount of caustic soda was 3 kWh per kg.

Figure 34:
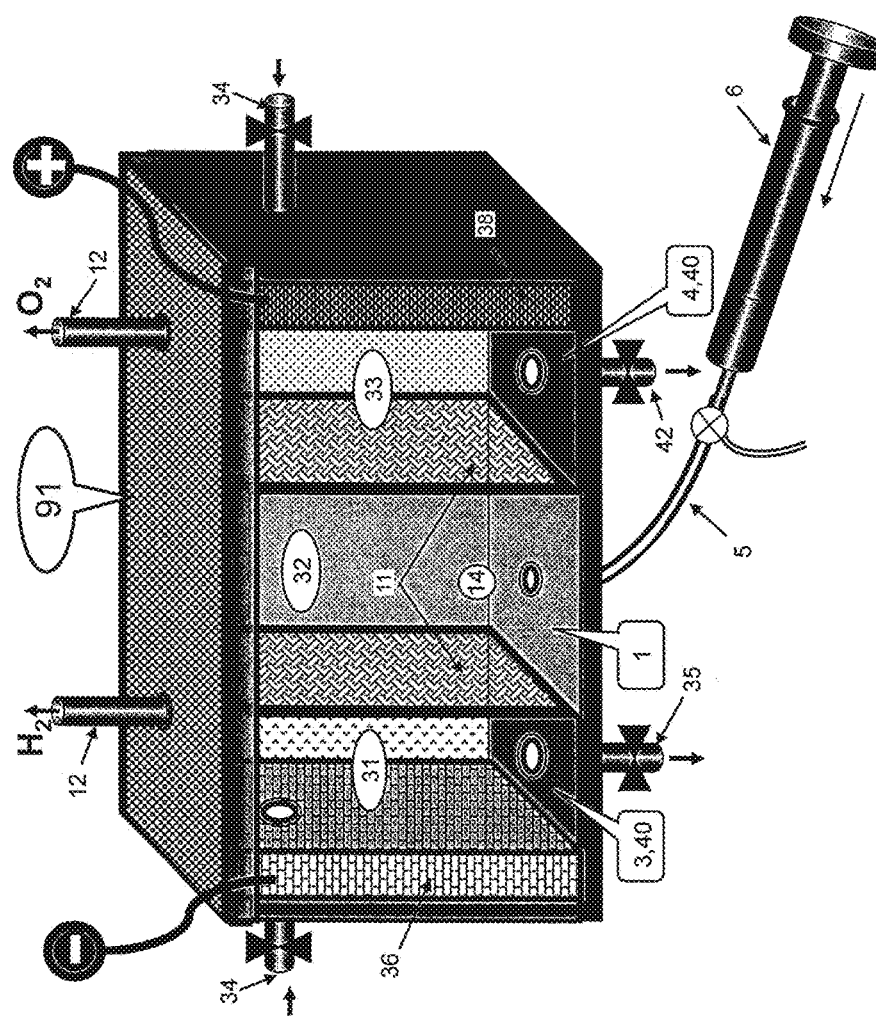
FIG. 34 is a diagram briefly showing a device which produces caustic soda and hydrochloric acid directly from an aqueous sodium chloride solution.

FIG. 34 shows a device for producing caustic soda and hydrochloric acid directly from an aqueous sodium chloride solution. FIG. 12(B) shows the principle thereof, in which a pressure equal to the water-resistant pressure of the water-repellent porous membranes constituting the sealed container, attached to the positive and negative electrode chambers, respectively, is applied to an aqueous sodium chloride solution during electrolysis, and thus caustic soda is produced in the negative electrode chamber. A pressure equal to the water-resistant pressure is applied to the water-repellent porous membranes via the aqueous sodium chloride solution.

A device 91 for producing caustic soda and chlorine directly from an aqueous sodium chloride solution shown in FIG. 34 comprises, at its center, a sealed container 1 defined by two water-repellent porous membranes 11 placed apart from each other. A negative electrode chamber 3 provided on one side of the sealed container 1 constitutes an electrode chamber 40 to be filled with water, and a negative electrode plate 36 of carbon or nickel is also provided. A positive electrode chamber 4 provided on another side of the sealed container 1 constitutes also an electrode chamber 40 to be filled with water, in which a positive electrode plate of carbon is provided. Then, the sealed container 1 is filled with an aqueous sodium chloride solution 32 having a concentration of 26% by weight. Then, water is poured in from the water supply inlet 34 of the positive electrode chamber 4 and hot water of 100° C. or less is poured in from the water supply inlet 34 of the negative electrode chamber 3. Further, at the start of electrolysis, diluted caustic soda 31 is added in advance to the water in the negative electrode chamber 3 and hydrochloric acid is added in advance to the water in the positive electrode chamber 4, thus raising the electrolytic efficiency. Here, the water-repellent porous membrane 11 is pressurized with a pressure equal to the water-resistant pressure with the pressure-applying member 6 while maintaining the concentration of the aqueous sodium chloride solution at 26% at all times to produce the caustic soda 31 at the negative electrode chamber and collect concentrated caustic soda from the negative electrode product collecting port 35 and hydrogen gas with a product gas collecting hose 12 attached to the uppermost part. Moreover, concentrated hydrochloric acid is collected from the positive electrode product collecting port (concentrated acid outlet) 42 of the positive electrode chamber 4, and oxygen gas is collected with the product gas collecting hose 12 attached to the uppermost part thereof. The caustic soda 31 is produced in the electrode chamber 40 of the negative electrode chamber 3 and the hydrochloric acid 33 is produced in the electrode chamber 41. Both of these have high electric conductivities, and therefore the aqueous sodium chloride solution 32, which is the aqueous electrolyte solution 14 in the sealed container 1 isolated by the water-repellent porous membrane 11 is electrolyzed efficiently by the pressurization of the aqueous electrolyte solution at the water-resistant pressure.

Figure 13:
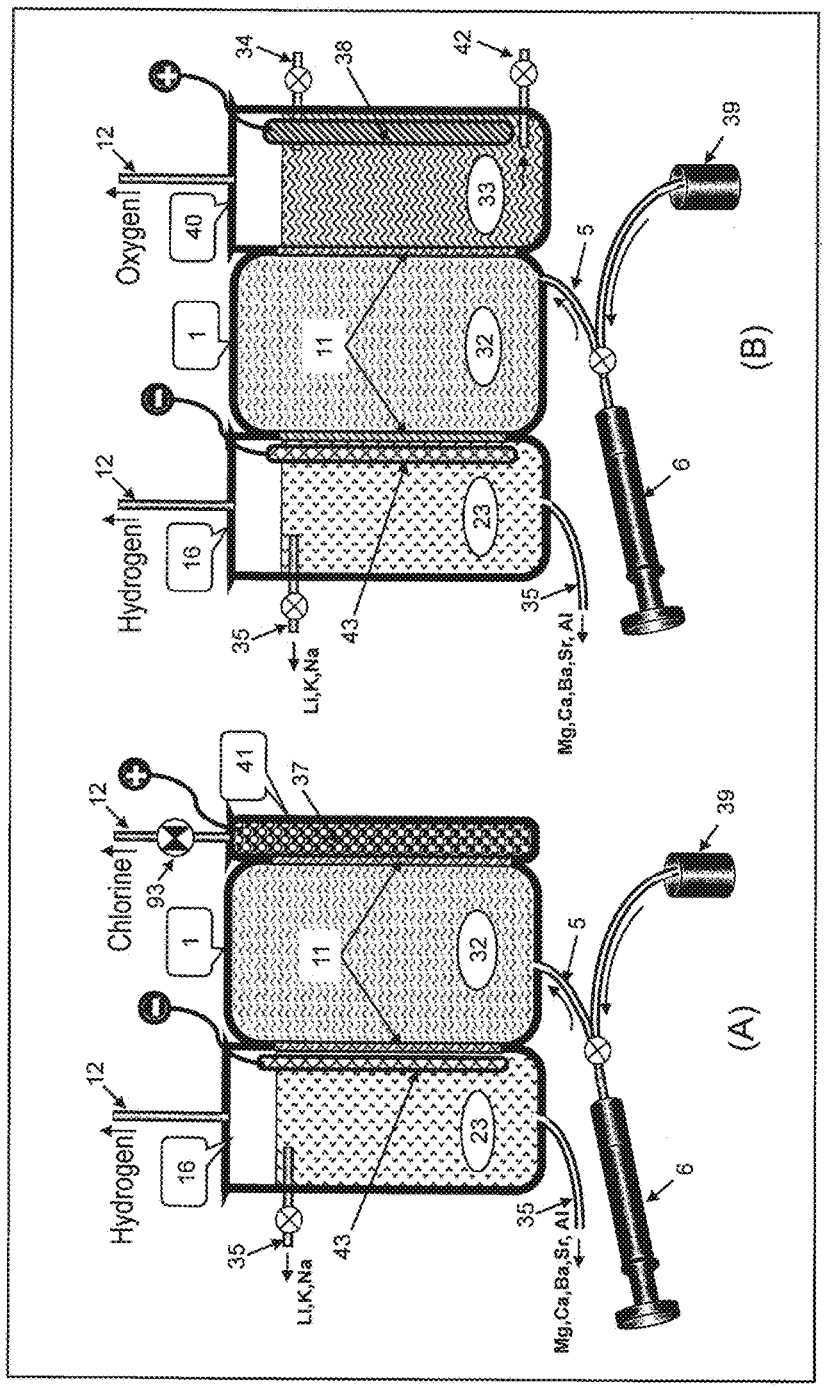
FIG. 13 is a diagram briefly showing a base metal collecting device, in which (A) shows a device which manufactures a base metal in an oil tank of an oil-filled negative electrode chamber, and a positive electrode product gas (chlorine) on a positive electrode, and (B) shows a device which manufactures a base metal in an oil tank of an oil-filled negative electrode chamber, and an acid (hydrochloric acid) on a positive electrode.
Figure 35:
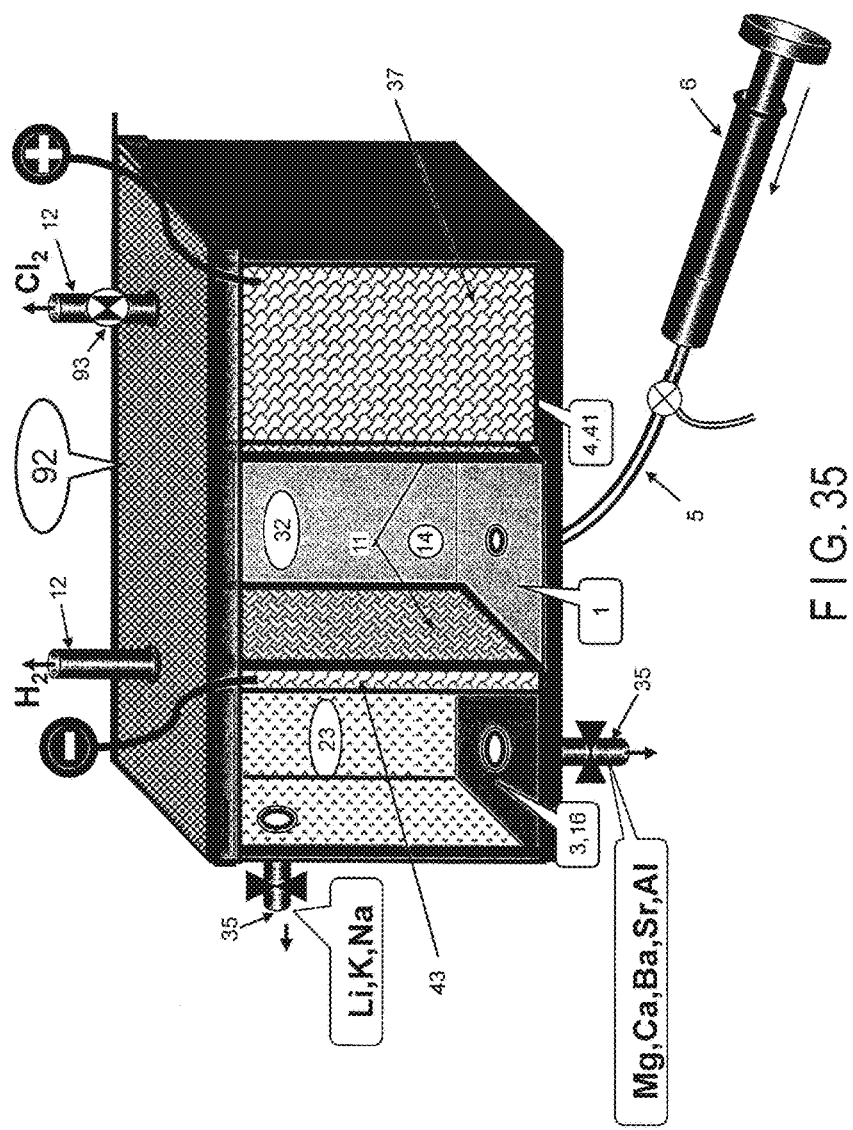
FIG. 35 is a diagram briefly showing a device which produces base metal directly from an aqueous base metal chloride solution.

FIG. 35 shows a device for producing a base metal element directly from an aqueous base metal chloride solution. FIG. 13(A) show a principle thereof, in which a carbon-made porous electrode is brought into contact with a negative electrode side of a sealed container through an isolation film made from a water-repellent porous membrane, and a back surface thereof is filled with an oil, thus collecting base metals having a specific gravity lighter than that of the oil (namely, Li, K, Na) from the upper part, and base metals having a specific gravity heavier than that of the oil 23 (namely, Mg, Ca, Ba, Sr, Al) from the lowermost part.

Figure 19:
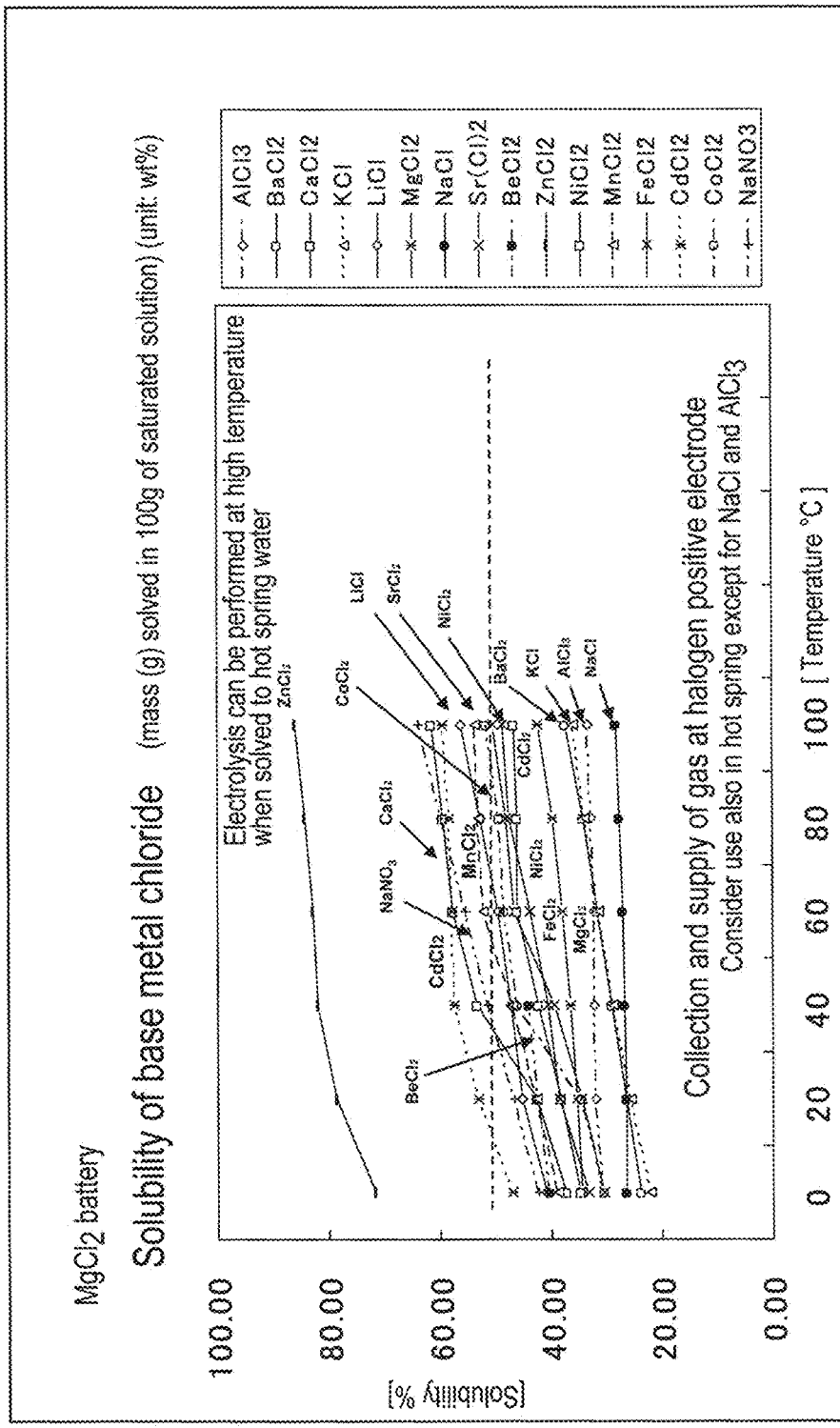
FIG. 19 shows the relationship between the solubility and temperature of base metal halide (chloride).

The base metal element-producing device 92 shown in FIG. 35 accommodates one kind selected from aqueous solutions of, for example, NaCl, KCl, LiCl, $MgCl_2$, $CaCl_2$, $BaCl_2$, $SrCl_2$ and $AlCl_3$ as a chloride corresponding to a base metal element desired to be produced in the sealed container 1 defined by the water-repellent porous membrane 11. As for the base metal chlorides, the solubility tends to rise as the solution temperature becomes high except for NaCl, which does not have temperature dependency, as shown in FIG. 19. For example, if the liquid temperature of the aqueous base metal chloride solution 32 in the sealed container 1 is warmed up with an internal heater to 60° C., the solubilities of NaCl, KCl, LiCl, $MgCl_2$, $CaCl_2$, $BaCl_2$, $SrCl_2$ and $AlCl_3$ are 27%, 31%, 50%, 38%, 58%, 32% 47% and 32%, respectively. It can be understood from these results that the pressure should be raised to the water-resistant pressure while the liquid temperature of the aqueous base metal chloride solution 32 is raised to 25 to 80° C. to increase the concentration to the saturation solubility, to start electrolysis. The negative electrode chamber 3 of the base metal element-producing device 92 shown in FIG. 35 constitutes the electrode chamber 16 filled with an oil, in which a mesh negative electrode 43 of carbon fiber is used as the electrode and gas oil whose specific gravity is 0.8 is used for the oil 23. On the other hand, the positive electrode chamber 4 constitutes a gas-permeable electrode chamber 41, in which a positive electrode 37 of carbon fiber is used and gaseous chlorine is collected from the positive electrode chamber 4 with the product gas collecting hose 12. When LiCl is used as the aqueous base metal chloride solution 32, about 50% of LiCl is electrolyzed at 80° C. because the solubility is 53% at 80° C., the melting points of Li is 179° C. and the specific gravity is 0.54 (FIG. 16), and thus metal Li floats around the uppermost part of the gas oil 23 of the negative electrode chamber 3, which is collected from the negative electrode product collecting port 35 provided at the uppermost part of the negative electrode chamber 3. On the other hand, gaseous chlorine is collected with the product gas collecting hose 12 at the uppermost part of the positive electrode chamber. In order to maintain the pressure on the gaseous chlorine producing side at a certain level or below, a pressure regulating valve 93 is provided in front of the product gas extraction port. In a preliminary test, an aqueous sodium chloride solution concentrated to 28% was subjected to a treatment while applying a voltage of 4 to 5V between the positive and negative electrodes at 25° C. and a current density 10A for 1 hour, and thus 8 g of metallic sodium was deposited in the gas oil filled in the electrode chamber 16.

Figure 36:
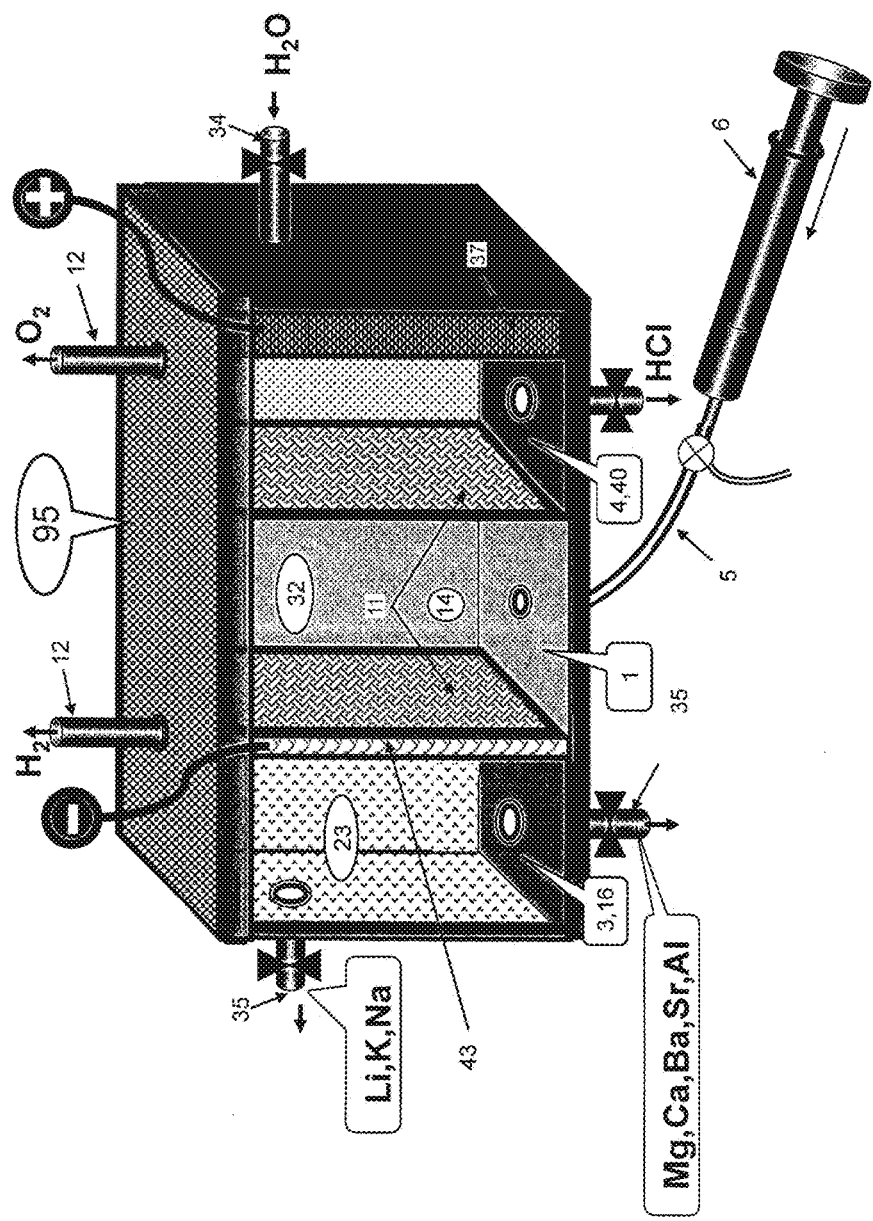
FIG. 36 is a diagram briefly showing a device which produces base metal element and hydrochloric acid directly from an aqueous base metal chloride solution.

FIG. 36 is a device for producing a base metal element and hydrochloric acid directly from an aqueous base metal chloride solution. FIGS. 13(A) and (B) shows a principle thereof, in which a carbon-made porous electrode is brought into contact with a negative electrode side of a sealed container via an isolation film of a water-repellent porous membrane, and a back surface is filled with an oil, and thus a base metal whose specific gravity is lighter than that of the oil (namely, Li, K, Na) are collected from the upper portion, whereas a base metal whose specific gravity is heavier than that of the oil 23 (namely, Mg, Ca, Ba, Sr, Al) is collected from the lowermost portion. The method of producing a negative electrode product is as described above. On the other hand, hydrochloric acid is made by the positive electrode in the following manner. That is, a water-filled electrode chamber 40 is adopted as the positive electrode chamber 4 of the device 95 of FIG. 36, for producing base metal element and hydrochloric acid directly, and a diluted aqueous hydrochloric acid solution is added in advance to water supplied from the water supply inlet 34 to cause a reaction between anion and water. Then, an ionic reaction ($2Cl^-+2H_2O \rightarrow 2HCl+O_2$) is caused by electrolysis between the mesh negative electrode plate 43 and the positive electrode plate 38 via the water-repellent porous membrane 11. Thus, the device has such a structure that the acid (hydrochloric acid) 33 produced here is collected from the strong acid (hydrochloric acid) extraction port 42, whereas the oxygen is collected from the product gas collecting pipe 12.

Figure 14:
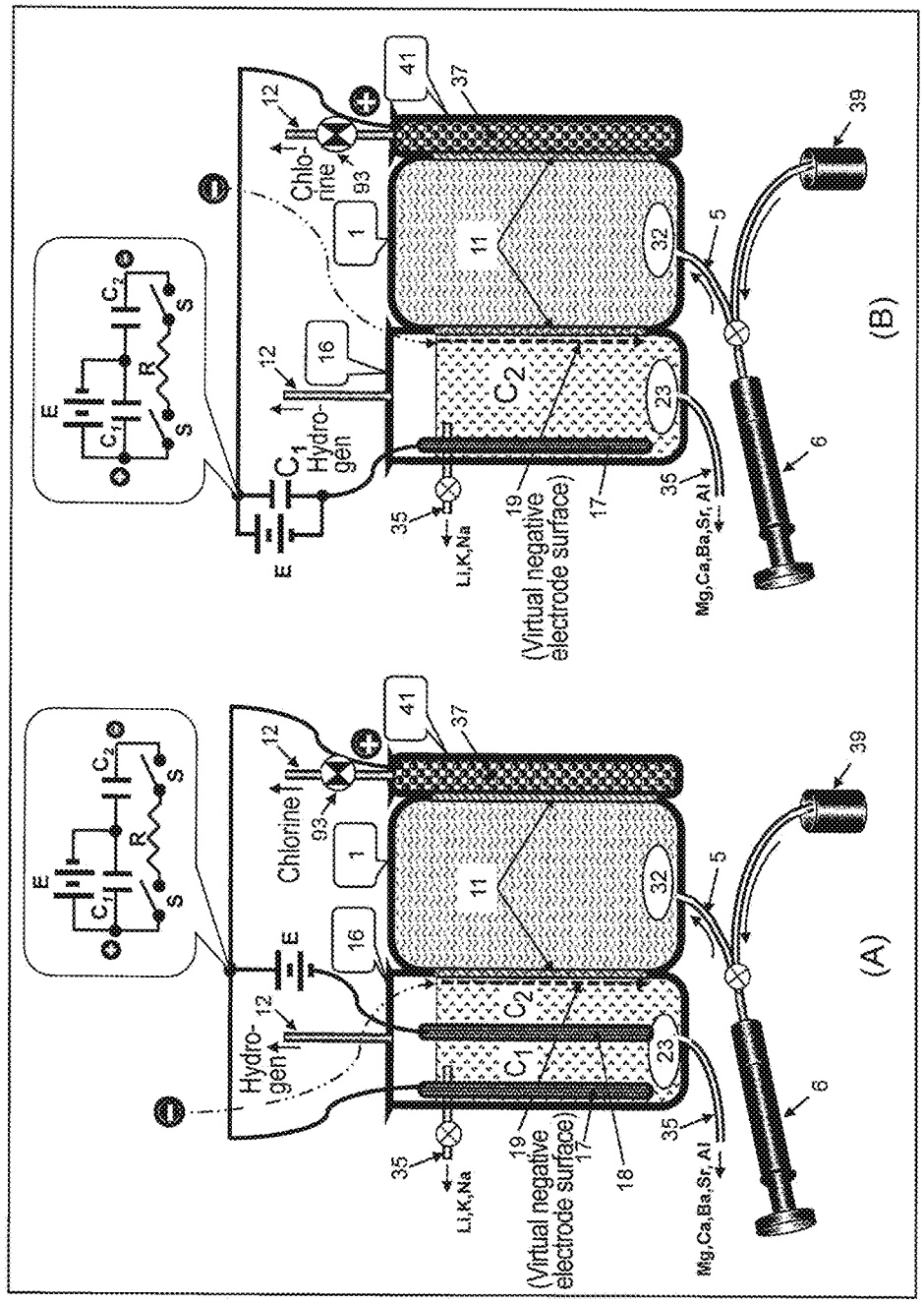
FIG. 14 is a diagram briefly showing an electrolytic refining device which uses the interface between an oil and an aqueous electrolyte solution as the virtual negative electrode, in which (A) shows an electrolytic refining device including an intermediate electrode plate inserted to an oil-filled electrode chamber, and (B) shows an electrolytic refining device including a solid capacitor outside the system of an oil-filled electrode chamber.
Figure 37:
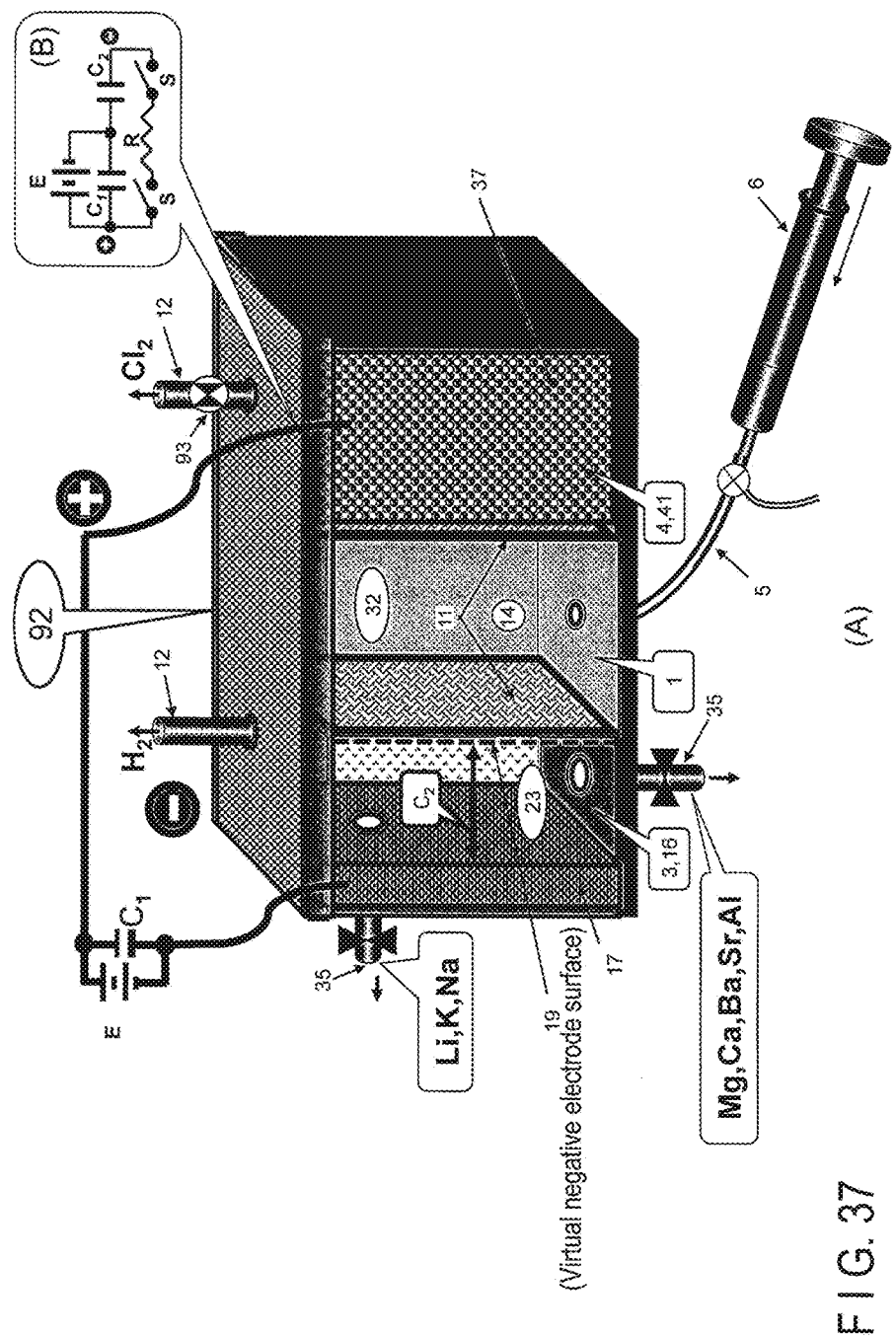
FIG. 37 is a diagram briefly showing a base metal-producing apparatus which utilizes a virtual negative electrode, in which (A) shows the device and (B) shows an equivalent circuit.

FIG. 37 is a diagram showing the structure of a base metal producing device which uses a virtual negative electrode from an aqueous base metal chloride solution. FIG. 14(B) shows a principle thereof, in which an interface between an oil surface and an aqueous base metal salt solution of element of Group 1 or 2 of the periodic table, is used as a virtual negative electrode surface, and the aqueous base metal salt solution is electrolyzed to collect negative electrode deposits in the oil layer. It is easy to consider that the interface of an oil and an aqueous electrolyte solution is used as a virtual electrode. However, unless this virtual electrode is a negative electrode, a negative electrode product will not be produced. Here, how to use a virtual electrode as a negative electrode will be described based on the base metal producing device which uses the equivalent circuit "Murahara circuit" of FIG. 37(B), and the virtual negative electrode of FIG. 37(A). That is, the switch (S) of the equivalent circuit of FIG. 37(B) corresponds to the water-repellent porous membrane 11 which sets on/off by means of the aqueous electrolyte solution 14 at the water-resistant pressure with the pressure-applying member 6, and the aqueous electrolyte solution 14 is denoted by (R). The oil 23 in the oil-filled electrode chamber 16 is denoted by (C2), the voltage is (E) and the large-capacity capacitor installed outside is (C1). If the pressure at the water-resistant pressure is applied after a voltage (E) is first applied to the large-capacity capacitor (C1), the switches (S) of both electrode chambers are turned on. The virtual electrode surface 19 functions as a negative electrode. With the charge stored in C1, through serial capacitors of C1 and C2, a potential is applied to R, and thus electrolysis is performed. Then, in the virtual negative pole electrode side 19, base metals whose specific gravities are lighter than that of the oil (namely, Li, K, Na) are collected from the upper portion, and those having specific gravities heavier than that of the oil 23 (namely, Mg, Ca, Ba, Sr, Al) are collected from the lowermost portion. At the same time, gaseous chlorine is collected by the product gas collecting hose 12 at the uppermost portion of the gas-permeable electrode chamber 41 of the positive electrode chamber 4. Thus, the base metal producing device uses a virtual negative electrode comprising the pressure regulating valve 93 in front of the product gas extraction port in order to maintain the pressure on the gaseous chlorine producing side at a certain level or below.

Figure 15:
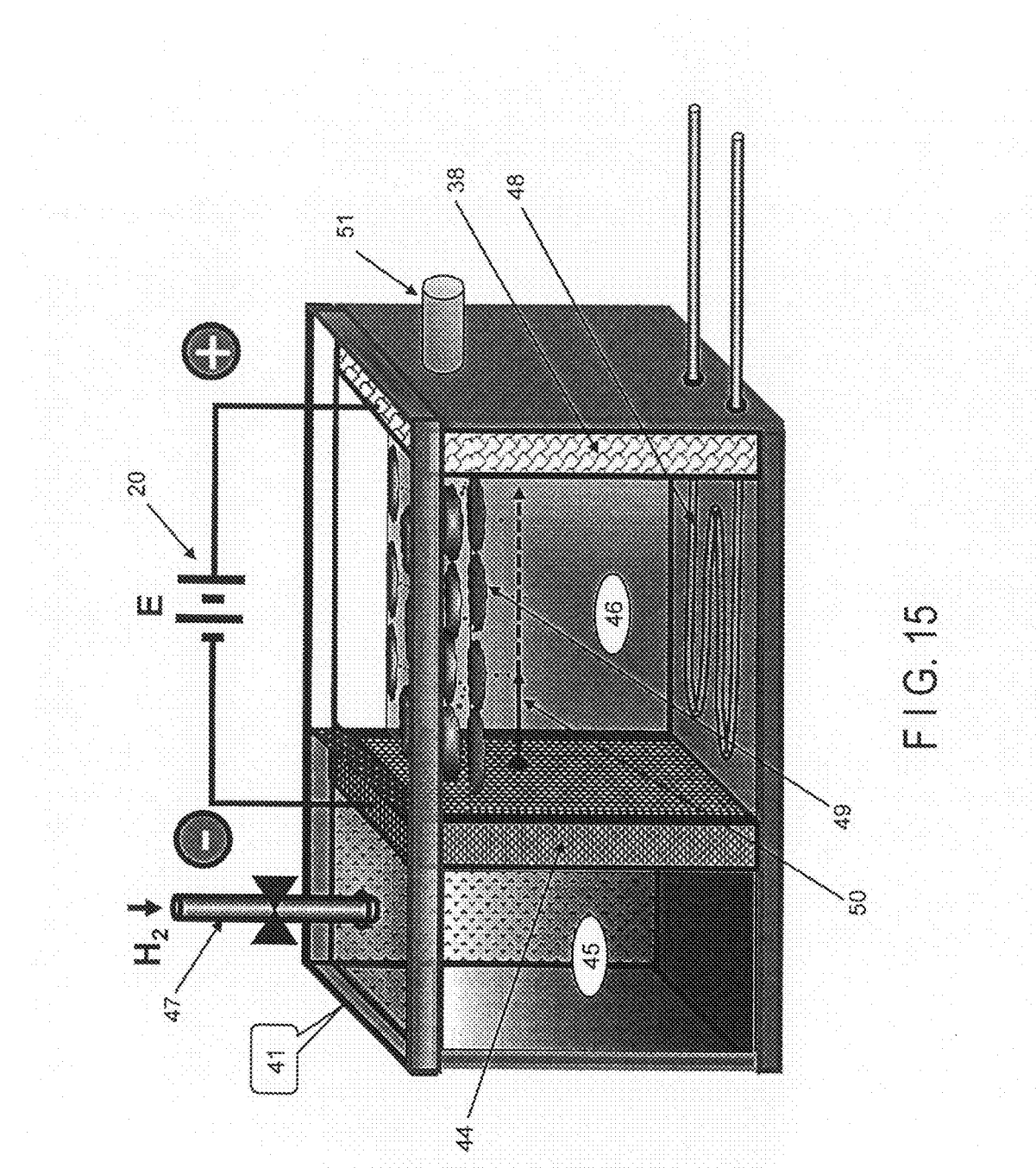
FIG. 15 is a diagram briefly showing a device of manufacturing a base metal hydride by an ionic reaction between hydrogen negative ion and molten salt.
Figure 17:
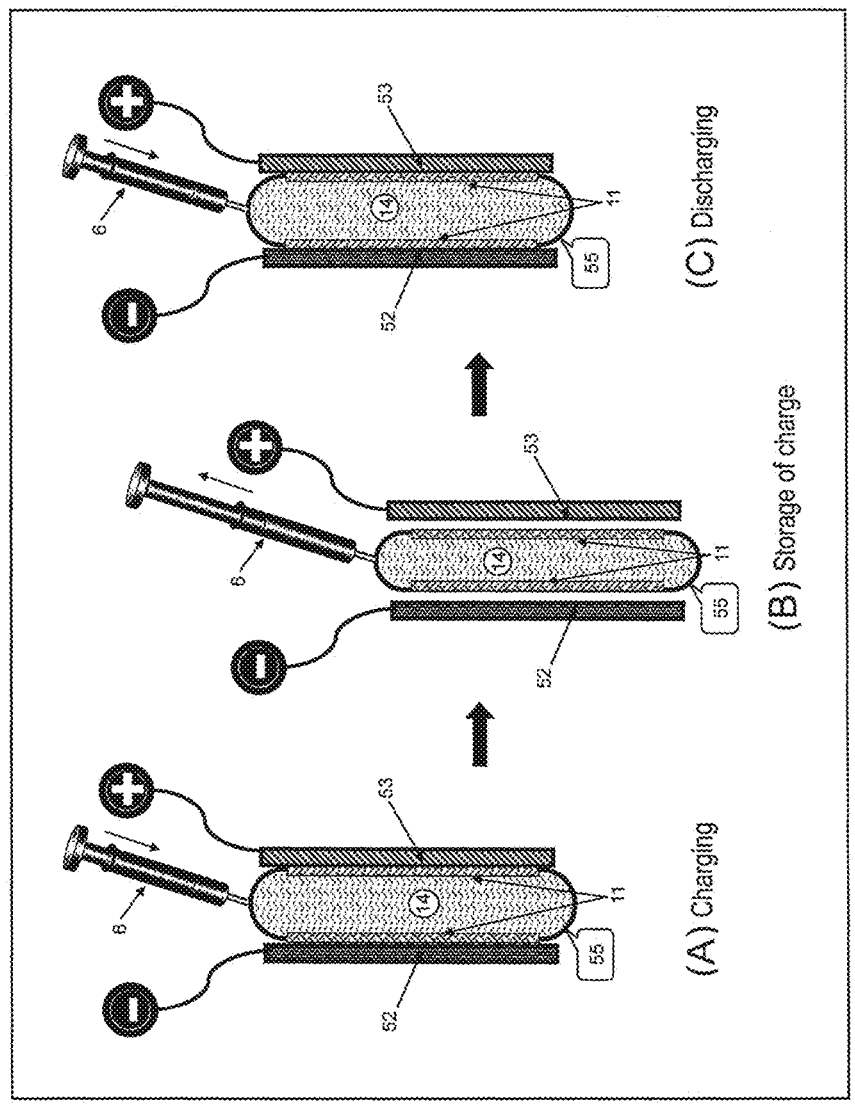
FIG. 17 is a diagram briefly showing a battery, (A) shows a battery when charging, (B) shows the battery when storing charge and (C) shows the battery when discharging.
Figure 38:
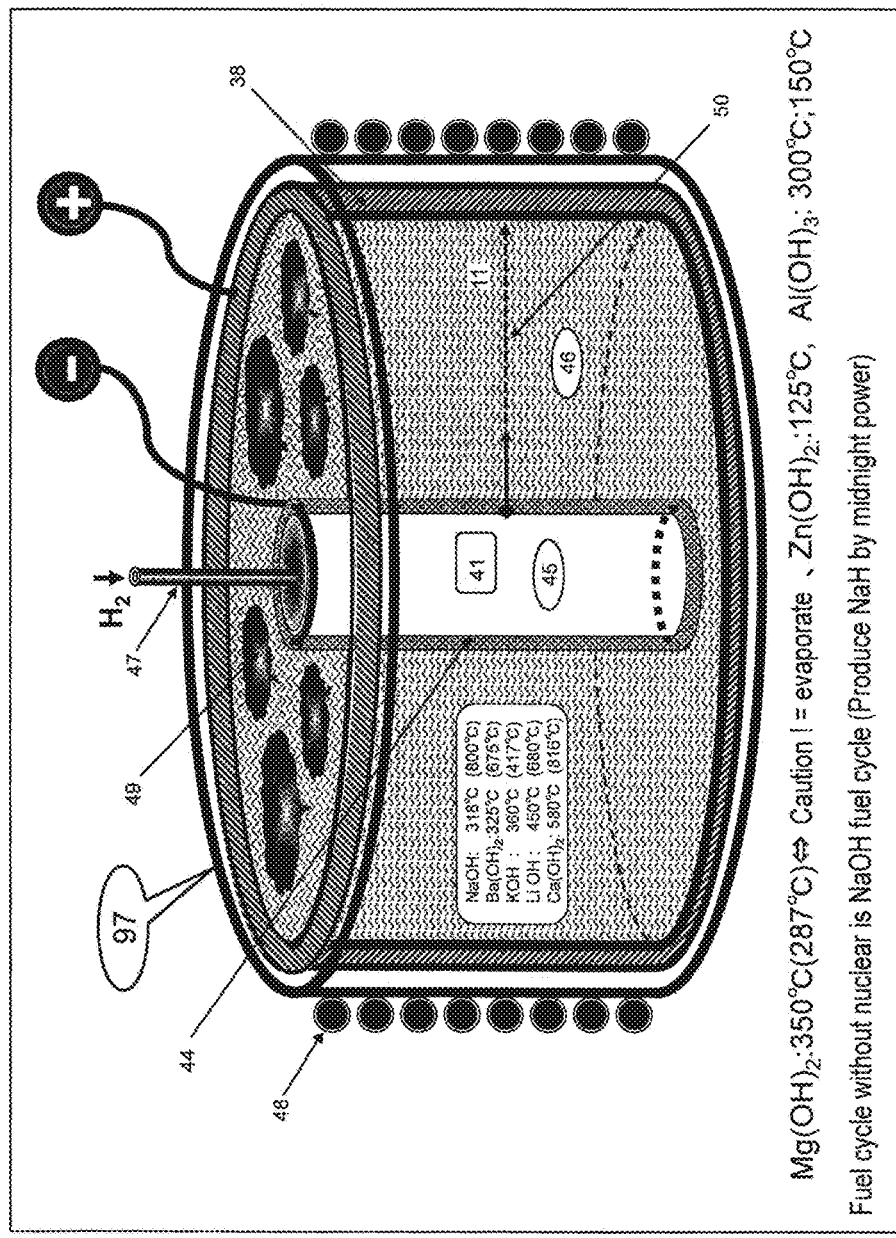
FIG. 38 is a diagram briefly showing a base metal hydride-producing apparatus.

FIG. 38 shows a base metal hydride-producing device. Generally, sodium hydride is produced by combining, with hydrogen at high temperature, metallic sodium produced by molten-salt electrolysis of caustic soda. The production cost of metallic sodium is high. As described in connection with FIG. 15, the melting point of caustic soda is remarkably low as 318° C. Therefore, when a container containing caustic soda is heated at 318° C. or higher, ionized molten salt is produced. As shown in FIG. 38 illustrating the metal hydride producing device 97, if cation ($H^+$) of hydrogen and anion ($H^-$) 50 of hydrogen are made to react in a caustic soda molten salt ($Na^++OH^-$), the following takes place: $Na^+ + OH^- + H^- + H^+ \rightarrow NaH + H_2O$. Then, in order to produce the anion (H—) 50 of hydrogen in the caustic soda molten salt 46, hydrogen gas is supplied with pressure to a porous carbon negative electrode/isolation film 44 having the structure of a gas-permeable electrode chamber 41 through an injection port 47. Further, the caustic soda molten salt 46 is inserted between the negative electrode 44 formed of the porous carbon negative electrode-cum-isolation film 44 and the positive electrode plate 38. Here, if a potential for producing hydrogen anion 50 is applied between both electrodes, it reacts with sodium ion (Na$^+$) in a caustic soda molten salt to produce sodium hydride (NaH) 49 only by an ionic reaction, not by a heat reaction. Further, the specific gravity of the sodium hydride (NaH) 49 is lighter than that of the caustic soda molten salt 46 and the melting point is significantly higher than that of the caustic soda 46; therefore the product floats as a solid matter for the device to be able to easily collect.

Figure 39:
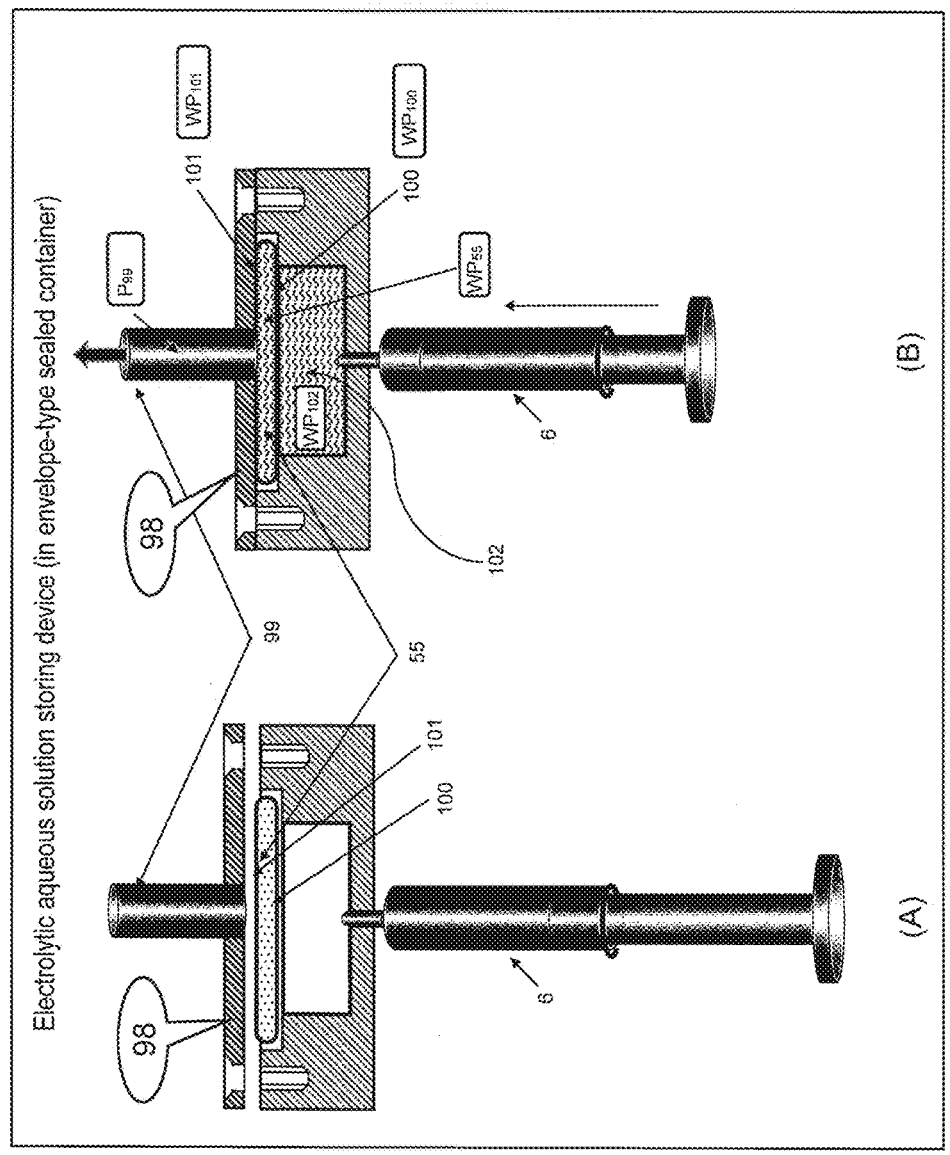
FIG. 39 is a diagram briefly showing an aqueous electrolyte solution reservoir to be inserted to an envelope-type sealed container, in which (A) shows the device before reserving the aqueous electrolyte solution and (B) shows the device after reserving the aqueous electrolyte solution.

FIG. 39 shows a device for reserving an aqueous electrolyte solution into an envelope-type sealed container. An envelope-type sealed container 55 is manufactured by stacking two sheets of water-repellent porous material 11 and heat-welding them by four sides around 350° C. The envelope-type sealed container 55 has a variety of usage as an aqueous electrolyte solution storage container of a battery. Here, an aqueous electrolyte solution reservoir detention device 98 reserves an aqueous electrolyte solution 14 or 102 in the envelope-type sealed container 55. As shown in FIGS. 39(A) and (B), both surfaces of the envelope-type sealed container 55 comprise a water-repellent porous fluororesin film 100 and a water-repellent porous fluororesin film 101, respectively. The water-resistant pressure of each of the water-repellent porous fluororesin films 100 and 101 varies with the salt concentration of the aqueous electrolyte solution as shown in FIG. 28. Here, as shown in FIG. 39(B), if the hydraulic pressure of the aqueous electrolyte solution for reservation 102 pressurized with the pressure-applying member 6 is denoted by (WP102), the hydraulic pressure of the aqueous electrolyte solution in the envelope-type sealed container 55 is denoted by (WP55), the water-resistant pressure of the water-repellent porous fluororesin film 100 on the side of the aqueous electrolyte solution 102 is denoted by (WP100), the water-resistant pressure of the water-repellent porous fluororesin film 101 on the side of the suction port 99 is denoted by (WP101), and the air pressure of the suction portion 99 is denoted by (P99), the condition to seal the aqueous electrolyte solution 102 inside the envelope-type sealed container 55 by making it to pass the pores of the water-repellent porous fluororesin film 100 is WP102≥WP55+WP100, whereas the negative pressure condition for suctioning at the suction port 99 for reserving the aqueous electrolyte solution in the envelope-type sealed container 55 is WP101≥P99≥−WP101. Here, if the water-repellent porous fluororesin films 100 and 101 used for the two surfaces are made of the same material, it is expressed as WP100=WP101. Thus, the aqueous electrolyte solution reservoir device 98 shown in FIG. 39(B), first starts the pressurization of the aqueous electrolyte solution 102 with the pressure-applying member 6 while maintaining a negative pressure not less than the water-resistant pressure (−WP101) of the water-repellent porous fluororesin film 101 on the suction port 99 side, and simultaneously changes the pressure at the suction port 99 to (+WP101), to seal the aqueous electrolyte solution 102 in the envelope-type sealed container 55.

Figure 40:
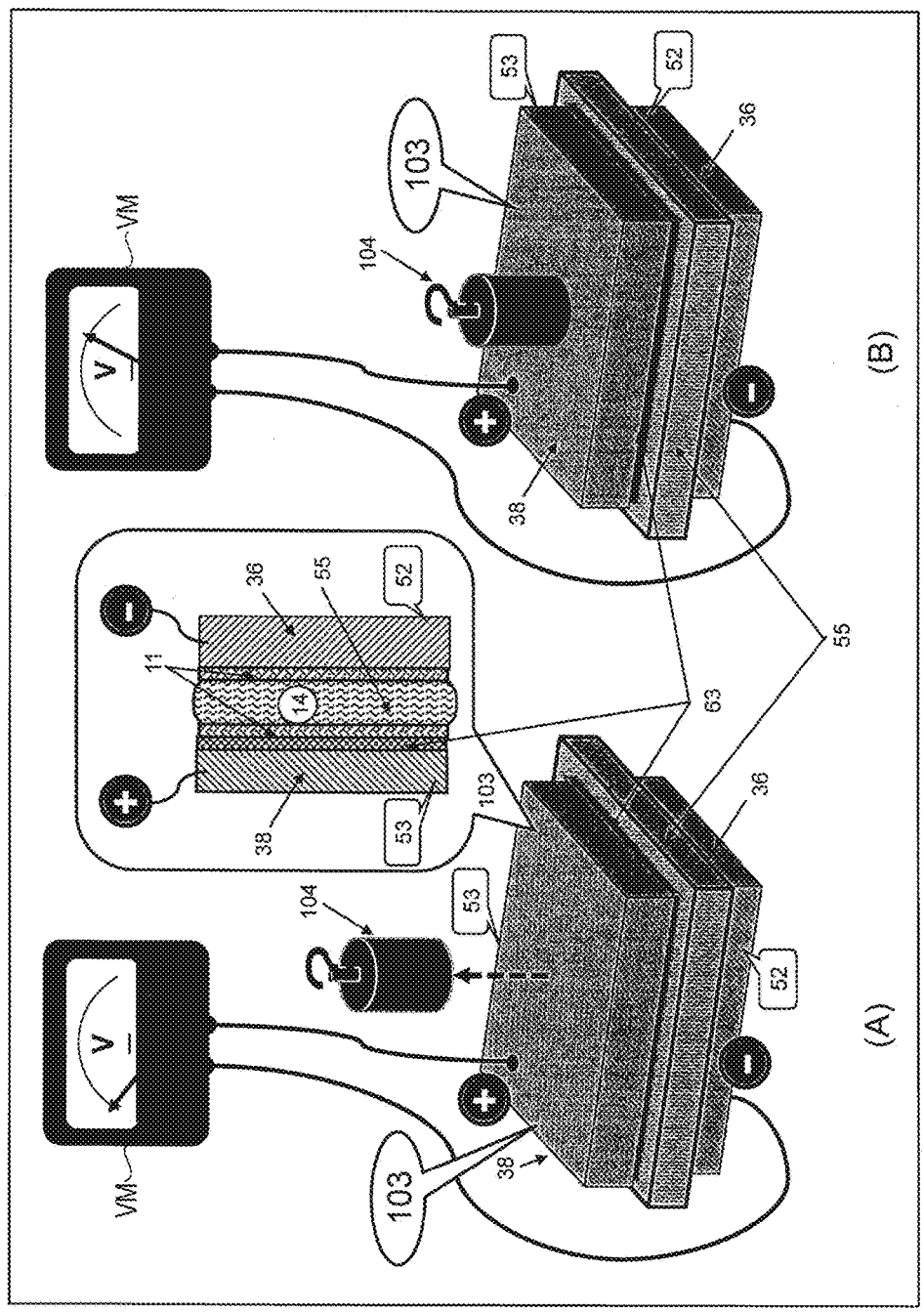
FIG. 40 is a diagram briefly showing an electrolyte-pressurization type secondary battery, in which (A) shows the case where the aqueous electrolyte solution is not pressurized and (B) shows the case where the aqueous electrolyte solution is pressurized.

FIG. 40 shows an aqueous electrolyte solution pressurization type secondary battery. FIG. 40(A) shows the structure of an electrolyte pressurization type secondary battery 103, in which an aqueous electrolyte solution 14 is sealed hermetically in an envelope-type sealed container 55 which uses a water-repellent porous fluororesin film 11 for an isolation film with respect to an electrode, which is further interposed between a negative electrode chamber 52 and a positive electrode chamber 53. Here, when a weight 104 is placed to weight the device, a potential (V) will appear as shown in FIGS. 40(A) and (B). If the weight 104 is removed, the potential (V) will be 0V. In this embodiment, an aluminum plate was used for the negative electrode plate 36 of the negative electrode chamber 52, and a metal chloride film 63 such as of AlCl$_3$, ZnCl$_2$, MgCl$_2$ or the like was used for the positive electrode plate 38 of the positive electrode chamber 53. First, as a preliminary test of a primary battery, both surfaces of the envelope-type sealed container enclosing a 10%-concentration aqueous sodium chloride solution are interposed between a negative electrode made from a magnesium plate and a positive electrode made from a zinc plate in which a chloride film is formed on an electrode surface, and if the water-repellent porous fluororesin film 11 with a diameter of pores of 33 μm is pressurized with the weight 104 equivalent to the water-resistant pressure 330 mmHg, shown in FIG. 28, an electromotive force of 3.5V is obtained. When the weight 104 is removed, a voltage value shows 0V. Next, as a preliminary test of a secondary battery, an envelope-type sealed container 55 enclosing a 25%-concentration aqueous aluminum chloride solution was prepared, and both surfaces thereof were interposed between aluminum electrode plates. Here, while weighting with the weight 104 equivalent to the water-resistant pressure of the water-repellent porous fluororesin film 11, the battery was charged at DC 10A for 60 minutes. Then, the weight 104 was removed to finish the charging. The concentration of the aqueous aluminum chloride solution in the envelope-type sealed container 55 was 23%, and theoretically chargeable up to 10%. Here, the battery was let stand with the weight 104 removed for one month, and then when the electrolyte pressurization type secondary battery 103 was again pressurized from the top with the weight 104, an electromotive force of 3.5V was indicated. When the weight 104 was removed, the voltage value showed 0V. If the pressurization and release by the weight 104 were repeated, but there was no change in the concentration of the aqueous aluminum chloride solution enclosed inside the envelope-type sealed container 55. Thus, it has been proved that self-discharge does not occur inside.

Figure 21:
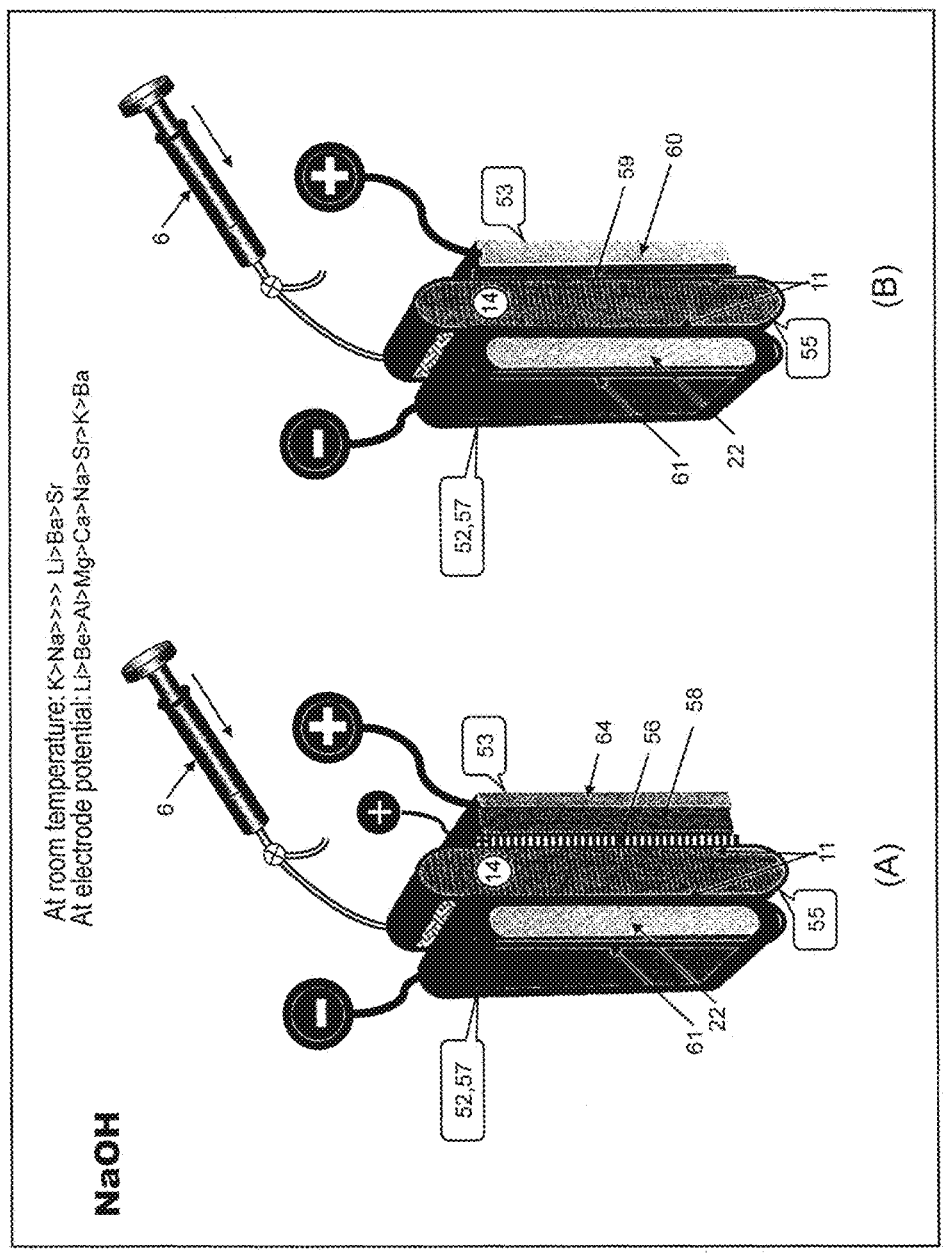
FIG. 21 is a diagram briefly showing a base metal/air battery, in which (A) shows a battery including an auxiliary electrode for charging, and a positive electrode made from a porous carbon plate, and (B) shows a battery which uses a metal oxide as the positive electrode.
Figure 22:
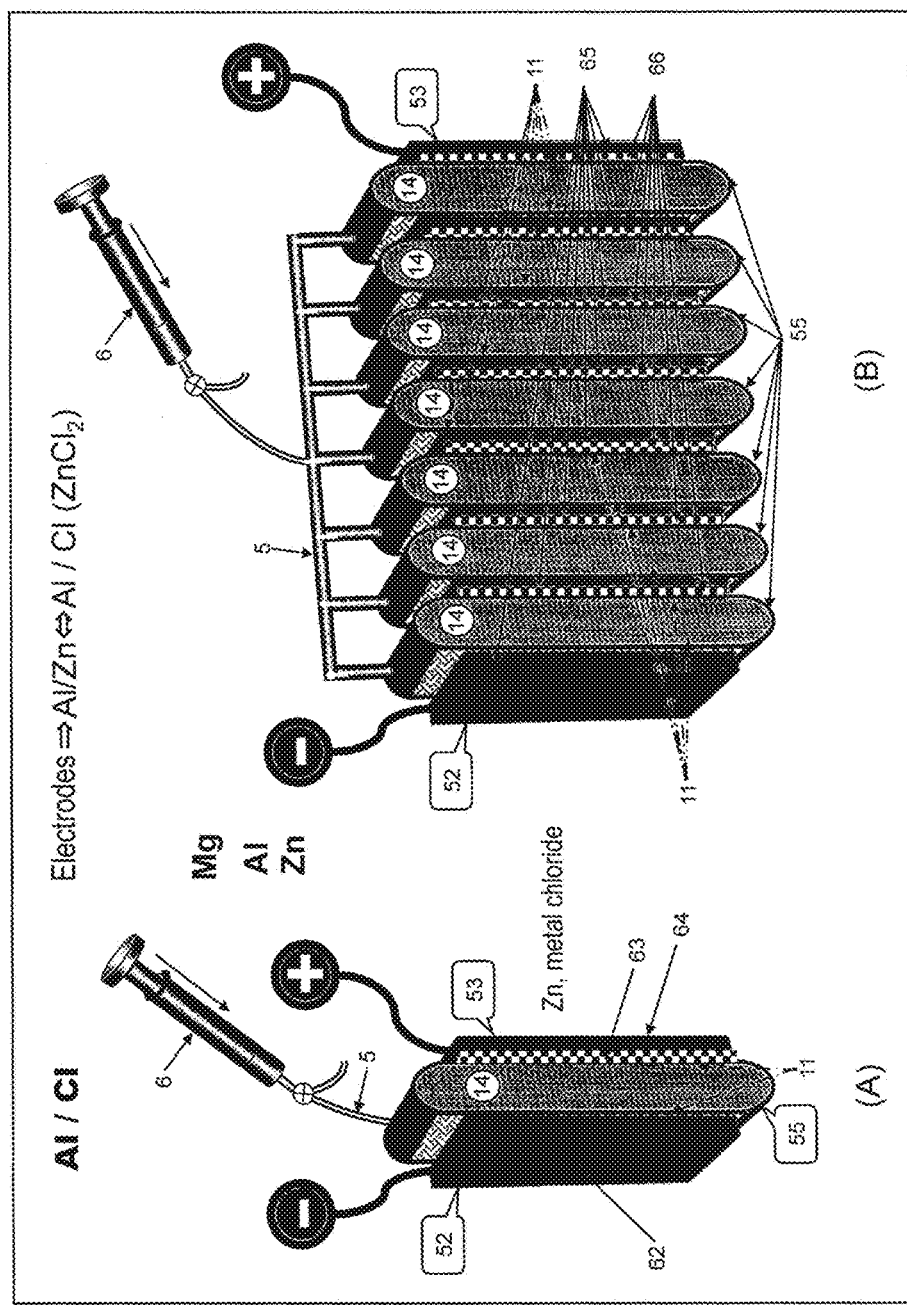
FIG. 22 is a diagram briefly showing a base metal/chlorine battery, in which (A) shows a single-layer battery and (B) shows a multilayer battery.
Figure 23:
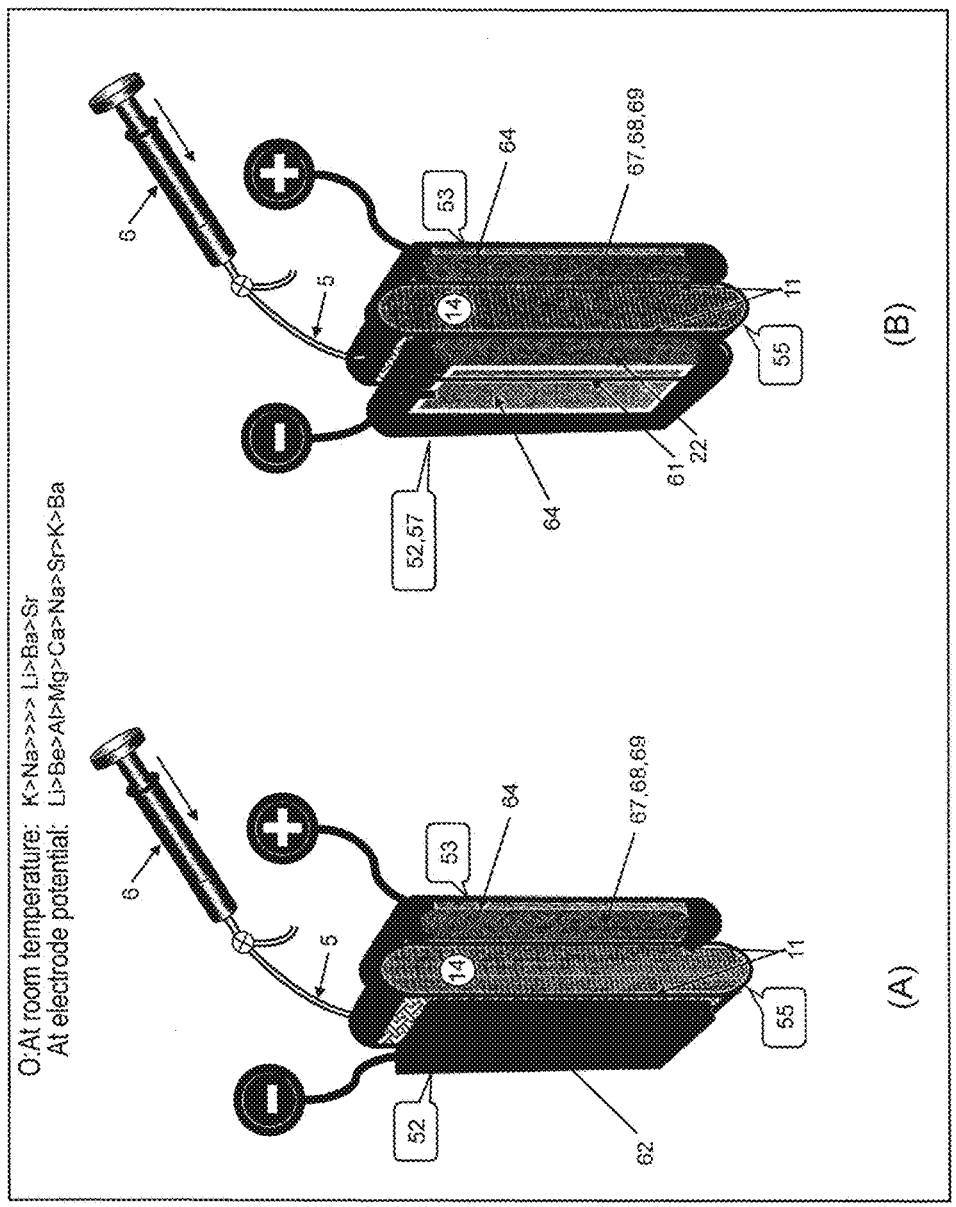
FIG. 23 is a diagram briefly showing base metal/bromine and base metal/iodine batteries, in which (A) shows the battery of the case where the negative electrode is of a metal which is not affected by the atmosphere, and (B) is a conceptual diagram of the battery of the case where the negative electrode is of a metal of Group 1 or 2 of the periodic table, which is weak to the atmosphere.
Figure 24:
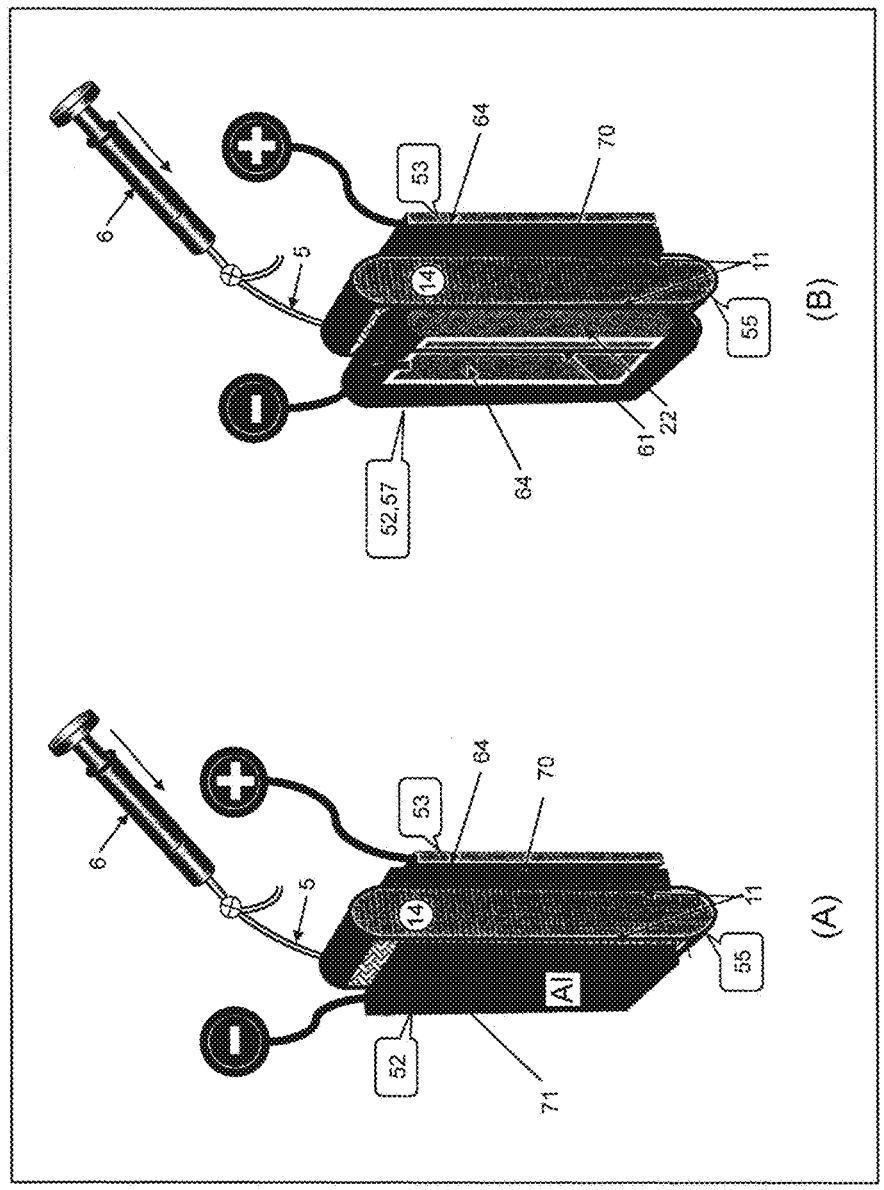
FIG. 24 is a diagram briefly showing a base metal/fluorine battery, in which (A) shows an Al/F battery and (B) shows a K/F or Na/F battery.
Figure 25:
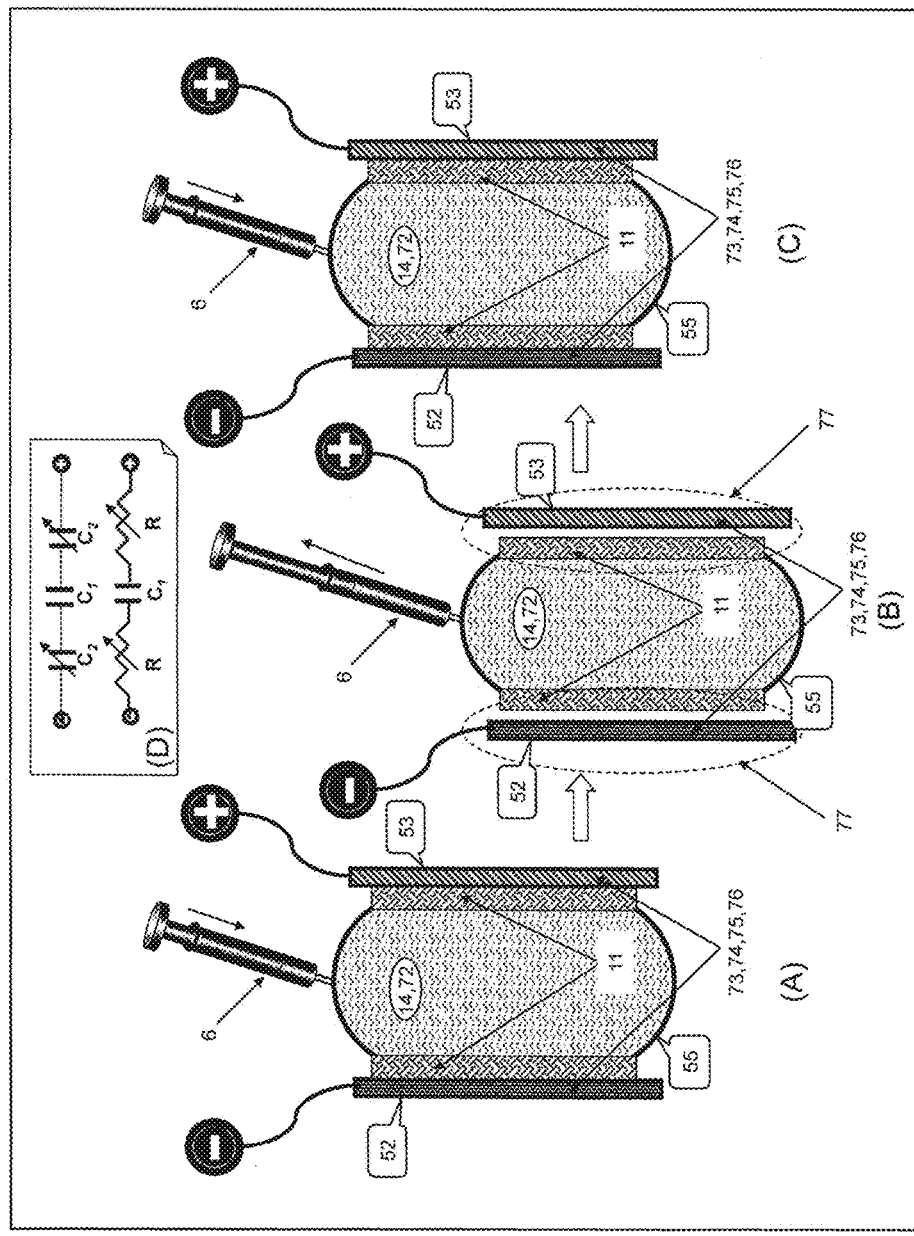
FIG. 25 is a diagram briefly showing a capacitor, in which (A) shows the capacitor when charging, (B) shows the capacitor when storing charge, (C) shows the capacitor when discharging, and (D) is an explanatory diagram of operation of a circuit while charging, storing charge and discharging.
Figure 26:
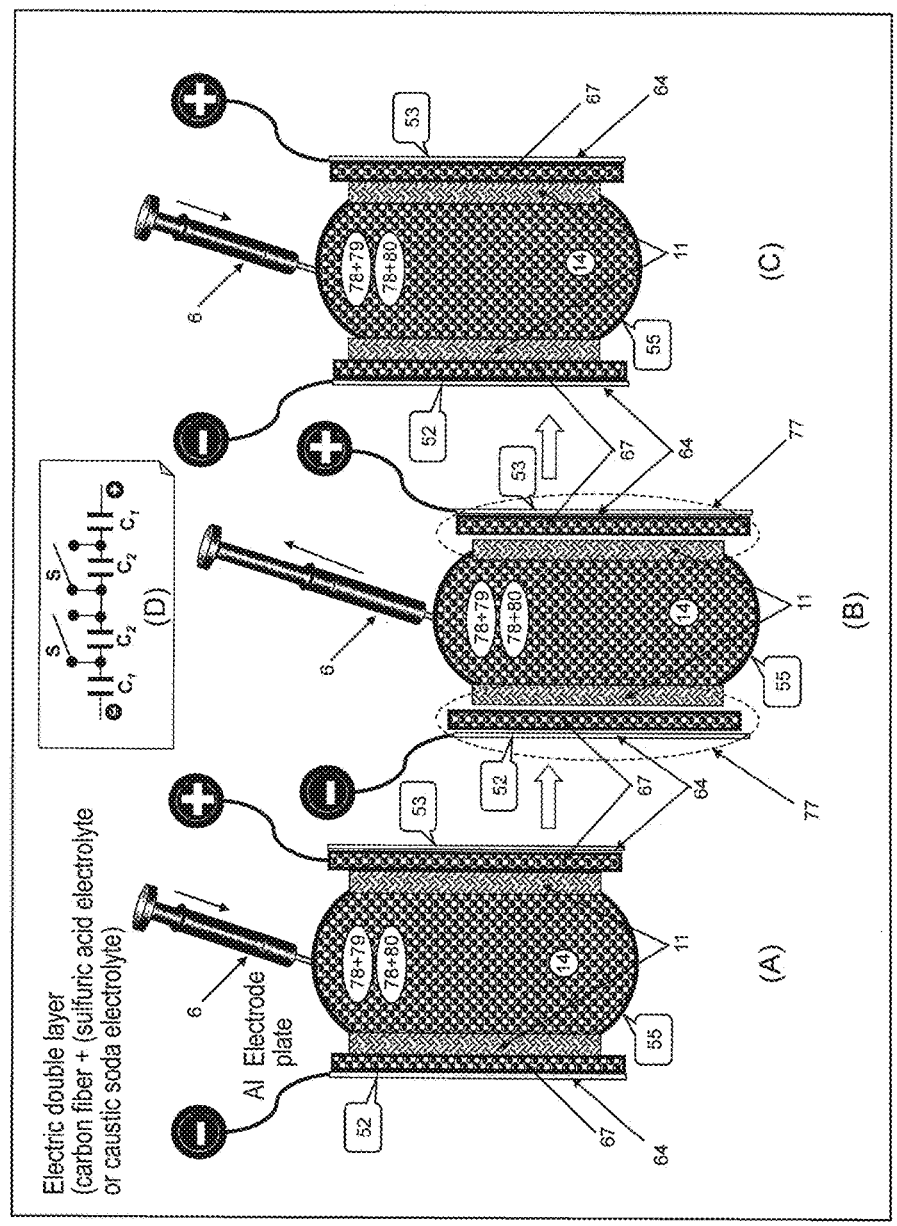
FIG. 26 is a diagram briefly showing an electric double-layer capacitor, in which (A) shows the capacitor when charging, (B) shows the capacitor when storing charge, (C) shows the capacitor when discharging, and (D) is an explanatory diagram of operation of a circuit while charging, storing charge and discharging.
Figure 41:
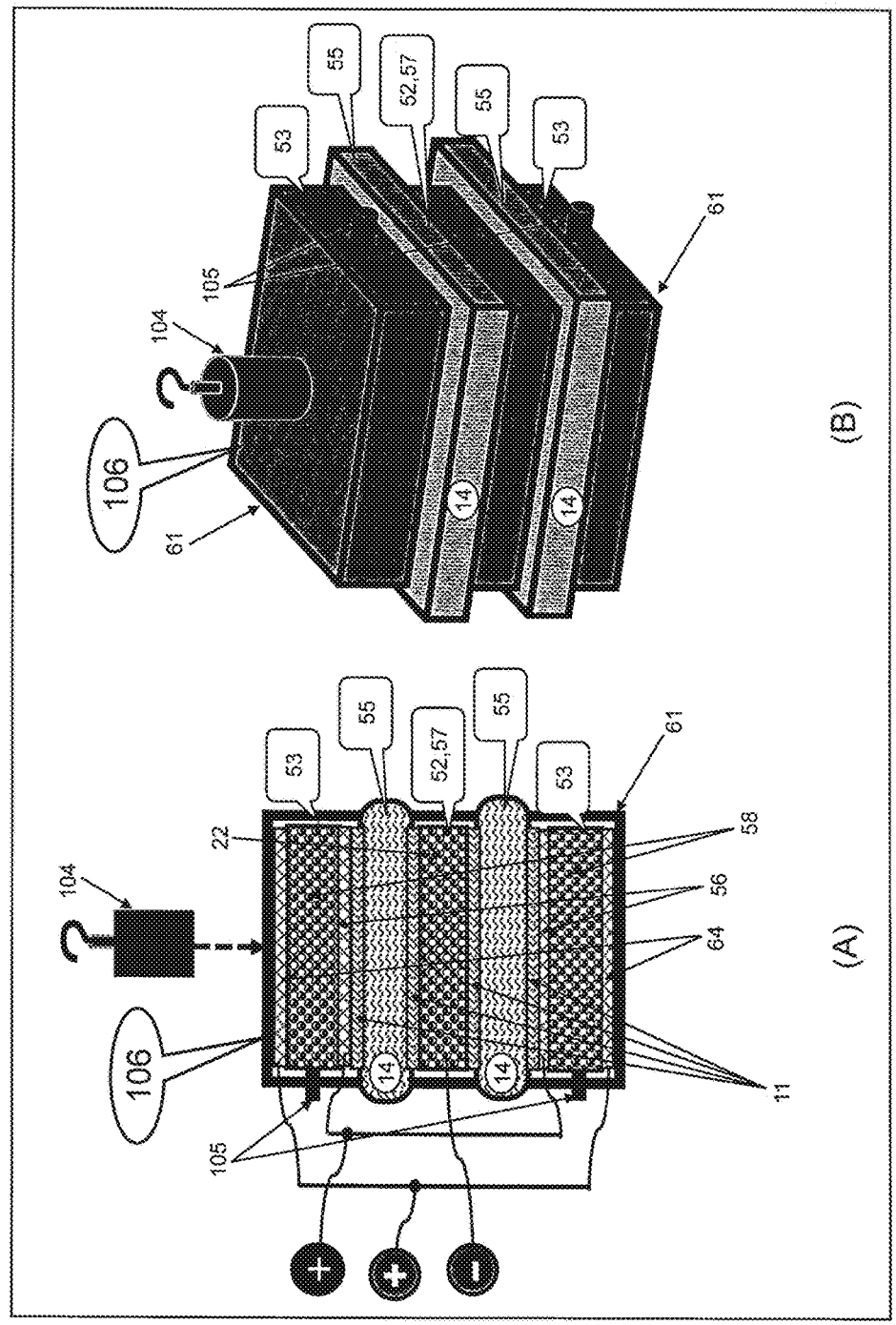
FIG. 41 is a diagram briefly showing a multilayered type caustic soda secondary battery, in which (A) is a sectional view and (B) is an outer perspective view.

FIG. 41 shows a stacked-layer type caustic soda secondary battery. As shown in FIG. 21, an aqueous caustic soda solution is used for the electrolyte, air is used for a positive electrode, carbon fiber is used for a negative electrode, and sodium is deposited in pores of carbon when charging. FIG. 41(A) shows a cross section of the stacked-layer type caustic soda secondary battery 106, in which an envelope-type sealed container 55 is interposed between a negative electrode chamber 52 and a positive electrode chamber 53. The envelope-type sealed container 55 is a bag whose both surfaces are made of a water-repellent porous fluororesin 11. An aqueous electrolyte solution 14 enclosed inside is 1 to 8-N caustic soda and negative electrode chambers 52 and 57 are those having such a structure that Na-electrode plates or carbon-made porous electrode plates in which Na is adsorbed inside or in pores of the surface thereof, and the negative electrodes are enclosed with a resin film 61 or an oil 22 is absorbed inside the negative electrodes. On the other hand, in an oxygen electrode of a positive electrode chamber 53, air is adsorbed to a carbon-made porous electrode plate (activated carbon) 58, and an auxiliary positive electrode 56 for charging (mesh electrode) is provided between the water-repellent porous membrane 11 and the carbon-made porous plate to avoid heat generation from the carbon-made porous electrode plate (activated carbon) 58. For power, a collector electrode plate 64 is provided at the back surface of the carbon-made porous electrode plate (activated carbon) 58. FIG. 41(B) is a view briefly showing the secondary battery, in which a stacked-layer caustic soda secondary battery 106 is enclosed with the resin film 61 to be isolated from the external environment, and is charged while the aqueous electrolyte solution 14 in the envelope-type sealed container 55 is pressurized with the weight 104. At the time when the charging is completed, the pressurization of the aqueous electrolyte solution 14 is released to maintain the storage of charge state, and when discharging, the aqueous electrolyte solution 14 is pressurized to start discharging. As shown in FIG. 18, the solubility of aqueous caustic soda solution to water is high, and it is 50% at room temperature. First, a 50% aqueous caustic soda solution is sealed inside the envelope-type sealed container 55 of the water-repellent porous fluororesin film 11, and the negative electrode chambers 52 and 57 are enclosed with the resin film 61. The negative electrode chamber 57 is made of a carbon-made porous electrode impregnated with the oil of an outside air isolation type, whereas the positive electrode is the carbon-made porous electrode plate 58 of activated carbon provided with an air inlet 105 through which air enters and exits, which is enclosed with the resin film 61. The positive electrode chamber 53 comprises the mesh auxiliary positive electrode 56 for charging between the water-repellent porous membrane 11 and the carbon-made porous electrode plate 58 of activated carbon.

The outside air isolation type negative electrode chamber 57 and the positive electrode chamber 53 are inserted in the envelope-type sealed container 55 made of the water-repellent porous fluororesin film 11. Here, as a preliminary test, first, the caustic soda battery 106 is pressurized from the upper part with the weight 104 equivalent to the water-resistant pressure of the water-repellent porous fluororesin film 11, and is charged at 10A for 60 minutes in this state between the auxiliary positive electrode 56 for charging and the carbon-made porous electrode plate in the outside air isolation type negative electrode chamber 57. After that, the weight 104 was removed and charge was finished. At this point, the concentration of the aqueous caustic soda solution inside the envelope-type sealed container 55 was 43%, which is theoretically chargeable up to 10%. Here, when electric load was applied between the carbon-made porous electrode plate in the outside air isolation type negative electrode chamber 57 and the collector electrode plates 64 made from a copper plate, and also weighted with the weight 104 again, discharging started and its electromotive force was 3V. When the battery was let stand with the weight 104 removed for one month, and then again pressurized with the weight 104, it exhibited an electromotive force of 3V. When the weight 104 was removed, the voltage value indicated 0V. If the pressurization and release by the weight 104 were repeated, but there was no change in the concentration of the aqueous caustic soda solution enclosed inside the envelope-type sealed container 55. Thus, it has been proved that self-discharge does not occur inside.

Figure 27:
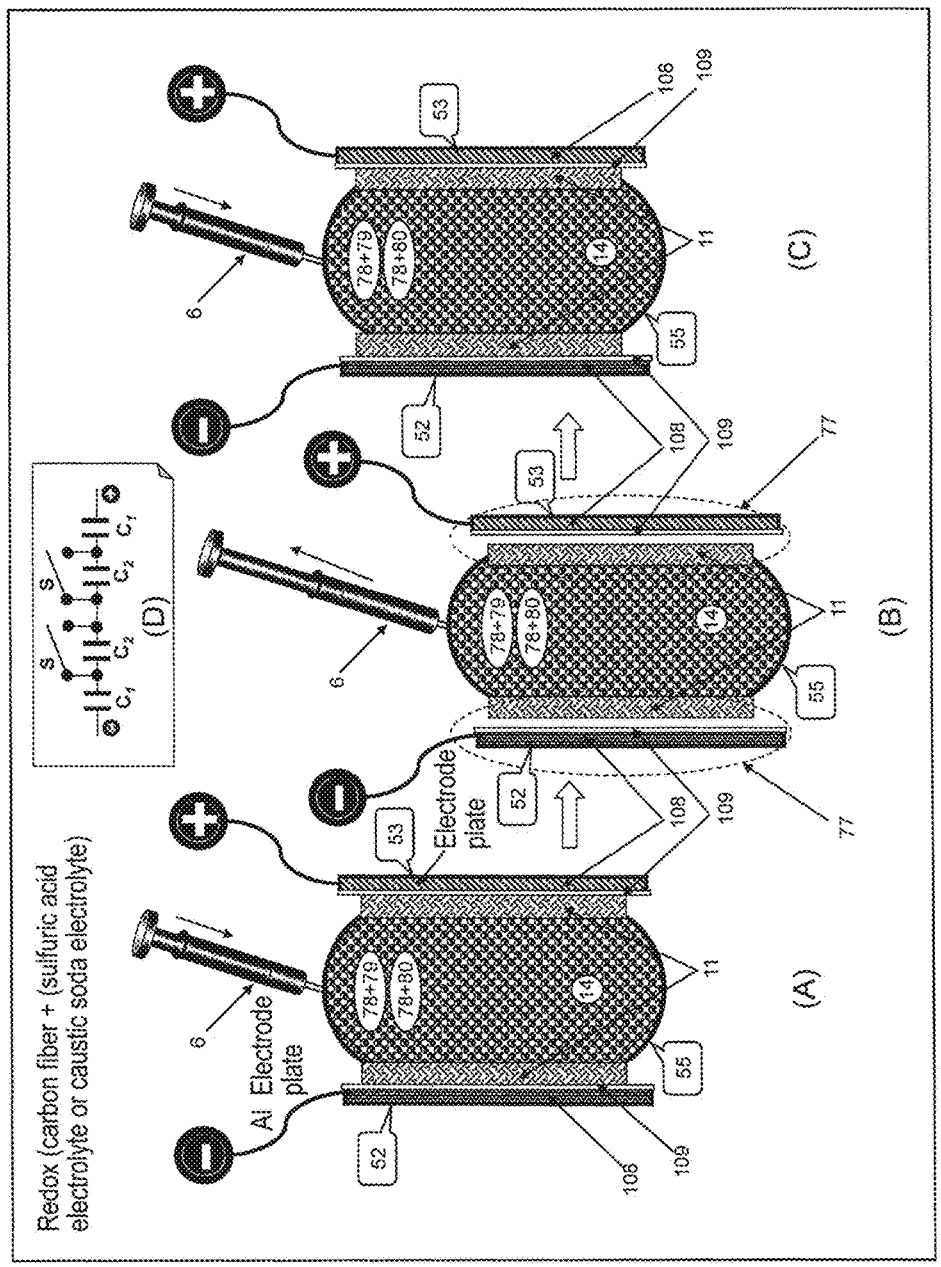
FIG. 27 is a diagram briefly showing a redox capacitor, in which (A) shows the capacitor when charging, (B) shows the capacitor when storing charge, (C) shows the capacitor when discharging, and (D) is an explanatory diagram of operation of a circuit while charging, storing charge and discharging.
Figure 42:
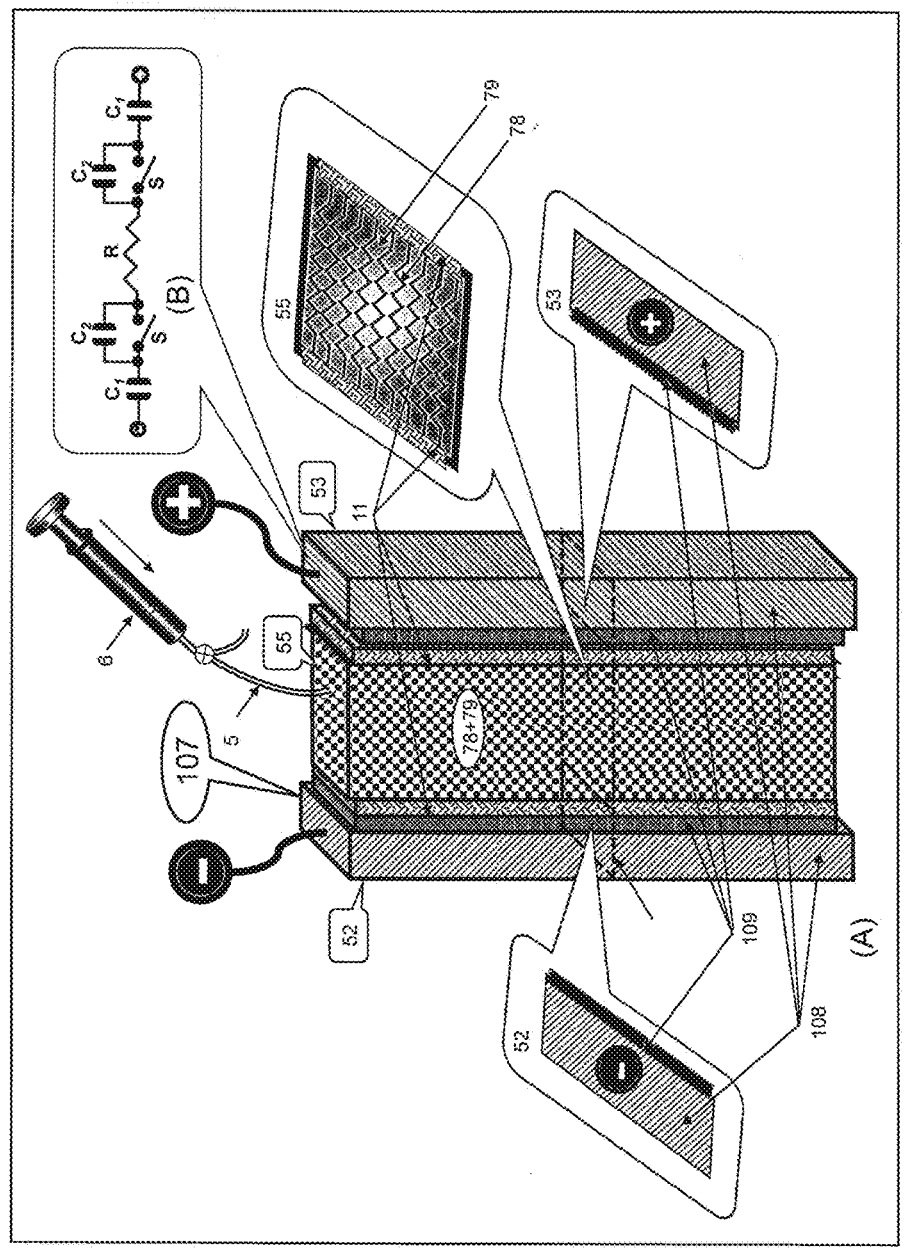
FIG. 42 is a diagram briefly showing a redox capacitor, (A) shows a sectional view and (B) shows an equivalent circuit.

FIG. 42 shows the structure of a redox capacitor. FIG. 27 shows the operation principle thereof, in which ferroelectric capacitors in which a very thin oxide film is formed on a surface of a metal plate are arranged on both positive and negative electrodes, and the positive electrode and the negative electrode are structurally the same. The redox capacitor 107 can be described in terms of electrical circuit as follows. An equivalent circuit C1 shown in FIG. 42(B) is a negative electrode chamber 52, and as shown in FIG. 42(A) in its cross section, a very thin oxide film 109 for redox capacitor is formed on a surface of a metal plate 108 for redox capacitor to prepare a ferroelectric capacitor. Note that a positive electrode chamber 53 and a negative electrode chamber 52 are also the same in material and structure. The envelope-type sealed container 55 is interposed between a pair of the positive and negative electrode chambers 52 and 53 via the water-repellent porous membrane 11. The equivalent circuits of the water-repellent porous membrane 11 are a low-dielectric constant capacitor ($C_2$) and switch (S) shown in 42(B). Especially, in the present invention, the inside of the envelope-type sealed container 55 is filled with a porous conducting material 78 of carbon fiber, a metal fiber or the like, and the pores are impregnated with the aqueous electrolyte solution (dilute sulfuric acid) 79 for electrochemical capacitors. Here, if a hydraulic pressure equal to the water-resistant pressure is applied with a pressure-applying member 6 and the diluted sulfuric acid 79 enters the pores of the water-repellent porous membrane 11 to turn on the switch (S) in the electrical circuit. The positive electrode chamber and negative electrode chamber are short-circuited with the porous conductive material 78 made of carbon fiber, metal fiber or the like, in the envelope-type sealed container 55. Thus, the two high-dielectric constant capacitors ($C_1$) are charged and discharged in series. On the other hand, the pressurization on the aqueous electrolyte solution 14 is released, the two low-dielectric constant capacitors ($C_2$) and the two high-dielectric constant capacitors ($C_1$) are connected in series to store the charge. When the aqueous electrolyte solution 14 is not pressurized, the aqueous electrolyte solution 14 does not enter the pores of the water-repellent porous membrane 11, and therefore it functions as a low-dielectric constant capacitor ($C_2$). If the aqueous electrolyte solution 14 is pressurized, the aqueous electrolyte solution enters the pores of the water-repellent porous membrane 11 to turn on the switch (S) in terms of electrical circuit. Thus, the positive electrode chamber and the negative electrode chamber are short-circuited via the sealed container (envelope-type) 55 made of a water-repellent porous membrane. Thus, the two high-dielectric constant capacitors ($C_1$) are charged and discharged in series. When the pressurization of the aqueous electrolyte solution 14 is released, the two low-dielectric constant capacitors ($C_2$) and the two high-dielectric constant capacitors ($C_1$) are connected in series to store the charge. The redox capacitor device uses aluminum (Al) for the metal plate 108 for redox capacitor and aluminum oxide ($Al_2O_3$) for the metal oxide film 109 for redox capacitor.

Figure 43:
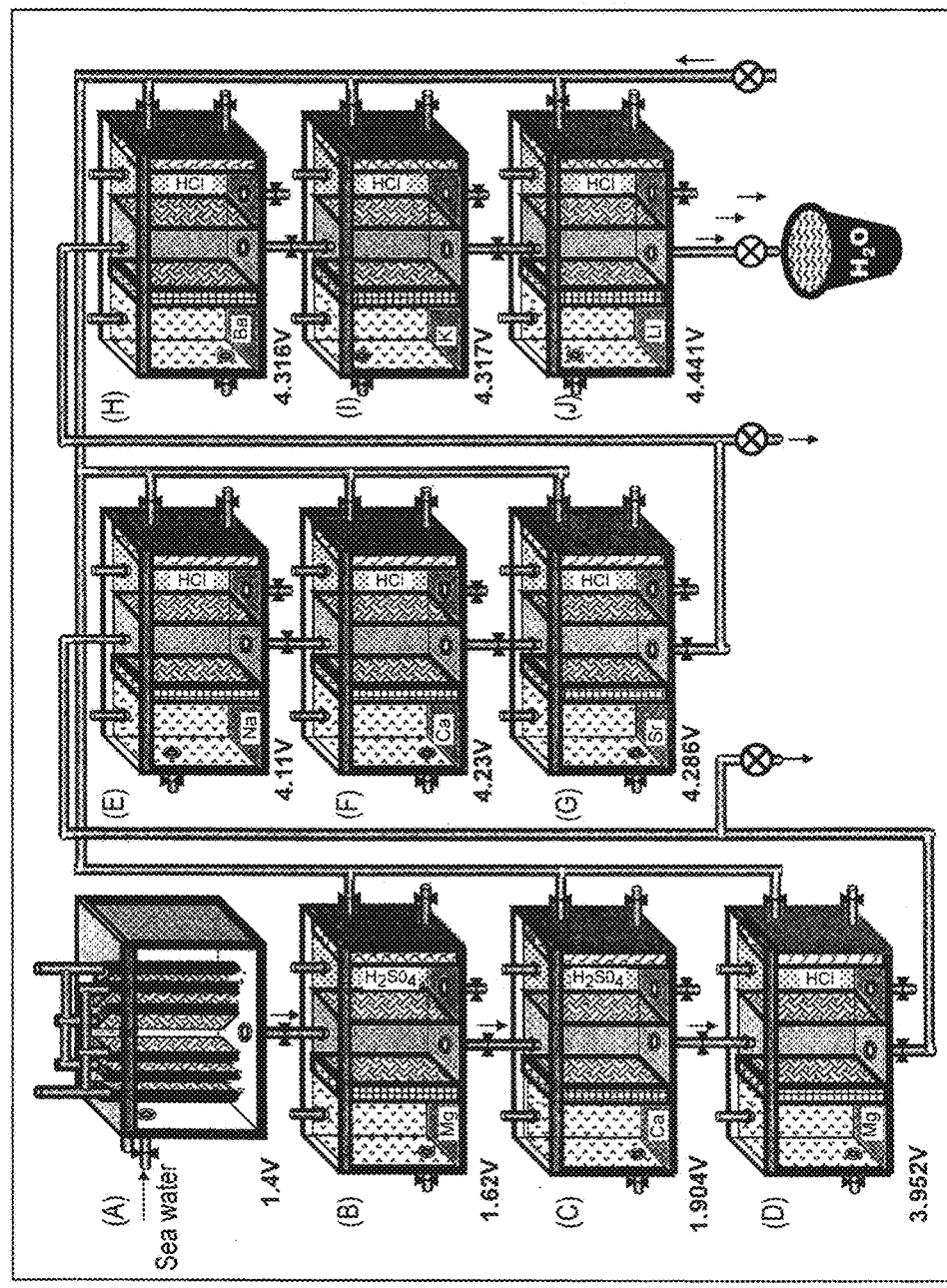
FIG. 43 is a diagram briefly showing a device which extracts base metals from a mixture aqueous solution of base metal salts.

FIG. 43 shows a method of selecting and collecting base metal elements, such as Na, K and Li of Group 1 and Mg, Ca, Sr and Ba of Group 2 from aqueous mixed salt solutions, such as sea water, salt lake water, hot spring water and industrial waste water. Note that the collecting efficiency is higher as the salt concentration is higher. For this reason, the first operation to be performed is that the waste fluid (concentrated salt water) should be subjected to electrolysis after dehydrating by heat or the reverse osmotic membrane method or after producing hydrogen by electrolysis of sea water. However, as shown in FIG. 19, as to the base metal chlorides, the solubility differs greatly from one metal element to another, and the solubility tends to go up as the solution temperature rises. For example, at 80° C., the solubility values of $ZnCl_2$, $CaCl_2$, LiCl, KCl and NaCl are 84.4%, 60%, 53%, 34% and 28%, respectively. It is desirable that the element subjected to be deposited have a higher solubility; however, it is necessary in practice to start with an element with a low solute decomposition voltage. Then, for those having 1.4V or higher, which is electrolytic voltage of water, the voltage applied is increased in the order of $MgSO_4$: 1.62V, $CaSO_4$: 1.904V, $MgCl_2$: 3.952V, NaCl: 4.11V and $CaCl_2$: 4.23V, and the waste fluid after each respective element deposited, is transported to the next deposit device. According to this method, each single element is selected and collected from multiple base metal element salts.

FIG. 44 is a schematic diagram of a caustic soda fuel cycle. According to the present invention, this fuel cycle is carried out on the sea. As to energy and materials, the sea is a rich repository of resources. As the inventor of the present invention states in Non-patent Literatures 3 and 4, 70.8% of the entire earth is the ocean, 3.5% of sea water is salt, and 2.18 g of NaCl is contained in 1 liter of sea water. Sodium (Na) is considered as a next-generation energy source to replace fossil fuel and nuclear fuel. Hydrogen fuel made from sodium material is a source of clean energy, which does not emit $CO_2$ or radioactivity. Further, there is no risk of depletion and the supply is not influenced by the hegemonism or political conditions of the resource countries, which may lead to the peaceful world without resource war. It is more desirable for industry to site in the location of raw material rather than the location of consumption. Further, it is desirable for the power for processing a raw material to site near the location of extraction of the raw material. Based on this, an offshore factory 110 is made to float on the ocean and to use the sea water directly under as a raw material. As the electric power of the processing, natural power sources may be used, such as off-shore wind power and solar power, or a buoyancy gravity power, which may be obtained with use of a buoyancy gravity power generator 113 reciprocated between the seabed and sea surface to create about 1000 times as much power as that of wind force, disclosed by the inventor of the present application in Patent Literatures 19 and 20. Thus, with use of the hydrogen-producing apparatus 86 shown in FIG. 31, hydrogen is produced using the hydraulic pressure under sea surface. Then, with the caustic soda producing devices 90 or 91 shown in FIG. 33 or FIG. 34, caustic soda and hydrochloric acid or chlorine are produced. Besides the natural energy power generation, excessive power or midnight power of, for example, a seaside thermal power plant and nuclear power plant, may be used in a seaside factory 111 to produce hydrogen and caustic soda. Here, the melting point of caustic soda is as low as 318° C. as shown in FIG. 16. Thus, caustic soda molten heated by the heater in the base metal hydride-producing device 97 is provided with positive and negative electrodes, and a reverse voltage is applied to hydrogen gas to react the anions of hydrogen thus produced and cations of sodium, producing sodium hydride 49. Further, the power consumption for producing sodium hydride by the ionic reaction is low, and further as shown in FIG. 16, the specific gravity of sodium hydride is 0.92, lower than that of caustic soda molten salt, 2.13, and the melting point of sodium hydride is 800° C., which is higher than that of caustic soda, 318° C. Therefore, sodium hydride can be easily surfaced as upper residual, which can be easily subjected to gravity classification. If the sodium hydride 49 produced here is inserted in the hydrogen-producing device 112 and water is poured thereto, twice as much hydrogen as that by hydrolysis reaction with metallic sodium is produced. The hydrogen produced here is sent to a thermoelectric power station or a hydrogen station through a pipeline. On the other hand, the caustic soda 31, which is a waste (byproduct) made with the hydrogen-producing device 112 is used as a raw material of the base metal hydride-producing device 97, and thus sodium hydride 49 is produced again. Thus, a caustic soda fuel cycle is realized, so much safer than a nuclear fuel cycle. Part of the caustic soda made by the caustic soda producing devices 90 and 91 is used for a stacked-layer type caustic soda battery shown in FIG. 41, as an in-vehicle battery or a power storage battery. Moreover, if sodium hydride is immersed in oil and a compact version of the hydrogen producing device 112 is mounted in a vehicle, a hydrogen-fueled car without an in-vehicle hydrogen cylinder can be made. Thus, a caustic soda fuel cycle system for constructing the hydrogen society, which does not depend on fossil fuel can be realized.

Figure 45:
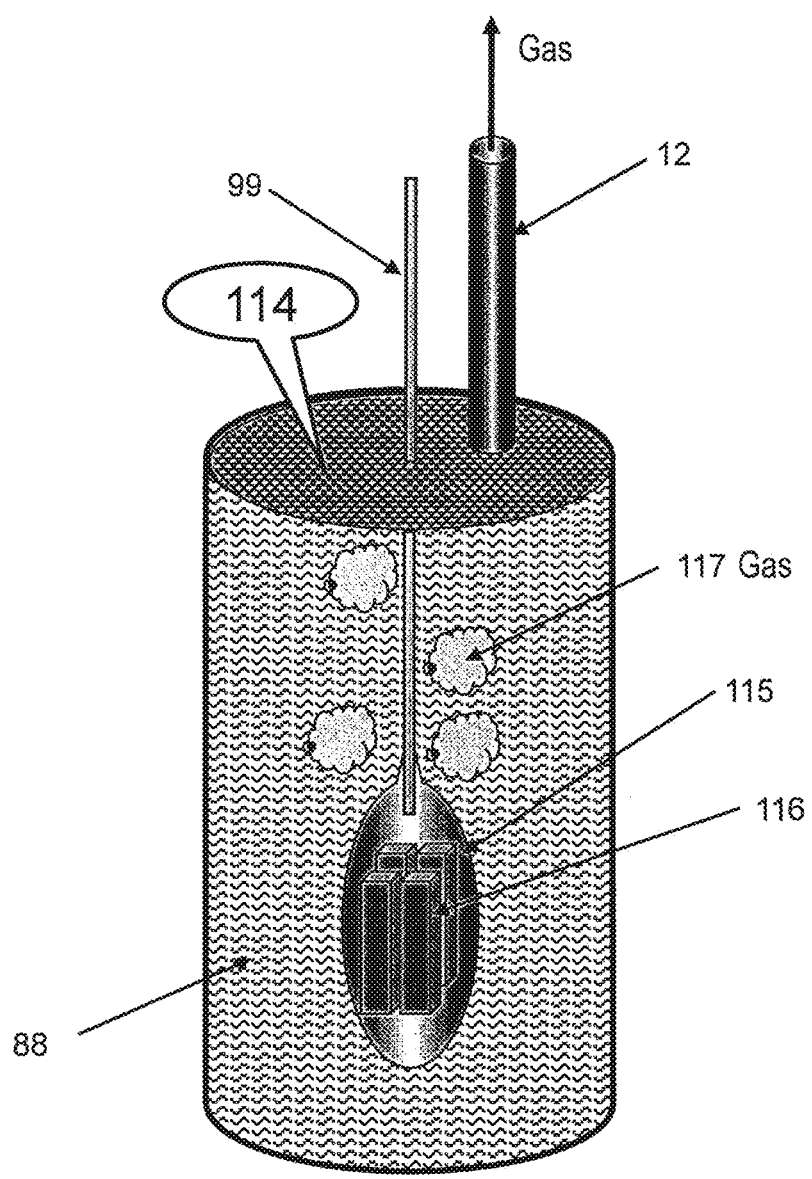
FIG. 45 is a diagram briefly showing a hydrolysis reactor.

FIG. 45 is a schematic diagram of hydrolysis reaction control device. A water-repellent porous fluororesin-made sealed bag 115 accommodating a chemical 116 is inserted in the hydrolysis reaction control device 114 and water 88 is put into the water-repellent porous fluororesin-made sealed bag 115 from outside. Thus, the device can be used for producing a gas by hydrolysis, generation or absorption of heat, or dissolution reactions. In the present invention, the most remarkable phenomenon can be obtained with Na, K, and Li of Group 1, in which hydrogen is produced if a chemical 116 such as one of these is put into the water-repellent porous fluororesin-made sealed bag 115 and water is made to permeate thereto with a differential pressure higher than or equal to the water-resistant pressure. However, the fluororesin is corroded and degraded by these Group 1 element. In order to prevent this and to have a safe hydrolysis reaction, an oil such as gas oil should be put together with the Group 1 element in the water-repellent porous fluororesin-made sealed bag 115 since the fluororesin exhibits lipophilic properties in water and is not brought into direct contact with Na, K, Li or the like within the water-repellent porous fluororesin-made sealed bag 115, making it possible to avoid the degradation. For example, if sodium bicarbonate as the chemical 116 and citric acid (1:1) are put thereinto, carbon dioxide ($CO_2$) is produced. Here, it can be used as a source of gas for acquiring the buoyancy of a buoyancy gravity power generator 113 (FIG. 44) disclosed by the inventor of the present application in Patent Literatures 19 and 20, for the case where the depth of water is 1300 m or shallower. If calcium oxide (CaO) and aluminum (Al) are used as the chemicals 116, the following reaction can be obtained: $2CaO+2Al+4H_2O \rightarrow 2Ca(OH)_2+2Al+2H_2O+63.3$ kJ/mol $\rightarrow 2CaO+Al_2O_3+H_2+390.1$ kJ/mol to obtain a high temperature and hydrogen simultaneously. Here, the weight of these chemicals is used as a weight when a submersible vehicle descends to the deep ocean floor, and the sea water of the deep ocean floor is used as a water source to produce hydrogen. Further, the heat simultaneously generated here can be used to increase the volume of the gas, which can be used as a buoyancy gas of the submersible vehicle. With this heat, dry ice is sublimated in the deep ocean floor deeper than a depth of 1300 m, to be used also as a buoyancy agent. If urea (($NH_2$)$_2$CO) is put thereinto as the chemical 116, the reaction $2(NH_2)CO+H_2O \rightarrow 2NH_3+CO_2$ occurs to give ammonia and carbon dioxide. If carbide ($CaC_2$) is used, the reaction: $CaC_2+2H_2O \rightarrow Ca(OH)_2+C_2H$ occurs to produce acetylene gas. As the chemical 116, a nonelectrolyte such as sugar, a seasoning, a nutrient, or medicine can be put thereinto to cause a dissolution reaction with water 88.

Figure 46:
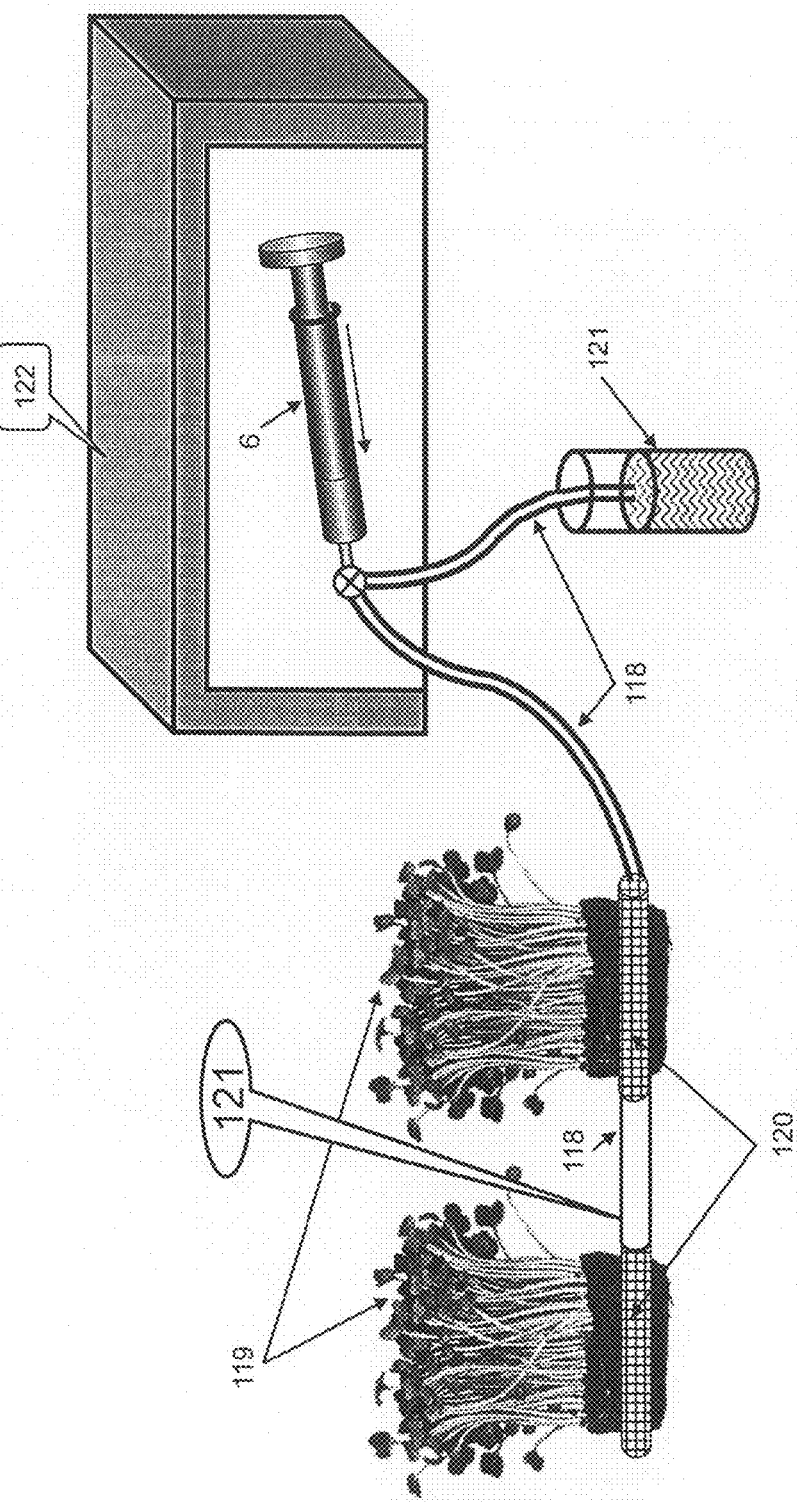
FIG. 46 is a diagram briefly showing a water/fertilizer supplier for hydroponics.

FIG. 46 is a schematic diagram of a device of supplying a nutrient or moisture in hydroponics. A nutrient supply device 121 is a device which intermittently supplies water and nutrient controlled by the hydraulic pressure for vegetation 119 such as vegetables and fruit trees in plant factories or vegetable factories. To this device, a chemical-spraying pot (a water-repellent porous resin bag or tube) 120 is connected via a solution supplying pipe (hose) 118. Thus, a supplement nutrient 121 such as a fertilizer or moisture is delivered to a desired site continuously or intermittently as needed with a pressure-applying member 6 by a control room 122 of a plant factory, to supply moisture and nutrient (fertilizer) efficiently to the root part of the plant, thereby making it possible to suppress root rot caused by excessive water supply or excess nutrition.

Figure 47:
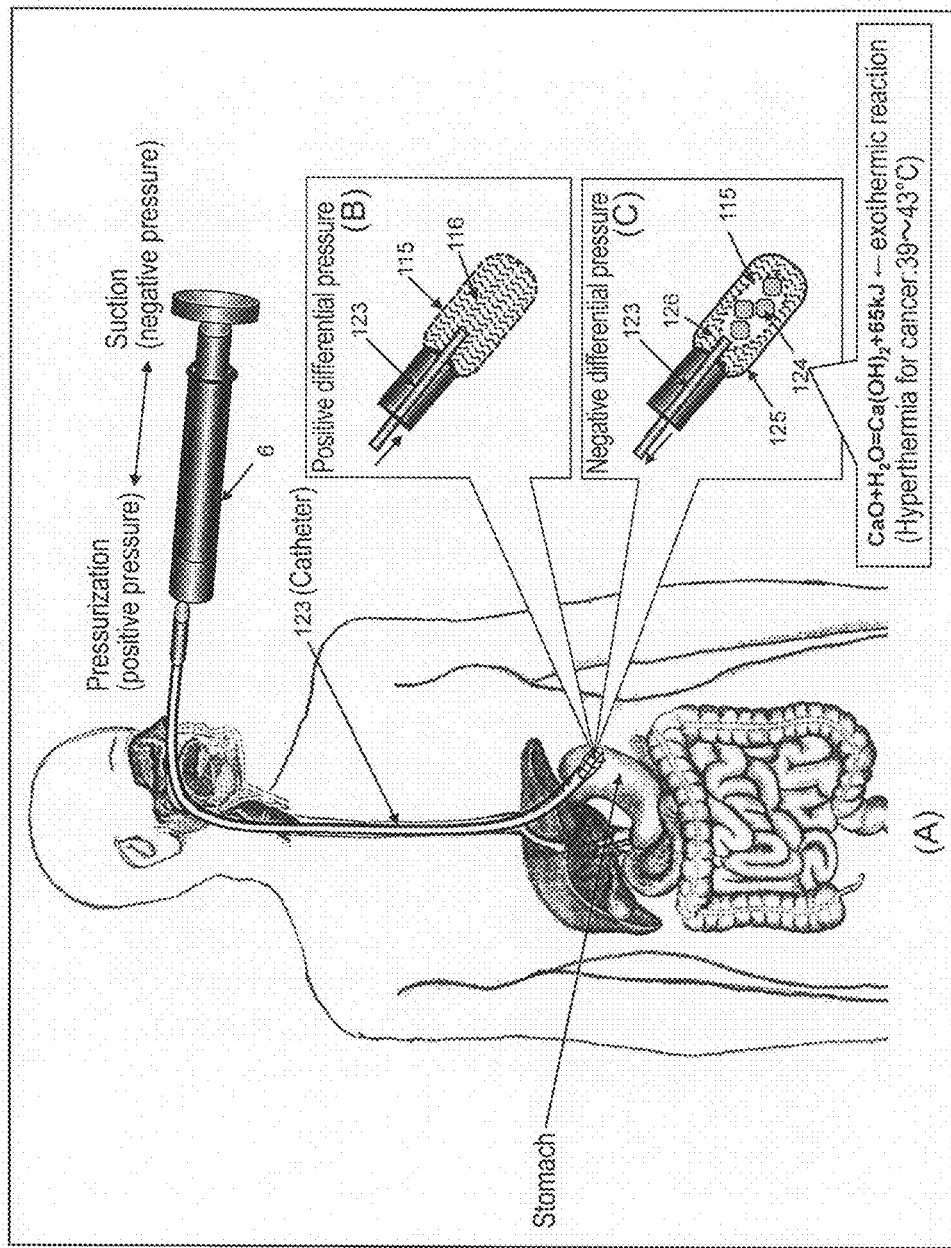
FIG. 47 is an explanatory diagram of an endoscope type medical device, in which (A) shows a cross section of a human body, (B) shows a tube-feeding nutritious/chemicals capsule and (C) shows a capsule of thermatological therapy for cancer.

FIG. 47 is a diagram briefly showing an endoscope type medical device. As shown in FIG. 47(A), a catheter 123 is inserted into an organ, and the inside of a capsule inserted in the organ is suctioned (negative pressure) or pressurized (positive pressure) with a pressure-applying member 6 to deliver a medicine or an aqueous nutrient solution to the affected part or to heat the affected part. To deliver a medicine or a nutrient to the affected part, the nutrient or medicine 116 is transferred to a water-repellent porous fluororesin-made sealed bag 115 and the solution is pressurized (positive pressure) through the catheter 123 by applying a pressure more higher than or equal to the water-resistant pressure (difference pressure) of the multi-water-repellent porous film with a pressure-applying member 6 as shown in FIG. 47(B). Thus, the nutrient or medicine can be efficiently supplied to a required place. In this manner, the nutrient or medicine can be administered at high efficiency to match the life rhythm of the subject without administering at all times as in the present intravenous drip or tube feeding administration. In the treatment of a affected part, the medicine can be administered only to the target affected part.

FIG. 47(C) is a schematic diagram of a thermotological therapeutic capsule 125 for killing cancer cells. Cancer cells are weakest at a temperature of 39 to 43° C., which is a comparatively low temperature similar to the temperature of a bath. However, it is difficult to heat the affected part directly at a constant temperature for a long time. Here, a preliminary test was virtually conducted. First, a water-repellent porous fluororesin-made sealed bag 115 containing a hydrolytic exothermic agent 124 is inserted to the capsule 125 enclosing water 88, and the inside of the water-repellent porous fluororesin-made sealed bag 115 is suctioned (negative pressure) by a differential pressure equivalent to the water-resistant pressure to be created with a catheter 123 (shade). Thus, the water 88 inside the capsule 125 permeates into the water-repellent porous fluororesin-made sealed bag 115 in the amount equivalent to the negative pressure, and the water reacts with the hydrolytic exothermic agent 124 to generate heat. The water 88 inside the capsule 126 is heated with thus generated heat. Therefore, in an actual clinical testing, the affected part in which cancer cells live can be warmed directly. The negative pressure was repeated in pulse, and thus the water was supplied to the hydrolytic exothermic agent 124 by the negative pressure. Thus, the hydrolysis exothermic agent 124 and the water 88 are made to react with each other to maintain a temperature of 39 to 43° C. for about 30 minutes. The heat value of the hydrolytic exothermic agent 124, if CaO is used, is 65 kJ/mol; 18.1 kJ/mol for $P_2O_3+ZnCl_2+Ba(OH)_2$; 12.6 kJ/mol for NaOH; 39.5 kJ/mol for KOH; 37 kJ/mol for sulfuric acid; 97.4 kJ/mol for $CaCl_2$; 126 kJ/mol for $Al_2O_3$; 27.5 kJ/mol for $CuSO_4$; and 390.1 kJ/mol for CaO+Al. Thus, in consideration of the amount of injection to a capsule, temperature reached, time duration and the like, it is considered that in clinical application, CaO is suitable as an exothermic agent.

The recoverable reserves of petroleum and coal are limited, and these materials emit carbon dioxide. Nuclear fuel emits radioactivity. In contrast, hydrogen is limitless in recoverable reserves and emits no carbon dioxide or radioactivity. Thus, hydrogen is a clean fuel friendly also to environment. Hydrogen itself is light; however its container (cylinder) to store it or alloys which occlude hydrogen are too heavy to carry. As a solution, hydrogen is searched from a resource of hydrogen (that is, sodium). Sodium is allover the place and well distributed in the form of sea water or rock salt, and it will not be short. But in order to collect it, water must be removed. Conventionally, there has been no collecting means other than a molten salt electrolysis. With the present invention, sea water is electrolyzed directly to collect metallic sodium. Caustic soda can also be produced without an ionic exchange resin. Further, hydrogen and oxygen can be produced merely by applying electric potential between the positive and negative electrodes sunk under a sea surface. Furthermore, base metal/air secondary batteries such as of lithium, sodium, potassium and calcium, whose electrolytes are aqueous solutions, or base metal/halogen secondary batteries can be manufactured, in which the economic effect is huge. In particular, as alternative energy to petroleum, the metallic sodium obtained from sea water can make a great contribution to the industries of our country as a resource of generating electric power without concerning about its shortage or uneven distribution, or as a base metal aqueous solution secondary battery with high power generation efficiency.

EXPLANATION OF REFERENCE NUMERALS

1 . . . sealed container
2 . . . open container
3 . . . negative electrode chamber
4 . . . positive electrode chamber
5 . . . communicating tube
6 . . . pressure-applying member (cylinder)
7 . . . dropper rubber, pipette
8 . . . electrically-driven pressurizing device with a ratchet
9 . . . water tank
10 . . . position head (h)
11 . . . liquid (water)-repellent porous membrane (isolation film)
12 . . . produced-gas collecting hose
13 . . . alcohol
14 . . . aqueous electrolyte solution
15 . . . solute (chemical)
16 . . . oil-filled electrode chamber
17 . . . positive electrode plate (within oil tank)
18 . . . intermediate electrode plate (in oil tank)
19 . . . virtual negative electrode surface (interface between oil and electrolyte)
20 . . . charge (voltage)
21 . . . positive electrode plate in electrolyte
22 . . . oil
23 . . . oil (specific gravity of 1 or less)
24 . . . oil (specific gravity of more than 1)
25 . . . acid (hydrochloric acid in the case of chloride)
26 . . . negative electrode product collecting port
27 . . . liquid/water-repellant porous membrane (for freshwater permeation)
28 . . . tap water (utilization of water pressure)
29 . . . large-sized sealed container
30 . . . hydrogen-producing apparatus
31 . . . base metal hydroxide (caustic soda)
32 . . . aqueous base metal chloride solution (aqueous sodium chloride solution)
33 . . . concentrated acid (hydrochloric acid)
34 . . . water supply inlet
35 . . . negative electrode product collecting port
36 . . . negative electrode plate
37 . . . positive electrode (carbon fibers, carbon particles, porous carbon)

38 . . . positive electrode plate
39 . . . aqueous base metal salt solution supply tank
40 . . . water-filled electrode chamber
41 . . . gas-permeable electrode chamber
42 . . . positive electrode product collecting port (concentrated acid outlet)
43 . . . mesh negative electrode (carbon fibers, metal mesh)
44 . . . porous carbon negative electrode plate-cum-isolation film
45 . . . hydrogen gas
46 . . . base metal hydroxide molten salt (caustic soda)
47 . . . hydrogen-gas injection port
48 . . . molten-salt heating heater
49 . . . base metal hydride (sodium hydride)
50 . . . hydrogen anion
51 . . . base metal hydride collecting port
52 . . . negative electrode chamber (for battery and for capacitor)
53 . . . positive electrode chamber (for battery and for capacitor)
55 . . . envelope-type sealed container
56 . . . auxiliary positive electrode for charging (mesh electrode)
57 . . . outside air isolation type negative electrode
58 . . . carbon-made porous electrode plate (activated carbon)
59 . . . metal oxide film (for positive electrode of battery) ($CuO$, $AlO_3$, $ZnO_2$)
60 . . . metal plate (for battery) (Cu, Al)
61 . . . resin film
62 . . . negative electrode plate (for battery) (Al, Mg, Ca, Zn, Ni, Pb)
63 . . . metal chloride film (for positive electrode of battery) ($ZnCl_2$)
64 . . . collector electrode plate (for battery) (Cu, Al)
65 . . . negative electrode plate (Al, Mg, Zn)
66 . . . positive electrode (chloride of metal used for negative electrode)
67 . . . activated carbon particle or carbon fiber
68 . . . bromine liquid
69 . . . iodine particle
70 . . . graphite plate
71 . . . aluminum (Al) negative electrode plate
72 . . . dielectric solution (oil-based, water-based)
73 . . . electrode plate (capacitor)
74 . . . electric double layer electrode (capacitor)
75 . . . redox capacitor electrode
76 . . . hybrid capacitor electrode
77 . . . encircling dotted line
78 . . . electrically conductive material with voids (metal fiber, carbon fiber, activated carbon)
79 . . . aqueous electrolyte solution for electrochemical capacitor (diluted sulfuric acid)
80 . . . diluted caustic soda (aqueous electrotype solution for electrochemical capacitor)
81 . . . stainless steel fiber
82 . . . carbon fiber
83 . . . inter-electrode distance (d)
84 . . . hydrogen-producing apparatus under sea surface
85 . . . multistage type hydrogen-producing apparatus under sea surface
86 . . . hydrogen producing apparatus under lake surface (under sea surface)
87 . . . quadrangular prism-shaped sealed container
88 . . . freshwater (water)
89 . . . simple hydrogen-producing apparatus utilizing the pressure of tap water
90 . . . device directly producing caustic soda and chlorine gas from aqueous sodium chloride solution
91 . . . device directly producing caustic soda and hydrochloric acid from aqueous sodium chloride solution
92 . . . base metal producing device
93 . . . primary pressure regulating valve (gas-permeable electrode chamber)
94 . . . suction port (down to not more than water-resistant pressure by vacuum pump)
95 . . . device directly producing base metal element and hydrochloric acid
96 . . . base metal producing device utilizing virtual negative electrode
97 . . . metal hydride producing device
98 . . . aqueous electrolyte solution reserving device
99 . . . suction port (vacuum pump)
100 . . . water-repellent porous membrane (11a)
101 . . . water-repellent porous membrane (11b)
102 . . . aqueous electrolyte solution for reservation
103 . . . electrolyte pressurization type secondary battery
104 . . . weight
105 . . . air inlet
106 . . . stacked-layer type caustic soda battery
107 . . . redox capacitor
108 . . . metal plate for redox capacitor
109 . . . metal oxide film for redox capacitor
110 . . . offshore factory
111 . . . seaside factory (seaside power station)
112 . . . hydrogen-producing device
113 . . . buoyancy gravity power generator
114 . . . hydrolysis reaction control device
115 . . . water-repellent porous fluororesin sealed bag
116 . . . chemical
117 . . . gas
118 . . . aqueous solution supplying pip (hose)
119 . . . plant (vegetable, fruit tree)
120 . . . chemical-spraying pot (a water-repellent porous resin bag or tube)
121 . . . supplement nutrient (vegetable factory)
122 . . . control room
123 . . . catheter (tube)
124 . . . exothermic agent (CaO)
125 . . . capsule

What is claimed is:

1. An electrochemical reactor comprising:
a positive electrode with a first major surface and a second major surface on an opposite side to the first major surface;
a negative electrode with a first major surface and a second major surface on an opposite side to the first major surface, wherein the positive electrode and the negative electrode oppose with the first major surfaces thereof facing with each other and are arranged apart from each other, defining a space therebetween;
an electrically conductive liquid or a dielectric liquid which fills the space;
a first isolation member which is provided on the first major surface of the positive electrode and isolates the positive electrode from the liquid, wherein the first isolation member comprises a first water-repellent porous membrane formed of a fluororesin and having a plurality of pores;
a second isolation member which is provided on the first major surface of the negative electrode and isolates the negative electrode from the liquid, wherein the second isolation member comprises a second water-repellent porous membrane formed of a fluororesin and having a plurality of pores; and a pressure-applying member which is configured to pressurize the liquid at a pressure equal to water-resistant pressure of the first and second water-repellent porous membranes to fill the liquid into the pores of the first and second water-repellent porous membranes, thereby causing an electrochemical reaction involving the positive electrode and the negative electrode.

2. The electrochemical reactor of claim 1, wherein the liquid is an aqueous electrolyte solution.

3. The electrochemical reactor of claim 1, wherein is an aqueous electrolyte solution, and in order to change the pressure value of the water-resistant pressure, a water-repellent group or a hydrophilic group is added to a surface and/or pore walls of each the first and second water-repellent porous membranes, the first and second water-repellent porous membranes comprising pores having different diameters are used, a salt concentration and/or a liquid temperature of the aqueous electrolyte solution are changed, or a potential is applied between the first and second water-repellent porous membranes, thereby controlling a quantity of the water or ion which can permeate the first and second water-repellent porous membranes according to the pressure of the liquid.

4. The electrochemical reactor of claim 1, wherein
when the liquid is an aqueous electrolytic solution and the positive and negative electrodes are used as a battery,
if the negative electrode is of an amphoteric element, Mg or a metallic element having an ionization tendency higher than that of hydrogen excluding those of Group 1 or 2, and the positive electrode is of oxygen or graphite fluoride, both electrodes are bare electrodes exposed to outside air, or
if the negative electrode is of an element from Group 1 or 2 and the positive electrode is of a halogen or a halide compound, both electrodes are electrode chambers shielded from the outside air.

5. The electrochemical reactor of claim 1, wherein
when the liquid is an aqueous electrolytic solution and the positive and negative electrodes are used as electrolysis,
if a gaseous electrode product is produced in both electrodes, both electrodes are gas-permeable electrode chambers of a structure, the insides of which is formed into a porous electrode exhibiting a texture of mesh, fibers, porous material or grains or gas-permeable electrode chambers of a structure that a back surface of the porous electrode includes a gap.

6. The electrochemical reactor of claim 1, wherein
when the liquid is an aqueous electrolytic solution and the positive and negative electrodes are used as electrolysis,
if a gaseous electrode product of an element from Group 1, 2 and/or 13 of the periodic table is produced in both electrodes, the positive electrode is a gas-permeable electrode chamber of a structure, the inside of which is formed into a porous electrode exhibiting a texture of mesh, fibers, porous material or grains or a gas-permeable electrode chamber of a structure that a back surface of the porous electrode includes a gap, and the negative electrode is an oil-filled electrode chamber with an electrode chamber structure filled with oil, and pores of a porous electrode or a gap at the back surface thereof are filled with an oil to subject the negative electrode product to heavy liquid separation, or an electrode plate is provided at the back surface of the oil.

7. The electrochemical reactor of claim 1, wherein
the liquid is an oil aqueous dielectric,
the positive and negative electrodes are used as a capacitor,
the positive and negative electrodes are electrode plates which form a structure to interpose an oil or aqueous dielectric both via the first and second water-repellent porous membranes, or of an electric double layer type in which organic molecules are adsorbed on the surface of an activated carbon electrode, or redox type electrodes of a metal oxide.

8. An electrochemical reactor comprising:
a positive electrode with a first major surface and a second major surface on an opposite side to the first major surface;
a negative electrode with a first major surface and a second major surface on an opposite side to the first major surface, wherein the positive electrode and the negative electrode oppose with the first major surfaces thereof facing with each other and are arranged apart from each other, defining a space therebetween;
a first isolation member which is provided on the first major surface of the positive electrode and isolates the positive electrode from the space, wherein the first isolation member comprises a first water-repellent porous membrane formed of a fluororesin and having a plurality of pores;
a second isolation member which is provided on the first major surface of the negative electrode and isolates the negative electrode from the space, wherein the second isolation member comprises a second water-repellent porous membrane formed of a fluororesin and having a plurality of pores;
an open container which contains an aqueous electrolytic solution; and
a pressure-applying member configured to descend the positive electrode, the negative electrode, together with the first isolation member and the second isolation member to the aqueous electrolytic solution contained in the open container,
wherein
the positive electrode and the negative electrode are descended together with the first isolation member and the second isolation member to the aqueous electrolytic solution contained in the open container, to such a depth that a pressure equal to water-resistant pressure of the first and second water-repellent porous membranes is obtained, and thus the aqueous electrolytic solution is pressurized to exude through the first and second water-repellent porous membranes to the positive electrode and the negative electrode, thereby causing an electrochemical reaction of the aqueous electrolytic solution between the positive electrode and the negative electrode.

9. An electrochemical reactor comprising:
a positive electrode with a first major surface and a second major surface on an opposite side to the first major surface;
a negative electrode with a first major surface and a second major surface on an opposite side to the first major surface, wherein the positive electrode and the negative electrode oppose with the first major surfaces thereof facing with each other and are arranged apart from each other, defining a space therebetween;

a sealed container disposed in the space to be in contact with the first major surfaces of the positive electrode and the negative electrode, and containing an aqueous electrolytic solution, wherein surfaces of the sealed container, which are in contact with the first major surfaces of the positive electrode and the negative electrode, are a first isolation member and a second isolation member, respectively, and the first isolation member comprises a first water-repellent porous membrane formed of fluororesin and having a plurality of pores and the second isolation member comprises a second water-repellent porous membrane formed of fluororesin and having a plurality of pores; and a pressure-applying member which pressurizes the aqueous electrolytic solution contained in the sealed container, wherein the pressure-applying member pressurizes the aqueous electrolytic solution contained in the sealed container to a pressure equal to water-resistant pressure of the first and second water-repellent porous membranes, and thus the aqueous electrolytic solution exudes through the first and second water-repellent porous membranes to the positive electrode and the negative electrode, thereby causing an electrochemical reaction of the aqueous electrolytic solution between the positive electrode and the negative electrode.

10. The electrochemical reactor of claim 9, wherein the pressure-applying member comprises a water tank which contains the aqueous electrolytic solution and which is connected with a communicating tube to the sealed container containing the aqueous electrolytic solution, the water tank being installed at a height where such a pressure head is obtained that the pressure of this aqueous electrolytic solution becomes equal to the water-resistant pressure of the first and second water-repellent porous membranes.

11. The electrochemical reactor of claim 9, wherein the pressure-applying member comprises a pressurizing device with a ratchet, connected to the sealed container containing the aqueous electrolytic solution via a communicating tube, wherein the aqueous electrolytic solution in the sealed container is pressurized to a pressure equal to the water-resistant pressure of the first and second water-repellent porous membranes by manually or electrically operating the pressurizing device with a ratchet.

12. The electrochemical reactor of claim 9, wherein the pressure-applying member pressurizes the sealed container containing the aqueous electrolytic solution by an arbitrary surface outside the sealed container.

13. The electrochemical reactor of claim 9, wherein the pressure-applying member comprises a container connected to a faucet of a tap, and the sealed container is inserted to tap water in the container and pressurized to a pressure higher than or equal to the water-resistant pressure of the first and second water-repellent porous membranes by a water pressure of the tap water.

14. An electrochemical reactor which produces hydrogen by directly electrolyzing an aqueous electrolyte solution consisting of a sea or a salt lake, the reactor comprising:

a plurality of sets of gas-permeable electrode chambers prepared by connecting a set of gas-permeable electrode chambers in which a pair of positive and negative gas-permeable electrode chambers are arranged to be close to each other, to each other or by connecting a set of gas-permeable electrode chambers;

first and second isolation members provided on respective surfaces of the pair of positive and negative gas-permeable electrode chambers arranged to be close to each other, wherein the first and second isolation members, respectively, comprise first and second water-repellent porous membranes each formed of a fluororesin and having a plurality of pores; and a pressure-applying member configured to submerge the pair of positive and negative gas-permeable electrode chambers, together with the first and second isolation members, into the aqueous electrolyte solution, wherein the pair of gas-permeable electrode chambers, and the first and second isolation members are submerged, by the pressure-applying member, into the aqueous electrolytic solution to such a depth that a pressure equal to water-resistant pressure of the first and second water-repellent porous membranes is obtained, and thus the aqueous electrolyte solution is pushed with pressure into the pair of gas-permeable electrode chambers via the first and second water-repellent porous membranes, to be electrolyzed at a voltage higher than or equal to a decomposition voltage, thereby producing hydrogen gas in the negative gas-permeable electrode chamber and oxygen gas or chlorine gas in the positive gas-permeable electrode chamber.

15. An electrochemical reactor which produces hydrogen by directly electrolyzing an aqueous electrolyte solution, the reactor comprising:

a pair of positive and negative gas-permeable electrode chambers arranged to be close to each other;

a sealed container containing the aqueous electrolytic solution and disposed between the pair of positive and negative gas-permeable electrode chambers so as to be in contact with the gas-permeable electrode chambers, wherein the sealed container comprises surfaces brought into contact with the pair of positive and negative gas-permeable electrode chambers, which are respectively first and second isolation members, and the first and second isolation members respectively comprise first and second water-repellent porous membranes each formed of a fluororesin and having a plurality of pores; and a pressure-applying member which pressurizes the aqueous electrolyte solution contained in the sealed container, wherein the aqueous electrolyte solution contained in the sealed container is pressurized by the pressure-applying member to a pressure equal to water-resistant pressure of the first and second water-repellent porous membranes, and thus the aqueous electrolyte solution is pushed with pressure into the pair of positive and negative gas-permeable electrode chambers via the first and second water-repellent porous membranes, to be electrolyzed at a voltage higher than or equal to a decomposition voltage, thereby producing hydrogen gas in the negative gas-permeable electrode chamber and oxygen gas or chlorine gas in the positive gas-permeable electrode chamber.

16. An electrochemical reactor comprising:

a pair of positive and negative gas-permeable electrode chambers spaced from each other;

a sealed container filled with a first aqueous electrolytic solution and disposed between the pair of positive and negative gas-permeable electrode chambers so as to be in contact with the gas-permeable electrode chambers, wherein the sealed container comprises surfaces brought into contact with the pair of positive and negative gas-permeable electrode chambers, which are respectively first and second water-repellent porous membranes each formed of a fluororesin and having a plurality of pores, and further comprises a water-repellent porous membrane for pressing aqueous solution thereinto, which, in part, comprises a plurality of pores;

an open container filled with a second aqueous electrolytic solution which has a concentration lower than a concentration of the first aqueous electrolytic solution; and a pressure-applying member which puts the pair of positive and negative gas-permeable electrode chambers and the sealed container disposed therebetween into the second aqueous electrolytic solution in the open container, wherein the pair of positive and negative gas-permeable electrode chambers and the sealed container disposed therebetween are put into the second aqueous electrolytic solution in the open container by the pressure-applying member to descend the closed container to a pressure head position, to pressurize with a pressure higher than or equal to the water-resistant pressure of the water-repellent porous membrane for pressing the aqueous solution thereinto, thus allowing the second aqueous electrolytic solution to permeate inside the sealed container via the water-repellent porous membrane, to also cause pressurization on a diluted first aqueous electrolytic solution, to fill the solution into the pores of the first and second water-repellent porous membranes, thereby electrolyzing the first aqueous electrolytic solution at a voltage higher than or equal to the decomposition voltage of water to produce hydrogen gas in the negative electrode chamber and oxygen gas in the positive electrode chamber.

17. An electrochemical reactor comprising:

a pair of positive and negative gas-permeable electrode chambers spaced from each other;

a sealed container filled with an aqueous electrolytic solution and disposed between the pair of positive and negative gas-permeable electrode chambers so as to be in contact with the gas-permeable electrode chambers, wherein the sealed container comprises surfaces brought into contact with the pair of positive and negative gas-permeable electrode chambers, which are respectively first and second water-repellent porous membranes each formed of a fluororesin and having a plurality of pores, and further comprises a water-repellent porous membrane for pressing aqueous solution thereinto, which, in part, comprises a plurality of pores;

a second container; and a pressure-applying member comprising a faucet of a tap for supplying tap water into the second container, wherein the pair of positive and negative gas-permeable electrode chambers and the sealed container disposed therebetween are put into the second container, and the tap water is supplied into the second container from the faucet of the tap of the pressure-applying member to pressurize with a pressure higher than or equal to water-resistant pressure of the water-repellent porous membrane for pressing the aqueous solution thereinto, thus allowing the tap water to permeate inside the sealed container via the water-repellent porous membrane, to also cause pressurization on a diluted aqueous electrolytic solution, to fill the solution into the pores of the first and second water-repellent porous membranes, thereby electrolyzing the solution at a voltage higher than or equal to the decomposition voltage of water to produce hydrogen gas in the negative electrode chamber and oxygen gas in the positive electrode chamber.

18. An electrochemical reactor which produces an aqueous solution of a base metal hydroxide on a negative electrode by electrolyzing an aqueous electrolytic solution of a base metal chloride, a base metal nitrate or a base metal sulfide, the reactor comprising:

a positive gas-permeable electrode chamber;

a water-filled electrode chamber comprising a negative electrode formed of a metal or carbon and containing water to which an alkali is added;

a sealed container filled with the aqueous electrolytic solution and disposed to oppose the positive gas-permeable electrode chamber and the water-filled electrode chamber with a gap therebetween so as to be in contact with the positive gas-permeable electrode chamber and the water-filled electrode chamber, wherein the sealed container comprises surfaces brought into contact with the positive gas-permeable electrode chamber and the water-filled electrode chamber, which are respectively first and second water-repellent porous membranes each formed of a fluororesin and having a plurality of pores; and a pressure-applying member which pressurizes the aqueous electrolytic solution contained in the sealed container, wherein the water-filled electrode chamber comprises an inlet for water, an outlet port for a produced concentrated aqueous base metal hydroxide solution and an outlet port for a negative electrode product gas in an upper part thereof, and the aqueous electrolytic solution contained in the sealed container is pressurized by the pressure-applying member to a pressure equal to water-resistant pressure of the first and second water-repellent porous membranes, and thus the aqueous electrolytic solution is pushed with pressure into the positive gas-permeable electrode chamber and the water-filled electrode chamber via the first and second water-repellent porous membranes of the sealed container, to be electrolyzed, thereby producing a positive electrode produced gas in the positive gas-permeable electrode chamber and a concentrated aqueous base metal hydroxide solution in the water-filled electrode chamber of the negative electrode side, continuously.

* * * * *